US011666925B2

(12) United States Patent
Hinz et al.

(10) Patent No.: US 11,666,925 B2
(45) Date of Patent: Jun. 6, 2023

(54) SINGLE-USE CENTRIFUGE CONTAINERS FOR SEPARATING BIOLOGICAL SUSPENSIONS AND METHODS OF USE

(71) Applicant: Thermo Electron LED GmbH, Langenselbold (DE)

(72) Inventors: Romana Hinz, Windhausen (DE); Norman Ballhause, Datteln (DE); Jason D. Brown, Logan, UT (US); Ileana Place, East Greenwich, RI (US); Hugh H. Tansey, III, Southbury, CT (US)

(73) Assignee: Thermo Electron LED GmbH, Langenselbold (DE)

( * ) Notice: Subject to any disclaimer, the term of this patent is extended or adjusted under 35 U.S.C. 154(b) by 1083 days.

(21) Appl. No.: 16/289,296

(22) Filed: Feb. 28, 2019

(65) Prior Publication Data

US 2019/0270096 A1    Sep. 5, 2019

Related U.S. Application Data

(60) Provisional application No. 62/637,561, filed on Mar. 2, 2018.

(51) Int. Cl.
*B04B 5/04*       (2006.01)
*B04B 11/04*      (2006.01)
(Continued)

(52) U.S. Cl.
CPC ............ *B04B 5/0428* (2013.01); *B04B 11/04* (2013.01); *C12M 23/14* (2013.01); *C12M 23/28* (2013.01);
(Continued)

(58) Field of Classification Search
CPC . B04B 5/0428; B04B 11/04; B04B 2011/046; C12M 23/14; C12M 23/28;
(Continued)

(56) References Cited

U.S. PATENT DOCUMENTS 4,284,209 A      8/1981   Barbour, Jr.
4,322,298 A *    3/1982   Persidsky ............ G01N 33/491
                                                  494/21

(Continued)

FOREIGN PATENT DOCUMENTS

DE       690 27 962 T2    1/1997
DE       100 65 283 A1    7/2002
(Continued)

OTHER PUBLICATIONS

J. Hardwick, *Blood Processing*, Section 11, ISBT Science Series, 2008, vol. 3, pp. 148-176.
(Continued)

*Primary Examiner* — Shuyi S. Liu
(74) *Attorney, Agent, or Firm* — Workman Nydegger

(57) ABSTRACT

A method for separating a biological suspension includes dispensing a liquid suspension comprised of cells or microorganisms from a bioreactor or fermenter into a sterile compartment of a first bag assembly, the first bag assembly including a collapsible bag having of one or more sheets of flexible film. The compartment of the first bag assembly is sealed closed. The first bag assembly, either with or without a manifold fluid coupled therewith, is then rotated, such as by using a centrifuge, so that the liquid suspension separates within the compartment into a pellet comprised of the cells or microorganisms and a liquid supernatant.

31 Claims, 30 Drawing Sheets

(51) Int. Cl.
*C12M 1/12* (2006.01)
*C12M 1/00* (2006.01)
*C12M 1/26* (2006.01)

(52) U.S. Cl.
CPC ............ *C12M 23/40* (2013.01); *C12M 29/00* (2013.01); *C12M 33/10* (2013.01); *C12M 37/04* (2013.01); *C12M 47/02* (2013.01); *B04B 2011/046* (2013.01)

(58) Field of Classification Search
CPC ...... C12M 23/40; C12M 29/00; C12M 33/10; C12M 37/04; C12M 47/02
USPC .............................................. 494/21, 23, 38
See application file for complete search history.

(56) References Cited

U.S. PATENT DOCUMENTS

| | | | |
|---|---|---|---|
| 6,019,716 A * | 2/2000 | Forestell | B04B 5/0428 494/21 |
| 6,083,587 A | 7/2000 | Smith et al. | |
| 6,387,030 B1 | 5/2002 | Moore et al. | |
| 7,371,206 B2 | 5/2008 | Eigemeier et al. | |
| 7,384,783 B2 | 6/2008 | Kunas et al. | |
| 7,487,688 B2 | 2/2009 | Goodwin | |
| 7,682,067 B2 | 3/2010 | West et al. | |
| 7,806,819 B2 | 10/2010 | Eigemeier | |
| 7,829,105 B2 | 11/2010 | Talton et al. | |
| 7,867,761 B2 | 1/2011 | Esser et al. | |
| 8,147,392 B2 | 4/2012 | Piramoon et al. | |
| 8,147,393 B2 | 4/2012 | Piramoon et al. | |
| 8,211,002 B2 | 7/2012 | Piramoon et al. | |
| 8,211,003 B2 | 7/2012 | Betke | |
| 8,273,202 B2 | 9/2012 | Piramoon et al. | |
| 8,282,759 B2 | 10/2012 | Piramoon et al. | |
| 8,323,169 B2 | 12/2012 | Piramoon | |
| 8,323,170 B2 | 12/2012 | Piramoon | |
| 8,323,179 B2 | 12/2012 | Chu et al. | |
| 8,328,708 B2 | 12/2012 | Piramoon et al. | |
| 9,073,650 B2 * | 7/2015 | Goodwin | B65B 1/04 |
| 9,868,124 B2 | 1/2018 | Ballhause | |
| 2002/0068674 A1 * | 6/2002 | Hlavinka | A61M 1/0231 494/45 |
| 2002/0183185 A1 | 12/2002 | Brown et al. | |
| 2003/0077466 A1 | 4/2003 | Smith et al. | |
| 2003/0176267 A1 * | 9/2003 | Eberle | B04B 5/0428 494/21 |
| 2006/0196501 A1 | 9/2006 | Bibbo et al. | |
| 2014/0010739 A1 | 1/2014 | Ballhause | |
| 2016/0193614 A1 | 7/2016 | Piramoon | |
| 2016/0310966 A1 | 10/2016 | Henne et al. | |

FOREIGN PATENT DOCUMENTS

| | | |
|---|---|---|
| EP | 0 348 682 A1 | 1/1990 |
| EP | 1 925 328 A2 | 5/2008 |
| GB | 2505305 A | 2/2014 |
| WO | 2011/003615 A2 | 1/2011 |
| WO | 2013/009765 A2 | 1/2013 |

OTHER PUBLICATIONS

Beckman Coulter, *J-Lite, JLA-8.1000 and JLA-9.1000 Fixed-Angle Rotor Assemblies*, Nov. 2012, pp. 44.

Thermo Fisher Scientific, Inc., *Accelerate Productivity with Unequalled Durability, Thermo Scientific Fiberlite Carbon Fiber Rotors*, at least as early as Mar. 1, 2017, pp. 16.

Thermo Fisher Scientific, Inc., *Thermo Scientific Sorvall BIOS 16 Centrifuge, Performance Simplified at Every Turn*, 2016, pp. 10.

Thermo Fisher Scientific, Inc., *Single-Use BioProcess Containers, Standard and Customized 2D and 3D Fluid Containment Systems*, 2017, pp. 12.

Thermo Fisher Scientific, Inc., *Medifuge Centrifuge*, Fits in. Stands out., at least as early as Mar. 1, 2017, pp. 6.

Thermo Fisher Scientific, Inc., *Nunc Cell Factory Systems*, 2016, pp. 2.

Thermo Fisher Scientific, Inc., *Large Capacity Rotors, Thermo Scientific 6×2000 mL Swinging Bucket Rotor*, 2016, pp. 2.

Sartorius Stedim Biotech, *kSep Systems, Advanced Scalable, Single-Use Automated Centrifugation Systems*, https:///www.sartorius.com/ sartorius/en/EUR/ksep-systems, 2017, pp. 4.

International Search Report and Written Opinion dated Jun. 19, 2019, issued in PCT Application No. PCT/IB2019/051639, filed Feb. 28, 2019.

* cited by examiner

SINGLE-USE CENTRIFUGE CONTAINERS FOR SEPARATING BIOLOGICAL SUSPENSIONS AND METHODS OF USE

CROSS-REFERENCE TO RELATED APPLICATIONS

This application claims the benefit of Provisional Application No. 62/637,561, filed Mar. 2, 2018, which is incorporated herein by specific reference.

BACKGROUND

1. The Field of the Disclosure

The present disclosure relates to methods for centrifugally separating biologic suspensions using single-use, flexible containers and further relates to corresponding systems and container assemblies.

2. The Relevant Technology

Bioreactors and fermenters are used to grow a variety of different types of biological suspensions. Such suspensions are broadly defined as comprising cells or microorganisms and a liquid medium in which they are suspended. Once a suspension has been sufficiently grown, it is common to separate the biological suspension into components and then harvest the separate components for subsequent analysis or use. Centrifugation is a technique often employed during isolation or analysis of various cells, organelles, and biopolymers, including proteins, nucleic acids, lipids, and carbohydrates dissolved or dispersed in biological suspension.

In one approach to centrifugation, quantities of a suspension are dispensed from a bioreactor or fermenter into an open-top bottle. The bottle is then closed by manually applying a lid and then spun using a centrifuge rotor. The centrifugal force created by spinning of the rotor causes the solids within the suspension to sediment out of the solution to form a generally solid pellet towards the bottom of the bottle. A supernatant, which is a liquid that is less dense than the pellet, collects within the bottle above the pellet. The supernatant is then decanted from the bottle by removing the lid and then pouring and/or pumping out the supernatant. The pellet can then be separately removed from the bottle.

Although the above process is effective, it has a number of shortcomings. For example, in the above process the bottles are reused. Accordingly, after each use it is necessary to clean and sterilize each bottle. This process is time consuming, labor intensive and requires special sterilizing equipment, like an autoclave. Furthermore, although the bottles are cleaned and sterilized between each use, the bottles are used as open-top containers. Thus, both the suspension and the interior of the bottles are openly exposed to the surrounding environment as the suspension is initially dispensed into the bottles. In turn, the separated components are again openly exposed to the surrounding environment as the separated components are removed from the bottles. This open exposure to the environment increases the probability of the suspension and/or the separated components becoming contaminated. Subsequent purification steps can thus be required to remove any contaminates from one or both of the separated components. Conventional methods and systems thus have a high probability of contamination and can require added labor, time, and cost to run purification steps.

In addition to the above, it can be difficult in conventional systems to effectively separate the supernatant from the pellet. That is, it is typically desirable to maximize the quantity of cells or microorganism within the pellet and to minimize the quantity of cells or microorganism within the supernatant. However, in some applications the pellet can be easily disturbed causing the solids thereof to resuspend into the supernatant. As such, it can be a slow and labor intensive process to carefully decant the supernatant from the bottles without disturbing the pellet. It is often necessary to sacrifice some supernatant to avoid disturbing the pellet.

In one attempt to solve some of the above problems, a removable, open-top liner has been placed within a centrifuge container. The liner bounds the compartment of the container and receives the biological suspension. Following use, the liner is discarded and a new liner can be inserted within the centrifuge container without the need for cleaning or sterilization of the container. Although use of the liner minimizes the cleaning requirement, the liner, like the above discussed bottle, is open and exposed to the surrounding environment during dispensing of the biological suspension therein. As such, there remains an increased risk of the suspension and components being contaminated and the need for purification steps. Furthermore, the liner does not solve the difficulty of separating the supernatant from the pellet. Other shortcomings also exist.

Accordingly, what is needed in the art are improved methods, systems, and containers that solve all or some of the above and other existing shortcomings.

SUMMARY OF THE DISCLOSURE

In a first independent aspect of the present disclosure, a method for separating a biological suspension includes:
  dispensing a liquid suspension comprised of cells or microorganisms into a sterile compartment of a first bag assembly, the first bag assembly comprising a collapsible bag comprised of one or more sheets of flexible film; and
  rotating the first bag assembly using a centrifuge so that the liquid suspension separates within the compartment into a pellet comprised of the cells or microorganisms and a liquid supernatant.

In one embodiment, the liquid suspension is dispensed into the compartment of the first bag assembly through a sterile pathway.

In another embodiment, the liquid suspension is dispensed from a bioreactor or fermenter to the compartment of the first bag assembly through a closed, sterile pathway.

Another embodiment includes:
  sealing the compartment of the first bag assembly closed; and
  placing the sealed first bag assembly within a cavity of a rotor of the centrifuge.

In another embodiment, the first bag assembly is placed so that the first bag assembly sits directly on an interior surface of the cavity of the rotor.

In another embodiment, the step of placing comprises:
  positioning the first bag assembly within a cavity of an insert; and
  placing the insert within the cavity of the rotor.

In another embodiment, the insert is sufficiently flexible that the cavity of the insert can be completely collapsed without plastic deformation of the insert.

In another embodiment, the insert has a thickness extending between an interior surface and an exterior surface, the insert being sufficiently flexible that the thickness can be manually compressed between the fingers of an operator.

In another embodiment, the insert has a thickness extending between an interior surface and an exterior surface, the insert being sufficiently rigid that the thickness cannot be manually compressed between the fingers of an operator.

In another embodiment, the insert has a maximum thickness that is less than 0.5 cm.

In another embodiment, the cavity of the insert is elongated.

In another embodiment, the cavity of the rotor has an opening that is oval or elliptical.

In another embodiment, the cavity of the insert has a lower end that inwardly tapers.

In another embodiment, the cavity of the insert inwardly tapers along both a length of the cavity and along a width of the cavity at the lower end.

In another embodiment, after the insert is placed with the cavity of the rotor, the insert has an annular lip portion that freely projects out of the cavity of the rotor by a distance of at least 0.5 cm, 1 cm, or 2 cm, In another embodiment, the rotor comprises a swinging-bucket rotor and the cavity is formed on a bucket of the swinging bucket rotor.

In another embodiment, the rotor comprises a fixed angle rotor and the cavity is formed in the rotor at an angle to the vertical.

In another embodiment, the cavity of the rotor is elongated and has a lower end that inwardly tapers.

In another embodiment, the cavity of the rotor has an opening that is oval or elliptical.

In another embodiment, the first bag assembly has an upper end with one or more tubes or ports coupled thereto and an opposing lower end, the lower end being more inwardly tapered than the upper end.

In another embodiment, the first bag assembly comprises a first sheet of flexible film overlapping and being secured to a second sheet of flexible film, the compartment being bounded between the first sheet and the second sheet, a first port being secured to and passing through the first sheet so as to communicate with the compartment.

Another embodiment further comprises transferring at least a portion of the liquid supernatant from the compartment of the first bag assembly into a separate container through a sterile pathway while the pellet is retained within the compartment of the first bag assembly.

Another embodiment further comprises storing the first bag assembly having the pellet therein within a freezer after transferring the at least a portion of the liquid supernatant from the compartment.

Another embodiment includes:
dispensing a liquid into the compartment of the first bag assembly after transferring the at least a portion of the liquid supernatant from the compartment; and
mixing the liquid with the pellet to form a secondary suspension.

In another embodiment, the step of mixing comprises manually manipulating the pellet through the first bag assembly so as to break up the pellet.

Another embodiment includes storing the first bag assembly having the secondary suspension therein within a freezer.

Another embodiment includes:
rotating the first bag assembly containing the secondary suspension using a centrifuge to separate the secondary suspension into a secondary pellet and a secondary supernatant; and
transferring at least a portion of the secondary supernatant from the compartment of the first bag assembly into a separate container while the secondary pellet is retained within the compartment of the first bag assembly.

In another embodiment, wherein the step of transferring at least a portion of the liquid supernatant comprises a pump is used to pump the at least a portion of the liquid supernatant into the separate container.

In another embodiment, the step of transferring at least a portion of the liquid supernatant comprises using an expressor to compress at least a portion of the first bag assembly so as to drive the at least a portion of the liquid supernatant into the separate container.

In another embodiment, the pellet has a greater density or viscosity than the liquid supernatant.

Another embodiment includes:
forming a seal across the first bag assembly so as to separate the compartment of the first bag assembly into an upper compartment that houses at least a portion of the supernatant and a lower compartment that houses the pellet, the upper compartment being sealed closed from the lower compartment; and
transferring at least a portion of the supernatant in the upper compartment into a separate container.

In another embodiment, the step of forming a seal comprises applying a clamp across the first bag assembly.

In another embodiment the step of forming a seal comprises applying an expressor to the first bag assembly.

Another embodiment includes:
removing the seal from across the first bag assembly;
delivering a liquid into the compartment of the first bag assembly; and
mixing the pellet with the liquid to form a secondary suspension.

In another embodiment, the step of dispensing the liquid suspension comprises passing the liquid suspension through a manifold and into the sterile compartment of the first bag assembly, the manifold being fluid coupled with first bag assembly and a second bag assembly.

Another embodiment includes:
sealing the compartment of the first bag assembly closed;
separating the first bag assembly from the manifold; and
placing the separated first bag assembly within a cavity of a rotor of the centrifuge.

Another embodiment includes:
placing the first bag assembly within a first cavity of a rotor of the centrifuge;
placing the second bag assembly within a second cavity of the rotor of the centrifuge, the manifold being fluid coupled with the first bag assembly and the second bag assembly; and
the step of rotating comprising rotating the first bag assembly, the second bag assembly and the manifold using the centrifuge.

In another embodiment, the step of placing the first bag assembly within the first cavity of the rotor comprises inserting the first bag assembly within the cavity of an insert and then placing the insert with the first cavity of the rotor.

Another embodiment includes:
removing the first bag assembly, the second bag assembly and the manifold from the rotor;
fluid coupling the manifold to a container; and
dispensing at least a portion of the supernatant from the first bag assembly to the container through the manifold while the pellet is retained within the compartment of the first bag assembly.

Another embodiment includes:
decoupling the manifold from the container;
delivering a liquid into the compartment of the first bag assembly through the manifold; and
mixing the pellet with the liquid to form a secondary suspension within the first bag assembly.

In a second independent aspect of the present disclosure, a method for separating a biological includes:
dispensing a liquid suspension comprised of cells or microorganisms through a manifold and into a compartment of each of a plurality of bag assemblies that are each fluid coupled with the manifold, each of the plurality of bag assemblies comprising a collapsible bag comprised of one or more sheets of flexible film;
separating each of the plurality of bag assemblies from the manifold so that the compartment of each of the plurality of collapsible bags is sealed closed;
placing each of the plurality of bag assemblies into a cavity of a rotor of a centrifuge; and
activating the centrifuge so that the liquid suspension within the compartment of each of the plurality of bag assemblies separates into a pellet comprised of the cells or microorganisms and a liquid supernatant.

In one embodiment, the step of placing comprises inserting each of the plurality of bag assembly within the cavity of a corresponding insert and then placing each insert with a corresponding cavity of the rotor.

In another embodiment, the compartment of each of the plurality of collapsible bag assemblies is sterile as the suspension is first dispensed into the compartments.

In another embodiment, the step of placing each of the plurality of bag assemblies onto a rotor comprising placing each of the plurality of bag assemblies into a separate bucket of a swinging-bucket rotor.

In another embodiment, the step of dispensing the liquid suspension comprises passing the liquid suspension from the manifold to each of the plurality of bag assemblies so that the liquid suspension within each of the plurality of bag assemblies is free of contaminates.

Another embodiment includes:
fluid coupling one of the plurality of bag assemblies to a container using a sterile connection; and
transferring at least a portion of the liquid supernatant from the one of the plurality of bag assemblies to the container through the fluid coupling while the pellet is retained within the compartment of the one of the plurality of bag assemblies.

Another embodiment includes:
applying a clamp across a one of the plurality of bag assemblies so that the compartment of the one of the bag assemblies is divided into an upper compartment in which at least a portion of the supernatant is disposed and a lower compartment in which the pellet is disposed, the upper compartment being sealed closed from the lower compartment by the clamp; and
removing at least a portion of the supernatant from the upper compartment while the clamp is applied to the one of the plurality of bag assemblies.

In a third independent aspect of the present disclosure, a method for separating a biological suspension includes:
rotating a bag assembly so that a liquid suspension within a compartment of the bag assembly separates into a pellet comprised of cells or microorganisms and a liquid supernatant, the bag assembly comprising a collapsible bag comprised of one or more sheets of flexible film;
forming a seal across the bag assembly so that the compartment of the bag assembly is divided into an upper compartment in which at least a portion of the liquid supernatant is disposed and a lower compartment in which the pellet is disposed, the upper compartment being sealed closed from the lower; and
removing at least a portion of the liquid supernatant from the upper compartment while the seal is formed.

In one embodiment, the bag assembly is rotated using a centrifuge.

In another embodiment, the step of forming the seal comprises applying a clamp across the bag assembly.

In another embodiment, the step of forming the seal comprises applying an expressor or the bag assembly.

In another embodiment, the step of forming the seal comprises forming a weld across the bag assembly.

In another embodiment, the step of removing at least a portion of the liquid supernatant comprises:
forming a sterile fluid coupling between the bag assembly and a container; and
pumping the at least a portion of the liquid supernatant from the upper compartment to the container through the sterile fluid coupling.

In another embodiment, the step of removing at least a portion of the liquid supernatant comprises:
using a pump to pump the at least a portion of the liquid supernatant into a separate container; or
using an expressor to compress at least a portion of the bag assembly so as to drive the at least a portion of the liquid supernatant into a separate container.

Another embodiment includes:
removing the seal from across the bag assembly;
delivering a liquid into the compartment of the bag assembly; and
mixing the pellet with the liquid to form a secondary suspension.

Another embodiment includes storing the bag assembly having the secondary suspension therein within a freezer.

Another embodiment includes storing the bag assembly having the pellet therein within a freezer after removing at least a portion of the liquid supernatant from the upper compartment.

In a fourth independent aspect of the present disclosure, a method for separating a biological includes:
dispensing a liquid suspension comprised of cells or microorganisms through a manifold and into a compartment of each of a plurality of bag assemblies that are each fluid coupled with the manifold, each of the plurality of bag assemblies comprising a collapsible bag comprised of one or more sheets of flexible film;
placing each of the plurality of bag assemblies fluid coupled with the manifold into a corresponding separate cavity of a rotor of a centrifuge; and
activating the centrifuge so that the liquid suspension within the compartment of each of the plurality of bag assemblies fluid coupled with the manifold separates into a pellet comprised of the cells or microorganisms and a liquid supernatant.

In one embodiment, the step of placing each of the plurality of bag assemblies comprises inserting each bag assembly into a cavity of a corresponding separate insert and then placing each insert with the corresponding separate cavity of the rotor.

Another embodiment includes:
fluid coupling the manifold to a container; and
dispensing at least a portion of the supernatant from a first bag assembly of the plurality of bag assemblies into the container through the manifold while the pellet of the first bag assembly is retained within the compartment of the first bag assembly.

Another embodiment includes removing the plurality of bag assemblies and the manifold from the rotor prior to dispensing the at least a portion of the supernatant from the first bag assembly.

Another embodiment further includes:
decoupling the manifold from the container;
delivering a liquid into the compartment of the first bag assembly through the manifold; and
mixing the pellet within the first bag assembly with the liquid to form a secondary suspension within the first bag assembly.

In a fifth independent aspect of the present disclosure, a single use centrifuge bag assembly includes:
a first sheet of a flexible polymeric film;
a second sheet of a flexible polymeric film overlaying the first sheet, the first sheet and the second sheet extending between an upper end and an opposing lower end;
a first port or tube being secured to the first sheet or the second sheet upper end;
a seam line securing the first sheet to the second sheet and encircling a compartment bounded between the first sheet and the second sheet, the seam line having a length and comprising:
a top seam line section disposed at the upper end; and
a bottom seam line section that is disposed opposite the top seam line section, the bottom seam line section having an inner edge facing the compartment that is in the shape of a smooth continuous curve comprising at least 25% the length of the seam line that encircles the compartment.

In one embodiment, the inner edge of the bottom seam line section is in the form of a semi-circle or a section of an oval.

In another embodiment, the seam line further comprises a pair of opposing side seam lines disposed between the top seam line and the bottom seam line, wherein each side seam line has an inside edge facing the compartment that is linear, the bottom seam line extending between the pair of opposing side seam lines.

In another embodiment, the first tube or port either passes through and is secured to the first sheet or is secured between the first sheet and the second sheet.

In a sixth independent aspect of the present disclosure, an assembly includes:
a collapsible bag bounding a compartment and being comprised of one or more sheets of flexible film, the collapsible bag having an upper end with one or more tubes or ports coupled thereto and an opposing lower end, the lower end being more inwardly tapered than the upper end; and
a rotor of a centrifuge having an elongated cavity with an upper end and an opposing lower end, the lower end being inwardly tapered, the collapsible bag being disposed within the cavity of the rotor.

In one embodiment, the collapsible bag is directly disposed within the cavity of the rotor.

Another embodiment includes an insert having an elongated cavity with an upper end and an opposing lower end, the lower end being inwardly tapered, the insert being disposed within the cavity of the rotor and the collapsible bag being disposed within the cavity of the insert.

In another embodiment, with the insert fully disposed within the cavity of the rotor, the insert has an annular lip portion that freely projects out of the cavity of the rotor by a distance of at least 0.5 cm, 1 cm, or 2 cm.

In a seventh independent aspect of the present disclosure, a single use centrifuge bag assembly includes:
a collapsible bag bounding a compartment and being comprised of one or more sheets of flexible film; and
a seal formed across the collapsible bag so that the compartment of the bag is divided into an upper compartment in which a liquid supernatant is disposed and a lower compartment in which a pellet is disposed, the pellet being comprised of cells or microorganisms, the upper compartment being sealed closed from the lower.

In one embodiment, the seal includes a clamp removably mounted on the collapsible bag.

In another embodiment, the pellet has a greater density or viscosity than the liquid supernatant.

Each of the above independent aspects of the disclosure may include any of the features, options and possibilities set out in this document, including those under the other independent aspects, and may also include any combination of any of the features, options and possibilities set out in this document.

BRIEF DESCRIPTION OF THE DRAWINGS

Various embodiments of the present disclosure will now be discussed with reference to the appended drawings. It is appreciated that these drawings depict only typical embodiments of the disclosure and are therefore not to be considered limiting of its scope.

DETAILED DESCRIPTION OF THE PREFERRED EMBODIMENTS

Figure 1:
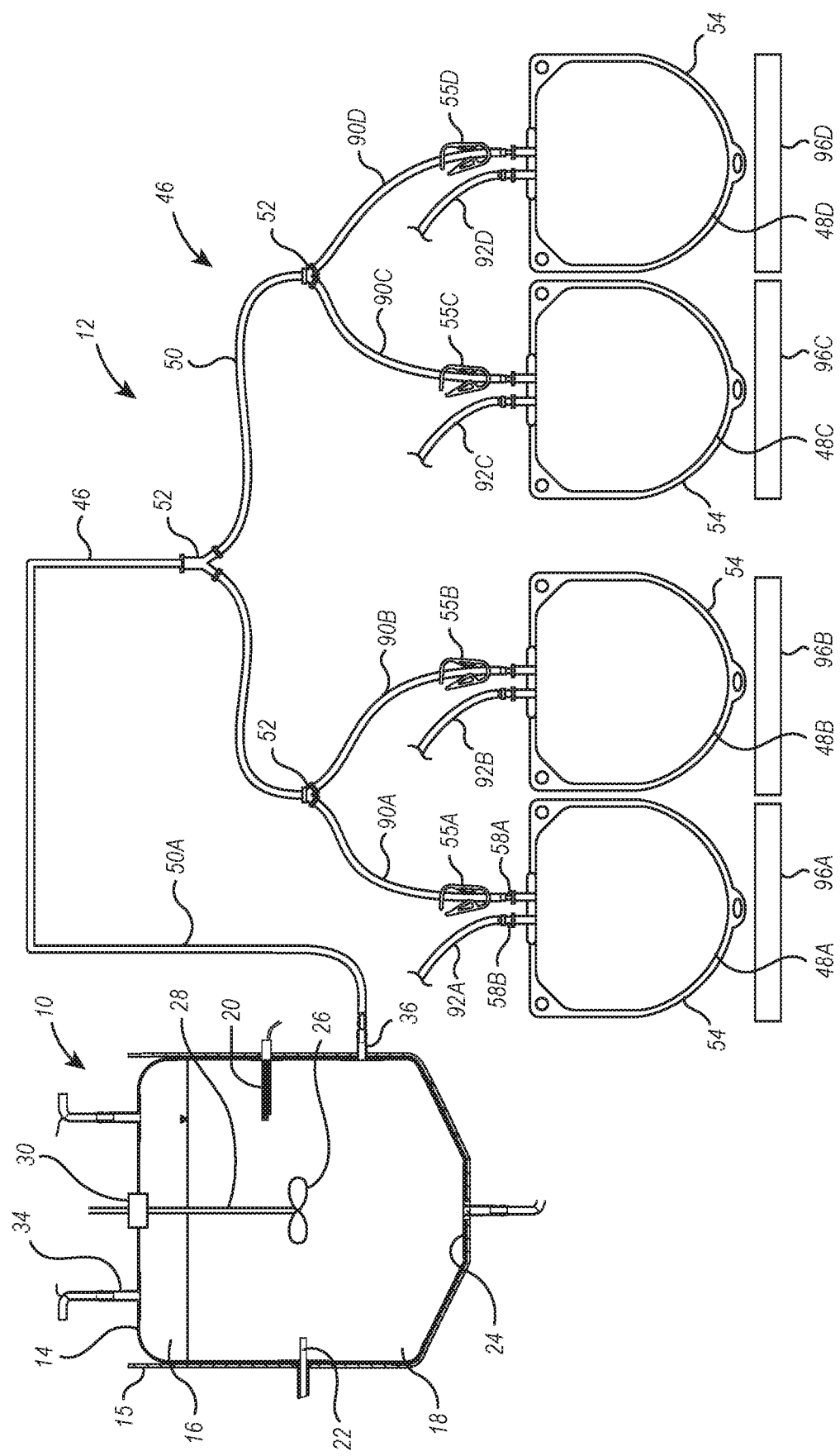
FIG. 1 is an elevated front view of a reactor that is fluid coupled with a manifold system.

Before describing the present disclosure in detail, it is to be understood that this disclosure is not limited to particularly exemplified apparatus, systems, methods, or process parameters that may, of course, vary. It is also to be understood that the terminology used herein is only for the purpose of describing particular embodiments of the present disclosure and is not intended to limit the scope of the disclosure in any manner.

All publications, patents, and patent applications cited herein, whether supra or infra, are hereby incorporated by reference in their entirety to the same extent as if each individual publication, patent, or patent application was specifically and individually indicated to be incorporated by reference.

The term "comprising" which is synonymous with "including," "containing," or "characterized by," is inclusive or open-ended and does not exclude additional, unrecited elements or method steps.

It will be noted that, as used in this specification and the appended claims, the singular forms "a," "an" and "the" include plural referents unless the content clearly dictates otherwise. Thus, for example, reference to a "port" includes one, two, or more ports.

As used in the specification and appended claims, directional terms, such as "top," "bottom," "left," "right," "up," "down," "upper," "lower," "proximal," "distal" and the like are used herein solely to indicate relative directions and are not otherwise intended to limit the scope of the disclosure or claims.

Where possible, like numbering of elements have been used in various figures. Furthermore, multiple instances of an element and or sub-elements of a parent element may each include separate letters appended to the element number. For example, two instances of a particular element "10" may be labeled as "10A" and "10B". In that case, the element label may be used without an appended letter (e.g., "10") to generally refer to all instances of the element or any one of the elements. Element labels including an appended letter (e.g., "10A") can be used to refer to a specific instance of the element or to distinguish or draw attention to multiple uses of the element. Furthermore, an element label with an appended letter can be used to designate an alternative design, structure, function, implementation, and/or embodiment of an element or feature without an appended letter. Likewise, an element label with an appended letter can be used to indicate a sub-element of a parent element. For instance, an element "12" can comprise sub-elements "12A" and "12B."

Various aspects of the present devices and systems may be illustrated by describing components that are coupled, attached, and/or joined together. As used herein, the terms "coupled", "attached", and/or "joined" are used to indicate either a direct connection between two components or, where appropriate, an indirect connection to one another through intervening or intermediate components. In contrast, when a component is referred to as being "directly coupled", "directly attached", and/or "directly joined" to another component, there are no intervening elements present. Furthermore, as used herein, the terms "connection," "connected," and the like do not necessarily imply direct contact between the two or more elements.

Various aspects of the present devices, systems, and methods may be illustrated with reference to one or more exemplary embodiments. As used herein, the term "embodiment" means "serving as an example, instance, or illustration," and should not necessarily be construed as preferred or advantageous over other embodiments disclosed herein.

Unless defined otherwise, all technical and scientific terms used herein have the same meaning as commonly understood by one of ordinary skill in the art to which the present disclosure pertains. Although a number of methods and materials similar or equivalent to those described herein can be used in the practice of the present disclosure, the preferred materials and methods are described herein.

In general, the present disclosure relates to methods, systems and bag assemblies for separating and harvesting components of biological suspensions. More specifically, the present disclosure relates to single-use manifolds and bag assemblies for use in centrifugally separating biological suspensions, for harvesting the components of such suspensions, and relates to corresponding methods. Depicted in FIG. 1 is one embodiment of a reactor 10 fluid coupled with a manifold system 12 incorporating features of the present disclosure. Reactor 10 is configured for growing a biological suspension and can comprise a bioreactor, fermenter, or any other device designed for growing or producing biological suspensions. The term "bioreactor" as used herein is broadly intended to cover multi-plate growth chambers such as the Cell Factory multi-plate growth chamber produced by Thermo Fisher Scientific. It is also appreciated that reactor 10 can comprise any conventional type of bioreactor or fermenter such as a stirred-tank reactor, rocker type reactor, paddle mixer reactor, or the like.

In the embodiment depicted, reactor 10 comprises a container 14 bounding a chamber 16. Container 14 is supported by a rigid support housing 15. Disposed within chamber 16 is a liquid suspension 18. Suspension 18 typically comprises a biological suspension that includes cells or microorganisms and a growth medium in which the cells or microorganisms are suspended and grown. By way of example and not by limitation, the reactor 10 can be used in culturing bacteria, fungi, algae, plant cells, animal cells, protozoans, nematodes, and the like. Examples of some common biologics that are grown include *E. coli*, yeast, bacillus, and CHO cells. Reactor 10 can accommodate cells and microorganisms that are aerobic or anaerobic and are adherent or non-adherent. The composition for the medium is known in the art and changes based upon the cells or microorganisms being grown and the desired end product. In some uses, reactor 10 is used primarily only to grow and recover cells for subsequent use (e.g., preparing vaccine materials from the cells themselves). However, in many uses, the ultimate purpose of growing cells in reactor 10 is to produce and later recover biological products (such as recombinant proteins) that are exported from the cells into the growth medium. It is also common to use reactor 10 to grow cells in a master batch to prepare aliquots of cells for subsequent use as an inoculant for multiple subsequent batches of cells grown to recover biological products.

Although the disclosure disclosed herein is primarily designed for use with biological suspensions, the apparatus and methods of the present disclosure can also be used with non-biological suspensions where it is desired to separate solids from liquids using a centrifuge. Such applications can be found in the production of chemicals, medicines, and other products. Accordingly, the discussions and examples set forth herein of separating a biological suspension and harvesting the separated components are also applicable to and should be considered as disclosure for separating non-biological suspensions and harvesting the separated components thereof.

In one embodiment, container 14 comprises a flexible, collapsible bag. For example, container 14 can be comprised of one or more sheets of a flexible, water impermeable polymeric film such as a low-density polyethylene. The polymeric film can have a thickness that is at least or less than 0.02 mm, 0.05 mm, 0.1 mm, 0.2 mm, 0.5 mm, 1 mm, 2 mm, 3 mm or is in a range between any two of the foregoing values. Other thicknesses can also be used. The film is sufficiently flexible that it can be rolled into a tube without plastic deformation and can be folded over an angle of at least 90°, 180°, 270°, or 360° without plastic deformation.

The film can be comprised of a single ply material or can comprise at least two or more layers that are either sealed together or separated to form a double wall container. Where the layers are sealed together, the material can comprise a laminated or extruded material. The laminated material comprises two or more separately formed layers that are subsequently secured together by an adhesive. One example of an extruded material that can be used in the present disclosure is the Thermo Scientific CX3-9 film available from Thermo Fisher Scientific. The Thermo Scientific CX3-9 film is a three-layer, 9 mil cast film produced in a cGMP facility. The outer layer is a polyester elastomer coextruded with an ultra-low density polyethylene product contact layer. Another example of an extruded material that can be used in the present disclosure is the Thermo Scientific CX5-14 cast film also available from Thermo Fisher Scientific. The Thermo Scientific CX5-14 cast film comprises a polyester elastomer outer layer, an ultra-low density polyethylene contact layer, and an EVOH barrier layer disposed therebetween.

The material can be approved for direct contact with living cells and be capable of maintaining a solution sterile. In such an embodiment, the material can also be sterilizable such as by ionizing radiation. Examples of materials that can be used in different situations are disclosed in U.S. Pat. No. 6,083,587 which issued on Jul. 4, 2000 and United States Patent Publication No. US 2003-0077466 A1, published Apr. 24, 2003, which are hereby incorporated by specific reference.

In one embodiment, container 14 comprise a two-dimensional pillow style bag wherein two sheets of material are placed in overlapping relation and the two sheets are bounded together at their peripheries to form chamber 16. Alternatively, a single sheet of material can be folded over and seamed around the periphery to form the internal compartment. In another embodiment, container 14 can be formed from a continuous tubular extrusion of polymeric material that is cut to length and is seamed closed at the ends. In still other embodiments, container 14 can comprise a three-dimensional bag that not only has an annular side wall but also a two dimensional top end wall and a two dimensional bottom end wall.

It is appreciated that container 14 can be manufactured to have virtually any desired size, shape, and configuration. For example, container 14 can be formed having a compartment sized to 5 liters, 10 liters, 30 liters, 50 liters, 100 liters, 250 liters, 500 liters, 750 liters, 1,000 liters, 1,500 liters, 3,000 liters, 5,000 liters, 10,000 liters or other desired volumes. The size of chamber 16 can also be in the range between any two of the above volumes. Although in the above discussed embodiment container 14 has a flexible, bag-like configuration, in alternative embodiments it is appreciated that container 14 can comprise any form of collapsible container or semi-rigid container. In some embodiments, container 14 can comprise a rigid container, such as comprised of metal (such as stainless steel), molded plastic or a composite. In this embodiment, support housing 15 can be eliminated, as container 14 is self-supporting.

As needed, sensors 20 and probes 22 can be coupled with container 14 for detecting properties of suspension 18. By way of example and not by limitations, sensors 20 and probes 22 can comprise temperature probes, pH probes, $CO_2$ sensors, oxygen sensors, pressure sensors, and the like. If needed, a sparger 24 can be coupled with container 14 for delivering gas to suspension 18 within chamber 16.

In one embodiment of the present disclosure, means are provided for mixing suspension 18 within container 14. In the depicted embodiment, an impeller 26 is disposed within chamber 16 and is coupled with a drive shaft 28. Drive shaft 28 couples with container 14 through a dynamic seal 30. A motor can be coupled with drive shaft 28 for rotating impeller 26 to facilitate mixing of suspension 18.

In another embodiment, drive shaft 28 can project into container 14 through a flexible tube having one end rotatably connected to container 14 and an opposing second end connected to impeller 26. Drive shaft 28 passes through the flexible tube and removably couples with impeller 26 so that drive shaft 28 can rotate impeller 26 without directly contacting suspension 18. Examples of this mixing system are disclosed in U.S. Pat. No. 7,384,783, issued Jun. 10, 2008 and U.S. Pat. No. 7,682,067, issued Mar. 23, 2010 which are incorporated herein by specific reference. In another alternative embodiment, drive shaft 28 can be configured to repeatedly rise and lower a mixing element located within container 14 for mixing the fluid. Alternatively, a magnetic stir bar or impeller can be disposed within chamber 16 of container 14 and rotated by a magnetic mixer disposed outside of container 14. In yet other embodiments, a stir bar, paddle, or the like that projects into chamber 16 of container 14 can be pivoted, swirled, shook or otherwise moved to mix suspension 18. In addition, the mixing can be accomplished by circulating fluid through chamber 16, such as by using a peristaltic pump to move the fluid into and out of chamber 16 through a tube having opposing ends sealed to container 14. Gas bubbles can also be passed through suspension 18 to achieve the desired mixing. Finally, support housing 15 and container 14 can be pivoted, rocked, rotated or otherwise moved so as to mix suspension 18 within container 14. Other conventional mixing techniques can also be used. Specific examples of how to incorporate a mixer into a flexible bag, such as container 14, are disclosed in U.S. Pat. No. 7,384,783, issued Jun. 10, 2008; U.S. Pat. No. 7,682,067, issued Mar. 23, 2010; and US Patent Publication No. 2006/0196501, issued Sep. 7, 2006 which are incorporated herein by specific reference.

A plurality of ports 34 are coupled with container 14 for delivering material into or removing material from chamber 16. A port 36 is disposed at a lower end of container 14 and is fluid coupled with manifold system 12. In general, manifold system 12 comprises a manifold 46 fluid coupled to a plurality of bag assemblies 48A, 48B, 48C, and 48D. In one embodiment, manifold 46 comprises a plurality of separate sections of fluid line 50, such as flexible tubing, that are coupled together by fittings 52, such as Y-connectors, so that fluid exiting from port 36 can be delivered to each of bag assemblies 48 along sterile pathways. It is noted that reactor 10 is not drawn to scale with regard to bag assemblies 48. Chamber 14 of reactor 10 will commonly have a fluid capacity that is at least 3, 5, 10, 20, 50, 100, 200 or more times the fluid capacity of a single bag assembly 48.

Figure 2:
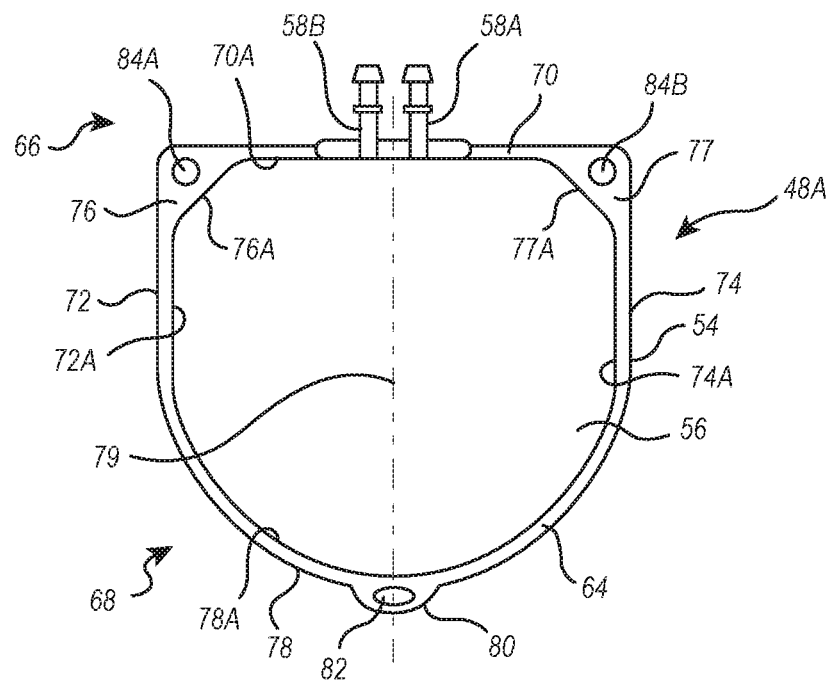
FIG. 2 is an elevated front view of a bag assembly of the manifold system shown in FIG. 1
Figure 3:
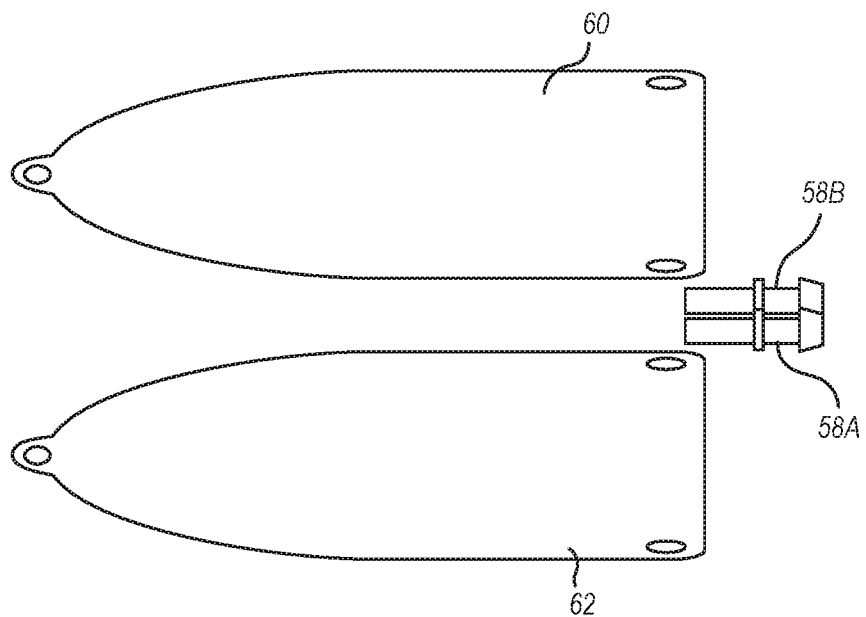
FIG. 3 is an exploded view of the bag assembly shown in FIG. 2.

As depicted in FIG. 2, bag assembly 48A comprises a flexible, collapsible bag 54 bounding a compartment 56. Bag assembly 48A further comprises a first port 58A and a second port 58B coupled to bag 54 and communicating with compartment 56. As depicted in FIG. 3, bag 54 is comprised of a first sheet 60 overlying a second sheet 62. Sheets 60 and 62 are bonded together (as shown in FIG. 2) to form a seam line 64 that encircles compartment 56. Seam line 64 can be produced by using conventional welding techniques such as heat welding, RF energy, ultrasonic, and the like. Other conventional techniques, such as by using an adhesive, can also be used to form seam line 64. Ports 58A and 58B are bonded between sheets 60 and 62 so as to form a sealed engagement therebetween. Ports 58A and 58B can also be bonded to sheets 60 and 62 by welding, adhesive or other conventional techniques. Although two ports 58A and 58B are shown, other numbers of ports, such as one, three, four or more ports, could be secured between sheets 60 and 62 so as to communicate with compartment 56. In other embodiments, as discussed below in more detail, ports 58A and 58B could be eliminated and one, two, three or more sections of tubing could be secured between sheets 60 and 62 so as to communicate with compartment 56.

First sheet 60 and second sheet 62 can be made of the same materials and have the same properties as the materials previously discussed with regard to container 14. For example, each of sheets 60 and 62 can comprise a flexible, water impermeable polymeric film such as a low-density polyethylene. The polymeric film can have a thickness that is at least or less than 0.02 mm, 0.05 mm, 0.1 mm, 0.2 mm, 0.5 mm, 1 mm, 2 mm, 3 mm or in a range between any two of the foregoing. Other thicknesses can also be used. The film is sufficiently flexible that it can be rolled into a tube without plastic deformation and can be folded over an angle of at least 90°, 180°, 270°, or 360° without plastic deformation.

The film can be comprised of a single ply material or can comprise at least two, three, four or more layers that are either sealed together or separated to form a multi-wall container. Where the layers are sealed together, the material can comprise a laminated or extruded material. The laminated material comprises two or more separately formed layers that are subsequently secured together by an adhesive. One example of an extruded material that can be used in the present disclosure is the Thermo Scientific CX3-9 film available from Thermo Fisher Scientific. The Thermo Scientific CX3-9 film is a three-layer, 9 mil cast film produced in a cGMP facility. Although Sheets 60 and 62 can also be formed of the five-layer cast film CX5-14, previously discussed, more favorable results have been obtained by forming bag 54 from a three layer film. This is because bags 54 formed from a three layer film are more flexible than bags 54 formed from a five layer film and, as a result, produce fewer creases or folds during centrifugation. As discussed below in greater detail, such creases or folds can have a negative influence during centrifugation. Accordingly, sheets 60 and 62 are commonly formed from extruded or laminated films having between 2-4 layers and, more commonly three layers and having a thickness between 7 mil and 11 mil and more commonly between 8 mil and 10 mil.

Bags 54 are commonly sized so that compartment 56, when and if inflated, has a volume of at least or less than 0.5 liters, 1 liter, 1.5 liters, 2 liters, 2.5 liters, 3 liters, 5 liters, or in a range between any two of the foregoing values. Other volumes can also be used.

Returning to FIG. 2, bag 54 has a top end 66 where ports 58 are disposed and an opposing bottom end 68. Seam line 64 comprises a top seam line section 70 disposed at top end 66 to which ports 58A and 58B are connected and which has an linear inner edge 70A. Seam line 64 also includes opposing side seam line sections 72 and 74 that include linear inner edges 72A and 74A, respectively, that are perpendicular to inner edge 70A. A corner seam line section 76 extends at an angle between top seam line section 70 and side seam line section 72 having a linear inner edge 76A while a corner seam line section 77 extends between top seam line section 70 and side seam line section 74 having a linear inner edge 77A. Inner edges 76A and 77A intersect with inner edge 70A to each form an inside angle therebetween that is in a range between 110° and 170° with between 130° and 150° being more common. Other angles can also be used. In other embodiments corner seam line sections 76 and 77 can be configured to that inner edges 76A and 77A are curved. In yet other embodiments, corner seam line sections 76 and 77 can be eliminated and top seam line section 70 can intersect directly with side seam line sections 72 and 74.

Finally, seam line 64 also includes a bottom seam line section 78 disposed at bottom end 68 that has an inner edge 78A that arches away from top seam line section 70 and that extends as a smooth continuous curve between opposing side seam line sections 72 and 74. The curve of bottom seam line section 78 can be an arc, U-shape, segment of an oval, segment of an ellipse, or have other configurations. In one embodiment, bottom seam section line 78 comprises at least 20%, 25%, 30%, 35%, or 40% of the entire length of seam line 64 that encircles compartment 56. As depicted and in view of the foregoing, it is appreciated that top end 66 and bottom end 68 of bag 54, and particularly the seam lines thereat, have different configuration, i.e., they are not symmetrical about a lateral axis that extends between side seam line section 72 and 74.

More specifically, with regard to a central longitudinal axis 79 that extends between top seam line section 70 and bottom seam line section 78, compartment 56 is more constricted about central longitudinal axis 79, i.e., compartment 56 is narrower, at bottom end 68 than at top end 66. The constricting of compartment 56 at bottom end 68 functions to help consolidate the pellet produced during centrifugation, as discussed below, at a central location within compartment 56. Consolidating the pellet in a constricted area makes the pellet thicker with more mass so that the pellet is more stable and less likely to break apart. Consolidating the pellet into a constricted area also assists with the removal of the supernatant and can assist with subsequent removal of the pellet that is located in a smaller area. Although inwardly tapering bottom end 68 of bag 54 achieves the above discussed added benefits, in other embodiments bag 54 could be formed so that bottom end 68 does not taper or does not taper more than top end 66. That is, top end 66 and bottom end 68 of bag 54, and particularly the seam lines thereat, could be symmetrical about a lateral axis that extends between side seam line section 72 and 74.

Bag 54 further comprises a hanging tab 80 centrally formed at bottom end 68 with an opening 82 extended therethrough. Openings 84A and 84B also extend through sheets 60 and 62, such as through seam line 64, at opposing sides of bag 54 at top end 66. Openings 82 and 84 can be used for hanging or supporting each bag assembly 48 in a vertically up orientation or vertically down orientation.

Figure 4:
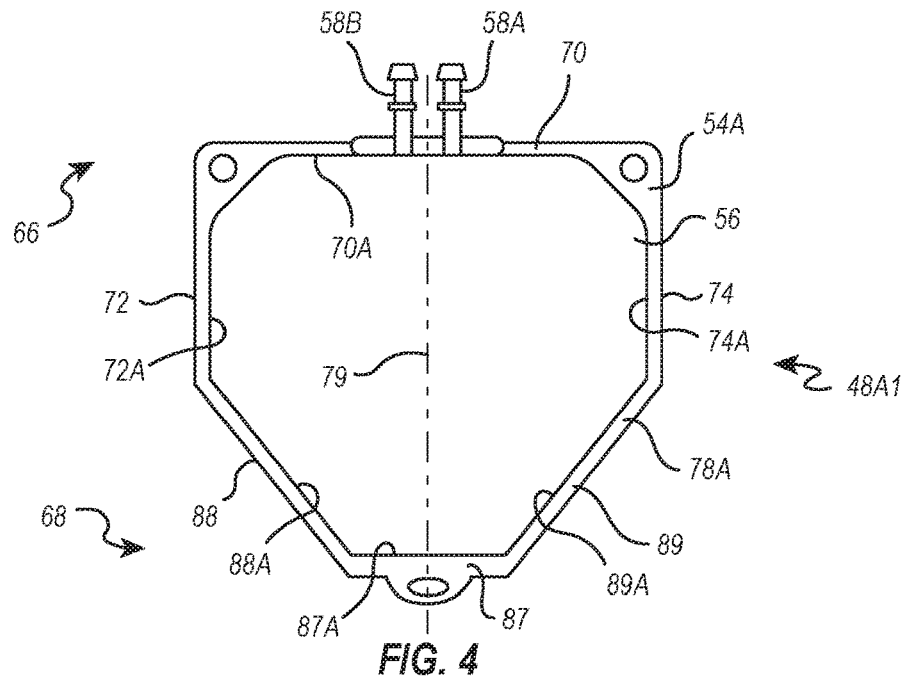
FIG. 4 is an elevated front view of a first alternative embodiment of the bag assembly shown in FIG. 2.

Returning again to FIG. 1, bag assemblies 48B-48D can have the same configuration, components and alternatives as discussed above with regard bag assembly 48A. As such, like elements between bag assembly 48A and bag assembles 48C-48D are identified by like reference characters. It is appreciated that bag assemblies 48A-48D can also have a variety of other configurations. For example, depicted in FIG. 4 is a bag assembly 48A1. Bag assembly 48A1 comprises a bag 54A having ports 58A and 58B mounted thereon. Bag 54A has substantially the same configuration and can be made of the same materials as bag 54. However, in contrast to having bottom seam line section 78 with a continuous curve, bag 54A has a bottom seam line section 86 having a truncated V-shaped configuration that includes a central seam line section 87 having an interior edge 87A that is disposed parallel to inner edge 70A and arm seam line sections 88 and 89 that outwardly extend from opposing ends of central seam line section 87 to side seam line sections 72 and 74, respectively. Arm seam line sections 88 and 89 each have an inner edge 88A and 89A, respectively, that is linear and that intersects with inner edge 87A to form an inside angle between 110° and 170° with between 130° and 150° being more common. Other angles can also be used. Again, with regard to a central longitudinal axis 79 that extends between seam line sections 70 and 87, compartment 56 is more constricted about central longitudinal axis 79 at bottom end 68 than at top end 66, i.e., compartment 56 is narrower at bottom end 68 than at top end 66.

Figure 5:
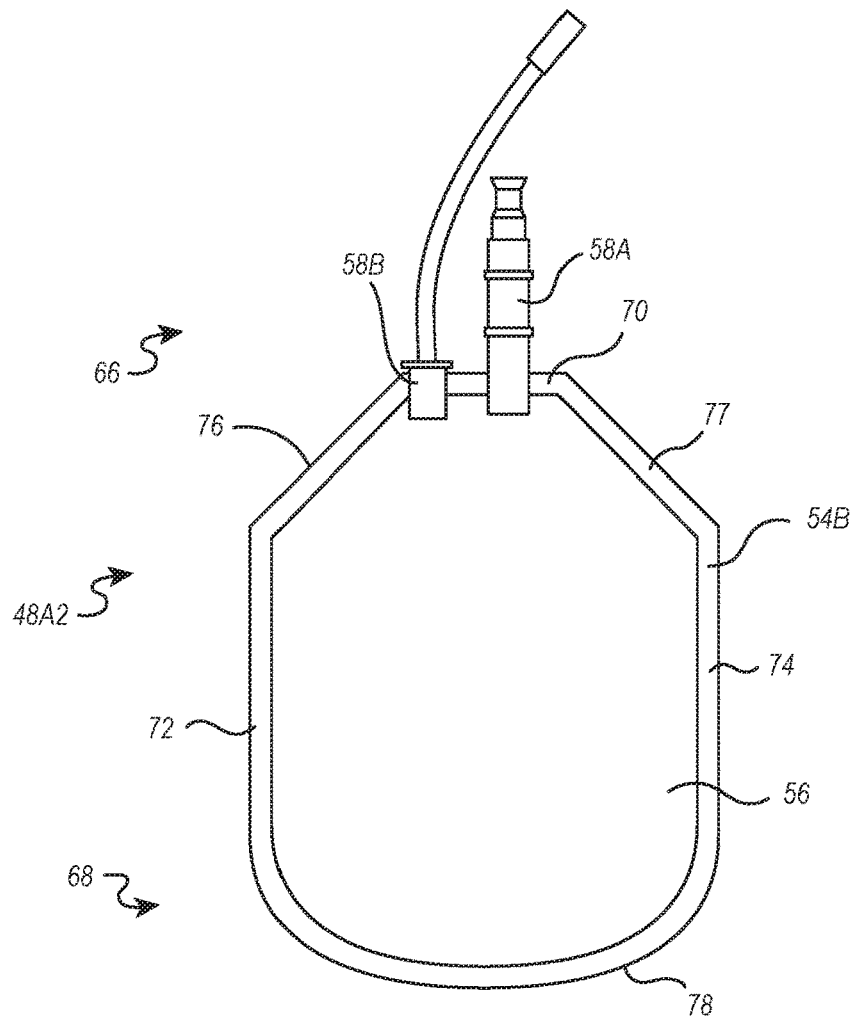
FIG. 5 is an elevated front view of a second alternative embodiment of the bag assembly shown in FIG. 2.

Depicted in FIG. 5 is another alternative embodiment of a bag assembly 48A2 comprising a bag 54B having port 58A and 58B mounted thereon. Bag 54B has the same structural elements and can be made of the same material as bag 54 except that the lengths and curvatures of the elements of bag 54B have been modified relative to bag 54. Like elements between bags 54 and 54B are identified by like reference characters. In this embodiment, compartment 56 is not more constricted at bottom end 68 than at top end 66 but is still constricted by the curvature of bottom seam line section 78 to centrally consolidate the pellet that forms thereat.

Figure 6:
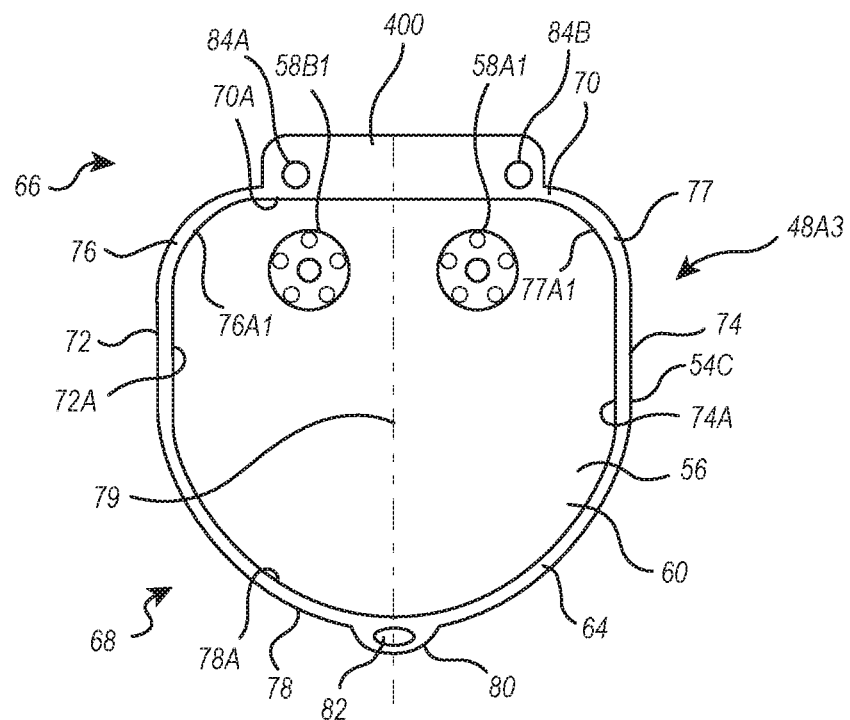
FIG. 6 an elevated front view of a third alternative embodiment of the bag assembly shown in FIG. 2.
Figure 7:
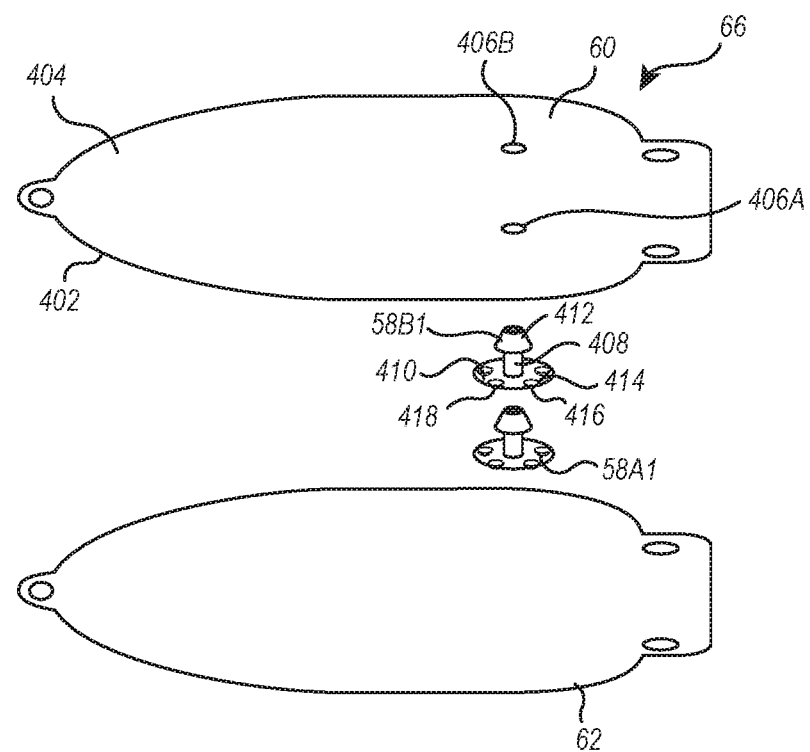
FIG. 7 is an exploded view of the bag assembly shown in FIG. 6.

Depicted in FIGS. 6 and 7 is still another alternative embodiment of a bag assembly 48A3 comprising a bag 54C having ports 58A1 and 58B1 mounted thereon. Bag 54C has substantially the same structural elements and substantially the same configuration as bag 54 and can be made of the same material as bag 54. As such, like elements between bags 54 and 54C are identified by like reference characters and the prior discussion with regard to the elements of bag 54 is also applicable to bag 54C. Bag 54C differs from bag 54 is that corner seam lines sections 76 and 77 are curved. As such, corner seam line section 76 has an inner edge 76A1 that inwardly curves in an arc from inner edge 72A to inner edge 70A and corner seam line section 77 has an inner edge 77A1 that inwardly curves in an arc from inner edge 74A to inner edge 70A. In other embodiments, inner edges 76A1 and 77A1 could also be linear as in bag 54. Bag 54C also has a hanging tab 400 formed at top end 66 and outwardly projecting from top seam line section 70. Openings 84A and 84B extend through hanging tab 400 and are used for supporting bag 54C in a vertical orientation. Hanging tabs 80 and 400 can simply comprise portions of the flexible film used to bound compartment 56 of bag 54C.

Bag assembly 48A3 differs from bag assembly 48A in that bag assembly 48A3 does not include ports 58A and 58B (FIG. 2) projecting from top seam line section 70. Rather, bag assembly 48A3 includes ports 58A1 and 58B1 that are secured to and outwardly project from first sheet 60 at or toward top end 66 at locations spaced apart from seam line 64. Specifically, first sheet 60 has an inside face 402 and an opposing outside face 404 having opening 406A and 406B extending therethrough at locations spaced apart from the perimeter edge of first sheet 60. Each port 58A1 and 58B1 includes a tubular stem 408 having an annular flange 410 outwardly projecting from one end and an annular barb 412 outwardly projecting from an opposing end. Flange 410 has a top side 414 that faces toward stem 408 and an opposing bottom side 416. One or more projections 418 can project from bottom side 416. Projections 418 ensure that a spacing is formed between first sheet 60 and second sheet 62 at ports 58A1 and 58B1 so that fluid can freely flow from compartment 56 out through stems 408. During assembly, stems 408 of ports 58A1 and 58B1 are passed though openings 406A and 406B, respectively, and flanges 410 are secured, such as by welded, adhesive or the like, to inside face 402 of first sheet 60. Ports 58A1 and 58B1 can then be used in the same way as discussed herein with regard to ports 58A and 58B.

In the assembled configuration, ports 58A1 and 58B1 thus extend through first sheet 60 as opposed to simply being secured between sheets 60 and 62. Furthermore, ports 58A1 and 58B1 are typically, though not required, equally spaced on opposing sides of central longitudinal axis 79 and are disposed at top end 66 at locations spaced apart from seam line 64. With reference to bag assembly 48A3 and longitudinal axis 79 being vertically orientated, as shown in FIG. 6, ports 58A1 and 58B1 are typically located within the upper ⅓, ¼, or ⅕ of the area of outside face 404 of first sheet 60 or within the upper ⅓, ¼, or ⅕ of the height/length of first sheet 60/bag 54C. Securing ports 58A1 and 58B1 on the face of first sheet 60, as discussed above, results in less leaking, less integrity testing, and easier attachment than ports 58A and 58B welded between first sheet 60 and second sheet 62. However, securing ports 58A1 and 58B1 on the face of first sheet 60 can make it more difficult to remove all of the fluid from bag 54C relative to having ports 58A and 58B welded between sheets 60 and 62. As such, the selected configuration for bag assemblies 48 can depend on the intended use. Other benefits resulting from the use of ports 58A1 and 58B1 are discussed below.

In the above discussed embodiments, bags 54 are disclosed as being two-dimensional, pillow type bags formed by seaming together two overlapping sheets of flexible film. In other embodiments, however, bags 54 can comprise three-dimensional bags that are typically formed by seaming together three, four or more sheets of flexible film. In yet another embodiment, bags 54 can be blown bags that are blown from a polymeric material and have no seam lines except at the opening through which they are blown. Because of the material that is used to form bags 54, which includes bags 54A, 54B, 54C and the other alternatives discussed herein, bags 54 are collapsible in that they can be fully inflated and fully deflated flat without plastic deformation. Bags 54 can also be folded over or rolled into a tube without plastic deformation.

Figure 8:
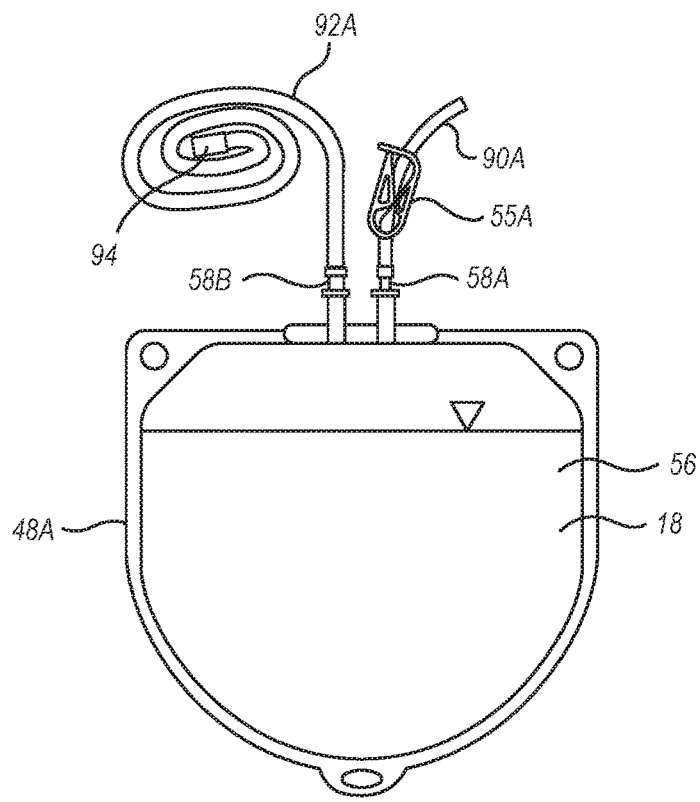
FIG. 8 is an elevated front view of the bag assembly of the manifold system shown in FIG. 1 including an inlet line and an outlet line.

Returning to FIG. 1, fluid line 50 includes inlet lines 90A-90D that are fluid coupled with ports 58A disposed on bags 54. Clamps 55A-55D are mounted on inlet lines 90A-90D, respectively. Clamps 55A-55D can be manually adjusted to regulate the flow of suspension 18 through inlet lines 90A-90D and can seal off inlet lines 90A-90D to prevent fluid flow therethrough. In addition, outlet lines 92A-92D are coupled with ports 58B disposed on bags 54. As depicted in FIG. 8, each outlet line 92 has a terminal end with a fitting 94 disposed thereat. Fitting 94 can comprise a cap that seals outlet line 92 closed or it can comprise an aseptic connector that maintains outlet line 92 sealed closed but enables outlet line 92 to be selectively fluid coupled with another line under aseptic conditions. Other fittings can also be used. In yet other embodiments, fitting 94 can be eliminated and the terminal end of each outlet line 92 can simply be sealed closed, such as by being welded closed.

As discussed below in more detail, once a bag 54 has been filled with a desired amount of suspension 18, a portion of inlet line 90 upstream of clamp 55 is sealed closed and then cut, thereby separating each bag 54 from manifold 46. Accordingly, as depicted in FIG. 8, each bag assembly 48 can be further defined as comprising the portion of inlet line 90 that is separated from manifold 46, clamp 55, outlet line 92 and, if used, fitting 94. Again, as discussed above in part and discussed further below, each of the different elements of each bag assembly 48 can be modified, eliminated or replaced. For example, different numbers of ports 58, such as 1, 3, 4 or more, can be coupled with each bag 54 with a separate fluid line coupled with each port. In other embodiments, one or more of ports 58 can be eliminated and the corresponding fluid lines can be coupled directly to bag 54. Other shapes and volumes of bags 54 can also be used.

Returning to FIG. 1, all of bag assembles 48A-48D are coupled to manifold 46 in parallel, as opposed to in series. Accordingly, by selectively opening and closing clamps 55, transfer of suspension 18 from container 14 to bag assembles 48 can be controlled. For example, all of clamps 55 can be concurrently opened to allow all of bag assembles 48 to be concurrently filled. Alternatively, by closing all of clamps 55 and then opening clamps 55 consecutively, bag assemblies 48 can be filled in consecutive order. It is appreciated that clamps 55, valves, or other flow regulating devices can also be positioned at other location on manifold 46 to control the flow of suspension 18 therethrough.

Bag assemblies 48 are typically filled by weight. For example, scales 96A-D are shown on which bag assemblies 48A-48D can be disposed, respectively. When a corresponding bag assembly 48 has reached is weight limit, the corresponding clamp 55 is closed. Although FIG. 1 depicts a scale 96 for each bag assembly 48, where bag assemblies are filled consecutively, a single scale 96 can be used and each bag assembly 48 placed on the scale in consecutive order. In contrast to being filled by weight, bag assemblies 48 could be filled by volume. For example, bag assemblies 48 could have a fill line to which they are filled or a flow measuring device could be coupled with manifold 46 to measure the volume of fluid that enters each bag assembly 48. Once the desired volume of suspension 18 is delivered in a bag assembly 48, clamp 55 is again closed.

In the embodiment depicted in FIG. 1, manifold 46 is fluid coupled with four bag assemblies 48A-48D. In alternative embodiments, manifold 46 can be fluid coupled with or with at least 2, 3, 5, 6, 8, 12, or 16 bag assemblies 48, or any other number of bag assemblies 48. In yet another alternative embodiment, bag assemblies 48 could be fluid coupled with manifold 46 in series rather than in parallel. In yet another alternative embodiment, manifold 46 can be eliminated and a single fluid line could be fluid coupled with a single bag assembly 48 for filling.

In one method of assembly, container 14 and manifold system 12 can be assembled together, sealed closed, with or without an outer bag or container, and concurrently sterilized, such as by irradiation. In an alternative method, container 14 and manifold system 12 can be separately produced, sealed closed, with or without an outer bag or container, and sterilized. During use, manifold system 12 can then be fluid coupled with container 14 through an aseptic connection. For example, this can be accomplished under a laminar flow hood by using conventional fluid connectors, or by using a tube welder or aseptic connectors. In most typical usages, however, container 14 and manifold system 12 are jointly or separately sealed closed and sterilized prior to use and are fluid coupled together so that the compartments and fluid passageways therein are not exposed to the open environment during use so as to avoid contamination of suspension 18 or the separated components thereof. That is, compartment 56 of each bag assembly 48 is sterile as suspension 18 is first delivered therein and manifold 46 provides a sterile fluid pathway through which suspension 18 can be delivered into compartment 56. Reactor 10, manifold 46 and bag assemblies 48 combine to form a closed system in that the internal area they bound is not exposed to the open environment. As used in the specification and appended claims, the terms "sterile" and "sterilized" mean that the related item has been subjected to a sterilization process so that the sterility assurance level (SAL) is $10^{-6}$ or lower. Sterility assurance level (SAL) is the probability that a single unit that has been subjected to sterilization nevertheless remains non-sterile, i.e., is not free from bacteria or other living microorganisms. As such, an SAL of $10^{-6}$ means that there is a 1 in 1,000,000 chance that a unit subjected to the sterilization process remains non-sterile.

As noted above, after bag assemblies 48 are filled to their desired amount with suspension 18 and clamps 55 are closed, a section of inlet line 90 upstream of clamps 55 is welded closed. Inlet line 90 is then cut at a central location along the welded section so as to sever each bag assembly 48 from manifold 46 as depicted in FIG. 8. By cutting inlet line 90 at a central location along the welded section, no leaking of suspension 18 occurs from manifold 46 or from the section of inlet line 90 of bag assembly 48. In contrast to welding and cutting inlet line 90 upstream of clamps 55, inlet line 90 could alternatively be welded at a location between clamps 55 and ports 58A and then cut through the welded section. This approach would eliminate clamps 55 as being retained as part of the bag assembles.

Suspension 18 can be dispensed into bag assemblies 48 at different times during the growth cycle. For example, in one method, once suspension 18 has reached a desired growth stage, all of suspension 18 within reactor 10 can be dispensed into bag assemblies 48 for further processing. Alternatively, portions of suspension 18 within reactor 10 can be dispensed into bag assemblies 48 at spaced apart intervals during the growth cycle, e.g., at days 14, 16, 18, etc. In this method, reactor 10 can be replenished with fresh medium to compensate, either exactly or approximately, for the volume of suspension 18 removed from reactor 10. This method may be appropriate during bioproduction cell culture process development to determine any variability in cell performance or the production protein characteristics resulting from extended run time.

Figure 9:
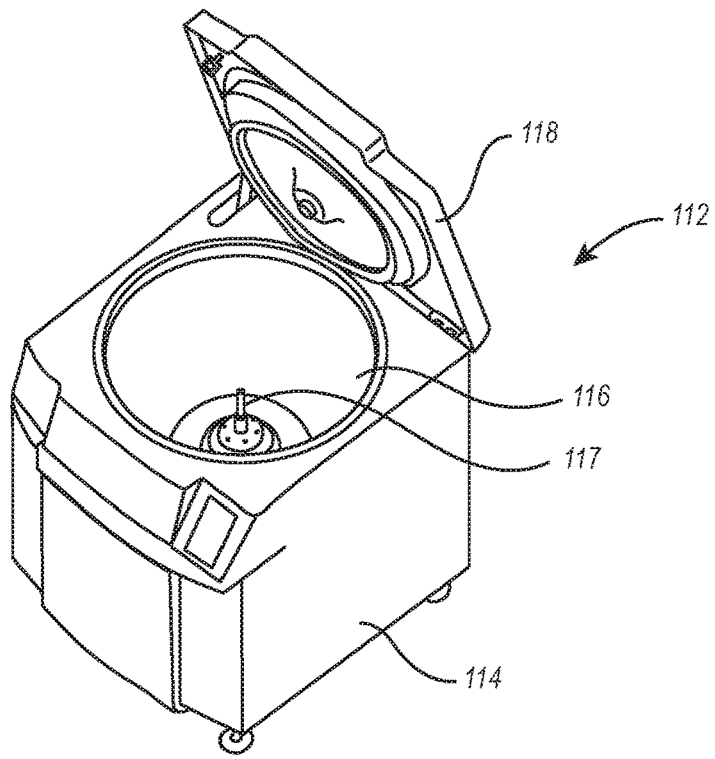
FIG. 9 is a perspective view of one embodiment of a centrifuge (floor standing model) that can be used in the present disclosure.
Figure 10:
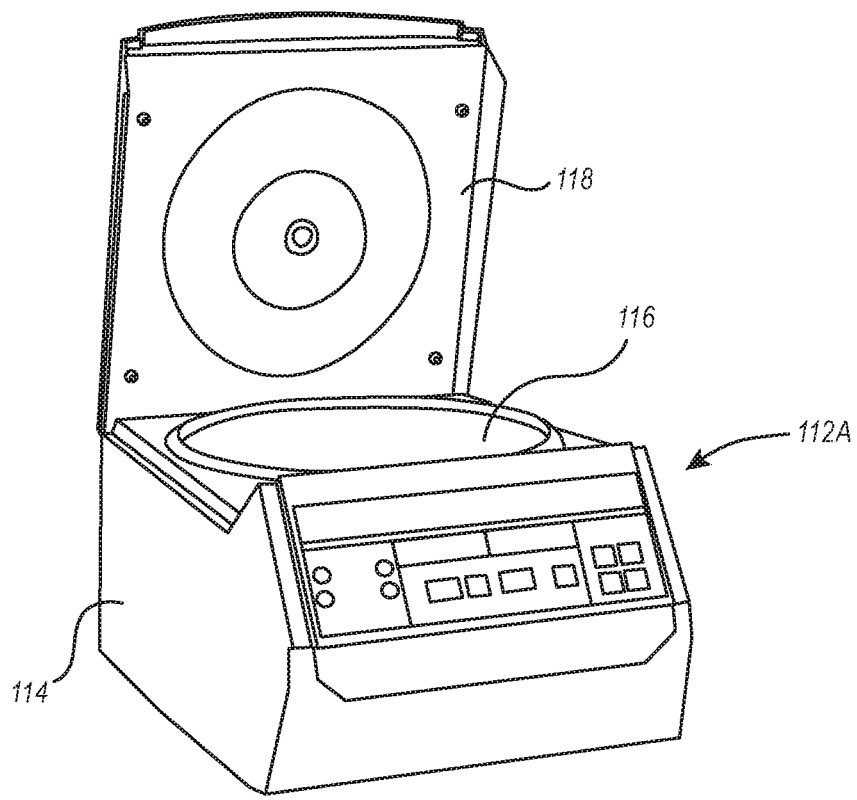
FIG. 10 is a perspective view of an alternative embodiment of a centrifuge (table top model) that can be used in the present disclosure.

Next, separated bag assemblies 48 are moved to a centrifuge for separation of suspension 18 therein. For example, depicted in FIG. 9 is a centrifuge 112. Centrifuge 112 is depicted as a floor standing centrifuge. However, centrifuge 112 can comprise any type, shape, or configuration of centrifuge. For example, depicted in FIG. 10 is a table top centrifuge 112A that can be used in the present disclosure. In general, as depicted in FIG. 9, centrifuge 112 has a body 114 that bounds a cavity 116 and has a spindle 117 disposed therein. Spindle 117 is rotated by a motor disposed within body 114. A lid 118 can be hingedly mounted or removably secured to body 114 for selectively covering cavity 116 during operation. Floor standing centrifuges are commonly used because they have an enlarged cavity 116 that enables handling larger and/or more bag assemblies 48 during each run or operational cycle of the centrifuge.

Figure 11:
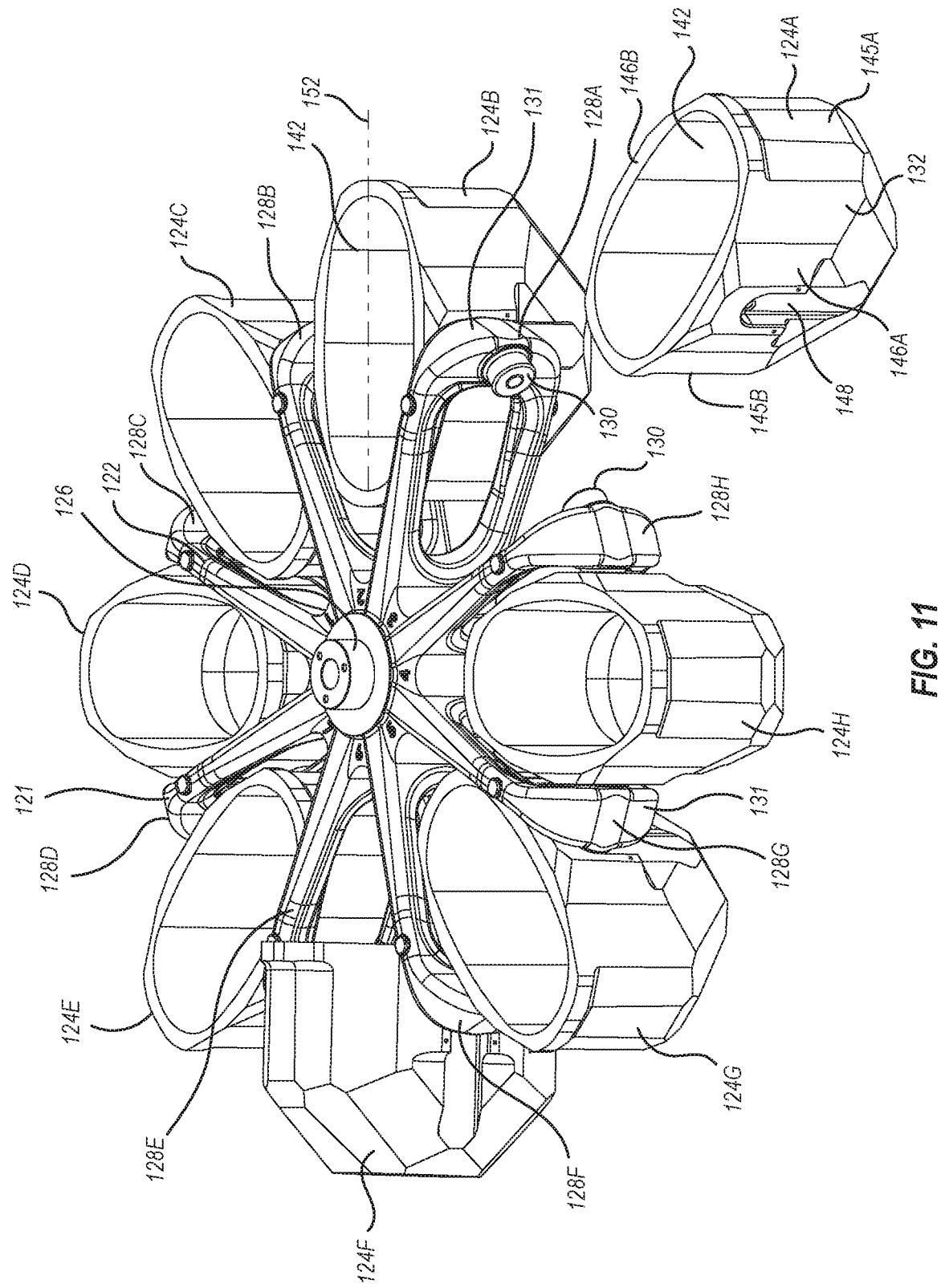
FIG. 11 is a perspective view of a rotor (a swinging-bucket rotor) for use in the centrifuge of FIG. 9 having a plurality of rotatable buckets.

Cavity 116 is configured to receive a rotor that couples with spindle 117 and is rotated within cavity 116 by the rotation of spindle 117. For example, depicted in FIG. 11 is one embodiment of a swinging-bucket rotor 121 that comprises a rotor body 122 having buckets 124A-H that are removable and rotatably coupled thereto. In general, rotor body 122 comprises a central hub 126 that engages with spindle 117 (FIG. 9). Radially outwardly projecting from hub 126 are a plurality of arms 128A-H. Each arm 128 has a hanger 130, commonly referred to as a trunnion, formed on each opposing side thereof at a free end thereof. In the depicted embodiment, each hanger 130 or trunnion comprises a cylindrical projection outwardly extending from each arm 128.

Figure 12:
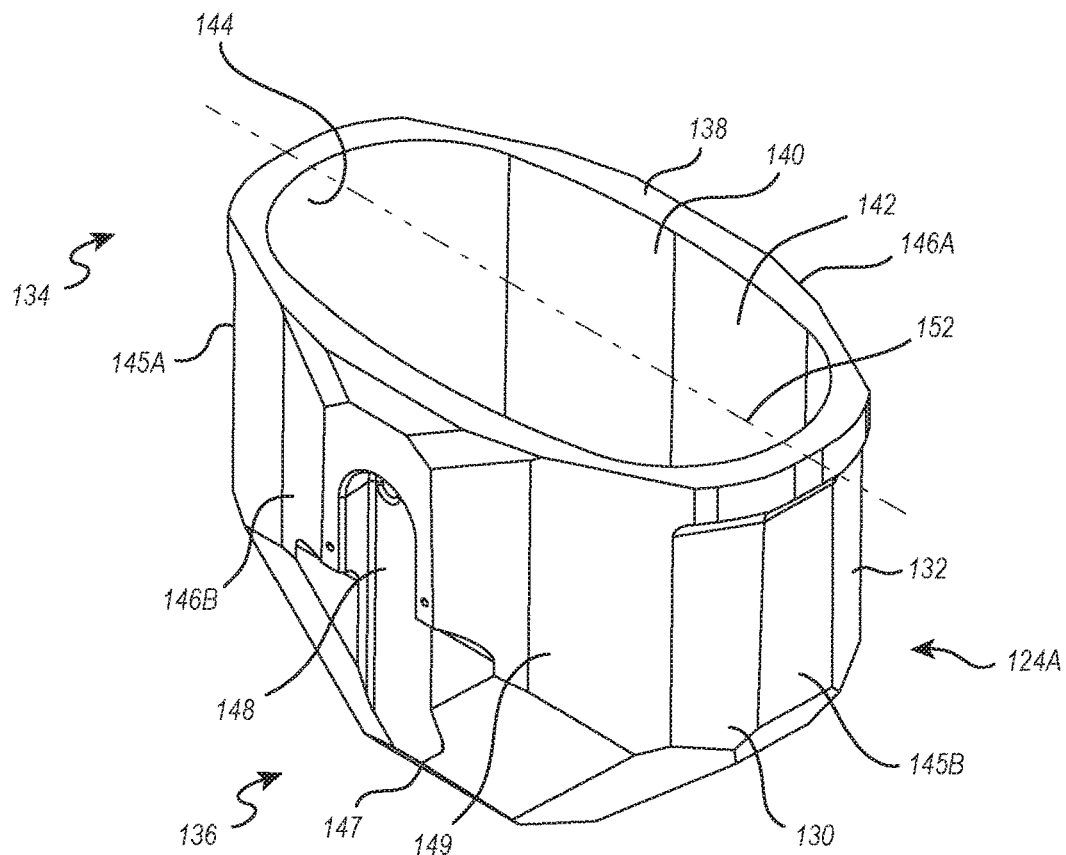
FIG. 12 is a perspective view of one of the buckets shown in FIG. 11.
Figure 13:
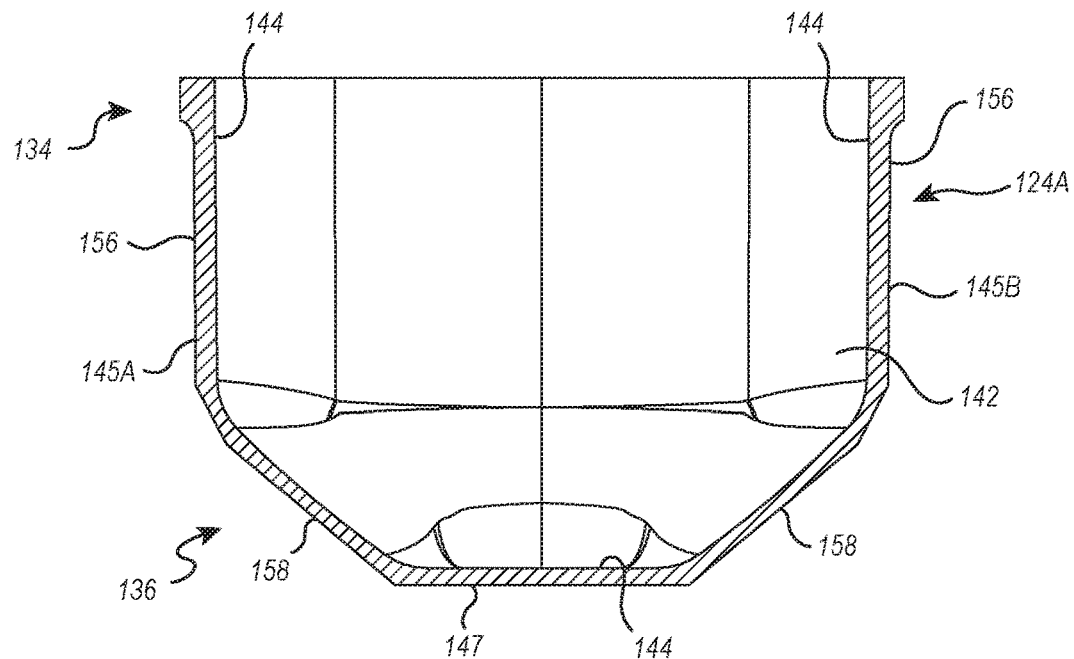
FIG. 13 is a cross sectional side view of the bucket shown in FIG. 12 taken along the longitudinal axis.

As depicted in FIGS. 11 and 12, each bucket 124 comprises a housing 132 having an interior surface 144 that partially bounds a cavity 142 and an opposing exterior surface 149. Housing 132 has an upper end 134 and opposing lower end 136. Upper end 134 terminates at an upper end face 138 that encircles an opening 140 to cavity 142. Lower end 136 terminates at a floor 147 (FIG. 13). Housing 132 further comprises opposing side walls 146A and 146B that extend between opposing end walls 145A and 145B. Formed on exterior surface 149 of each side wall 146A and 146B is a receiver 148 that is configured to removably receive a corresponding hanger 130. Specifically, receivers 148 are configured to receive hangers 130 so that rotor body 122 supports buckets 124 and enables buckets 124 to rotate or swing between a vertical orientation, as depicted with regard to bucket 124B in FIG. 11, and a horizontal orientation, as depicted with regard to bucket 124F in FIG. 11.

In the depicted embodiment, receivers 148 comprise inverted U-shaped slots that are recessed into side wall 146A and 146B and are open toward lower end 136. Receivers 148 are configured so that when buckets 124 are positioned between adjacent arms 128 of rotor body 122, hangers 130 are received and captured within corresponding receivers 148. In this configuration, buckets 124 can freely rotate about hangers 130. Specifically, when rotor body 122 is stationary, buckets 124 hang in the vertical orientation with cavity 142 facing upward as shown by bucket 124B. However, as rotor body 122 begins to rotate, buckets 124 swing or rotate outward by 90° to the horizontal orientation where cavity 142 is facing hub 126 as shown by bucket 124F. When rotor body 122 is deactivated and returns to the stationary position, buckets 124 return to the vertical orientation. Buckets 124 can then again be selectively separated from rotor 120 by being lifted off of hangers 130.

As an alternative to the foregoing, it is appreciated that hangers 130 could be formed on opposing side walls 146A and 146B of bucket 124 while corresponding receivers 148 are formed on each of the opposing sides of arms 128. In this assembly, receivers 148 would be in the shape of upright U-shaped slots recessed into arms 128. In alternative embodiments, it is appreciated that hangers 130 and receives 148 can have other configurations that achieve the above described function.

As depicted in FIG. 12, cavity 142 of buckets 124 is elongated having a longitudinal axis 152 that extends between opposing end walls 145A and 145B. Cavity 142 has a transverse cross section, particularly at upper end 134, that is oval or elliptical. As depicted in FIG. 13, end walls 145A and 145B inwardly taper as they extend from upper end 134 to lower end 136. More specifically, end walls 145A and 145B each include an upper section 156 at upper end 134 and a lower section 158 at lower end 136. In the depicted embodiment, upper section 156 of opposing ends walls 145A and 145B, particularly interior surfaces 144 thereof, are disposed in parallel alignment. Expressed in other terms, interior surfaces 144 of upper sections 156 can be perpendicular to interior surface 144 of floor 147. In contrast, lower sections 158 of end walls 145A and 145B, and particularly interior surfaces 144 thereof, can inwardly taper from corresponding upper sections 156 to floor 147.

In one embodiment, interior surface 144 of floor 147 can intersect with interior surface 144 of lower sections 158 to form an inside angle between 110° and 170° with between 130° and 150° being more common. Other angles can also be used. In alternatives to the above, interior surface 144 of lower sections 158 could outwardly curve between floor 147 and upper sections 156. Furthermore, upper sections 156 need not be parallel but could outwardly flare at an angle less than what lower sections 158 extend. In still other embodiments, interior surface 144 of upper sections 156 can extend in a curve and both upper sections 156 and lower sections 158 can extend in a curve. Other configurations can also be used that result in cavity 142 having an inward taper as cavity 142 extends from upper end 134 to lower end 136.

Figure 14:
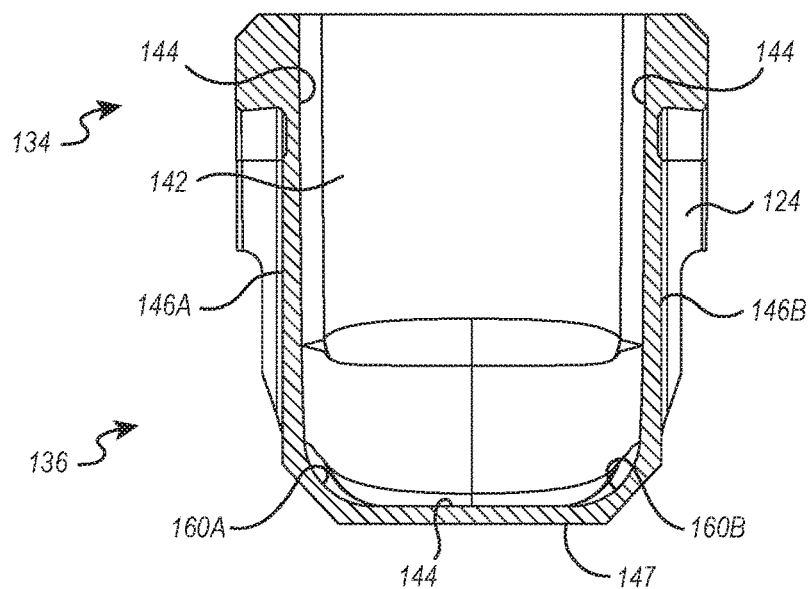
FIG. 14 is a cross sectional side view of the bucket shown in FIG. 12 taken along the transverse axis.

Turning to FIG. 14, interior surfaces 144 of opposing side walls 146A and 146B are disposed parallel to each other and perpendicular to interior surface 144 of floor 147. However, inwardly curved corners 160A and 160B are formed at the intersection between floor 147 and side walls 146A and 146B, respectively. Corners 160A and 160B give an inward tapering to cavity 142 at lower end 136. In alternative embodiments, interior surfaces 144 of opposing side walls 146A and 146B could also flare outward away from floor 147 either linearly or in a curve. Again, such a configuration results in cavity 142 having an inward taper as it extends from upper end 134 to lower end 136.

Figure 15:
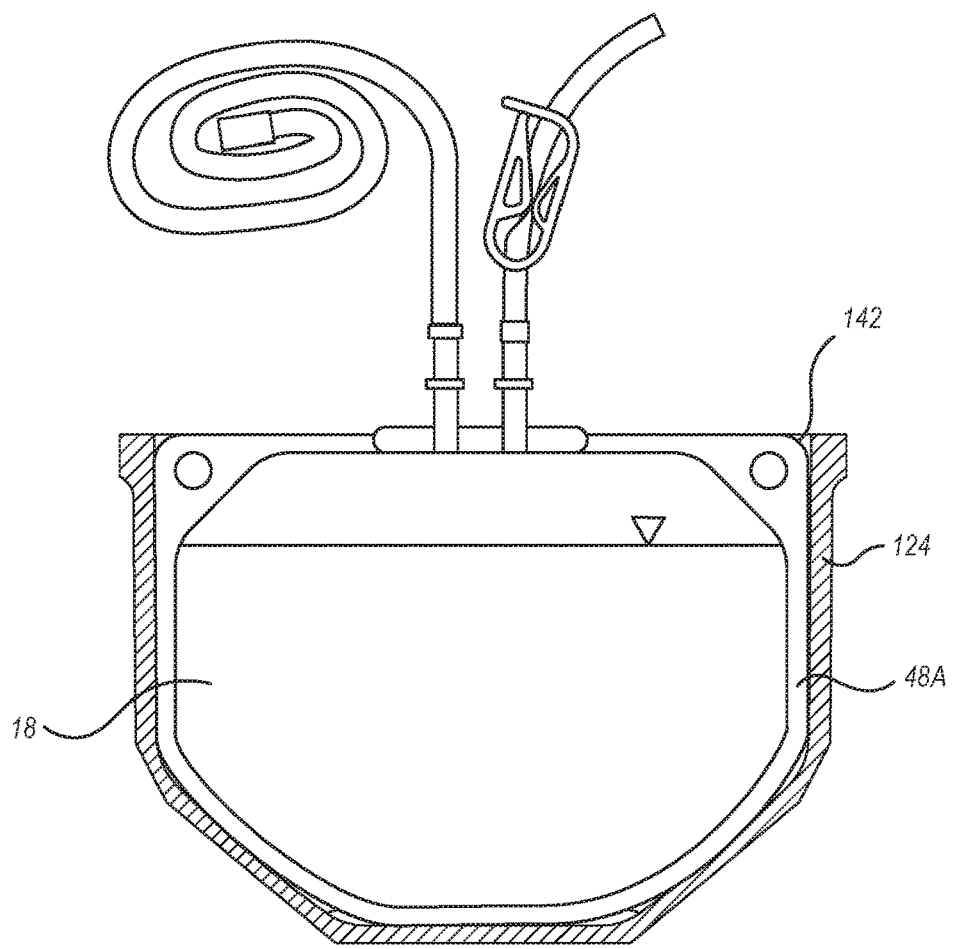
FIG. 15 is a partial cross-sectional side view of the bag assembly shown in FIG. 2 within the bucket shown in FIG. 12.

Interior surface 144 of each bucket 124 is contoured so that cavity 142 has a configuration that is generally complementary to bag assemblies 48 when bag assemblies 48 are filled with suspension 18. This contouring has a number of benefits. For example, by having a generally complementary fit between bag assemblies 48 and buckets 124, less movement and thus less stress is produced on bag assemblies 48 as bag assemblies 48 are rotated within centrifuge 112. This complementary fit is illustrated in FIG. 15 where bag assembly 48A is disposed directly within cavity 142 of bucket 124. Furthermore, because of the inward taper of cavity 142 toward lower end 136, buckets 124 assist bag assemblies 48 in producing centrally located and consolidated pellets, the benefits of which were previously discussed.

In addition, the generally complementary fit between bag assemblies 48 and buckets 124 results in fewer creases and folds being formed in bag assemblies 48 as bag assemblies 48 are rotated by centrifuge 112. Creases and folds are undesirable because the solids of suspension 18 can settle within the creases or folds during centrifugal separation, as opposed to collecting as a single, consolidated pellet on the floor of bag assemblies 48. In turn, as bag assemblies 48 are removed from buckets 124 or other centrifuge rotors, the folds and creases are removed causing the solids therein to be disturbed and thus resuspended within the supernatant, thereby at least partially defeating the objective of using the centrifuge.

Figure 16:
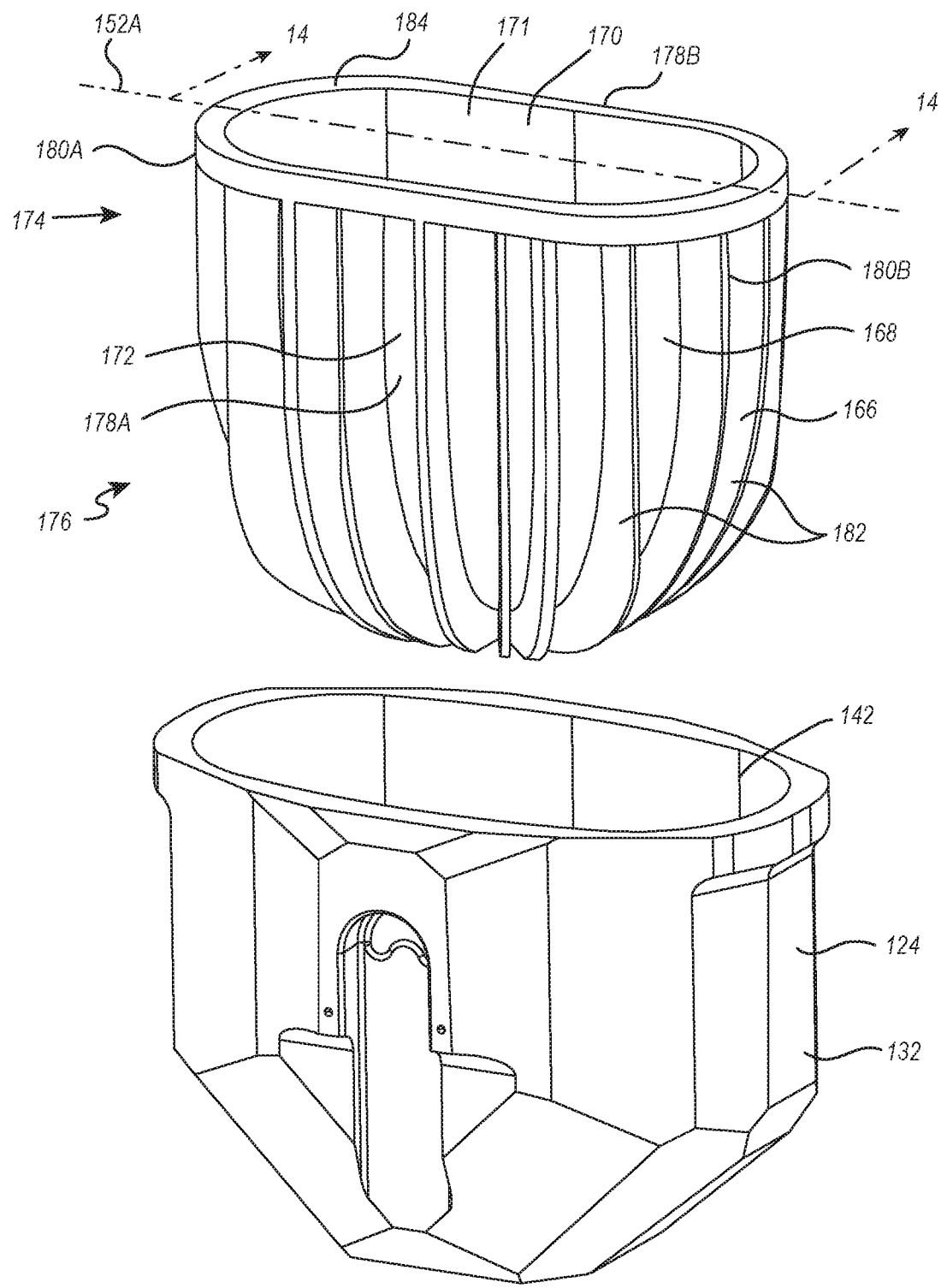
FIG. 16 is a perspective view of the bucket shown in FIG. 12 and an insert for use within the bucket.

In the above discussed embodiment, each bag assembly 48 is received directly within cavity 142 of a corresponding bucket 124 for rotation by centrifuge 112. However, buckets 124 are generally rigid and have minimal flexing or bending during rotation within centrifuge 112. In an alternative embodiment, as depicted in FIG. 16, an insert 166 can be received within cavity 142 of each bucket 124. In turn, each bag assembly 48 can be received within a cavity 171 of each insert 166. More specifically, insert 166 is typically formed from a soft, resiliently flexible polymer and is more flexible than housing 132 of bucket 124. Insert 166 can be sufficiently flexible that cavity 171 can be completely collapsed without plastic deformation of insert 166. In one embodiment, inserts 166 can be molded from polyamide. Other materials can also be used. Although inserts 166 can have a variety of different configurations, in the current embodiment, insert 166 has a cupped shaped body 168 having an interior surface 170 and an opposing exterior surface 172 that extend between an upper end 174 and opposing lower end 176. Body 168 has opposing side walls 178A and 178B that extend between opposing end walls 180A and 180B. A plurality of ribs 182 outwardly project from exterior surface 172 and extend longitudinally between upper end 174 and lower end 176 around exterior surface 172.

Figure 17:
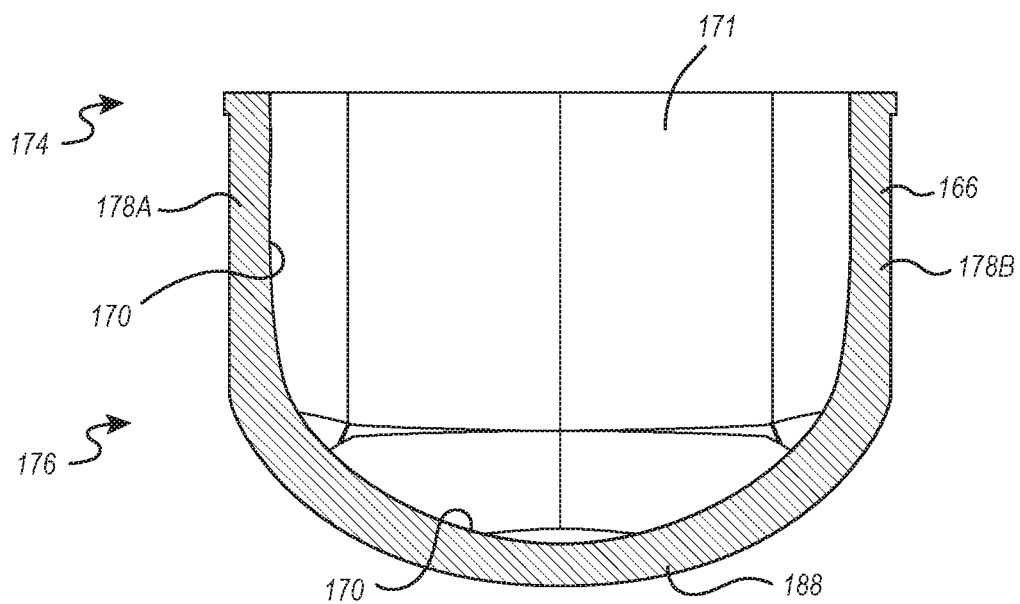
FIG. 17 is a cross sectional side view of the insert shown in FIG. 16 taken along the longitudinal axis thereof.

Upper end 174 terminates at an upper end face 184 that encircles an opening 186 to cavity 171. Interior surface 170 of cavity 171 can have the same or similar configuration as cavity 142 of buckets 124. Specifically, cavity 171 of inserts 166 is elongated having a longitudinal axis 152A that extends between opposing end walls 180A and 180B. Cavity 171 has a transverse cross section that is oval or elliptical and that inwardly tapers as it extends from upper end 174 to lower end 176. More specifically, as shown in FIG. 17, body 168 has a floor 188 with an interior surface 170 that is curved and extends up at opposing ends end walls 180A and 180B. End walls 180A and 180B have interior surfaces 170 that are parallel to each other but could be outwardly flared or curved. Again, interior surface 170 of body 168 can have the same configuration and alternatives as interior surface 144 of buckets 124 and visa-versa and the configuration of insert 166 is designed to achieve the same benefits as discussed above with regard to buckets 124.

Figure 18:
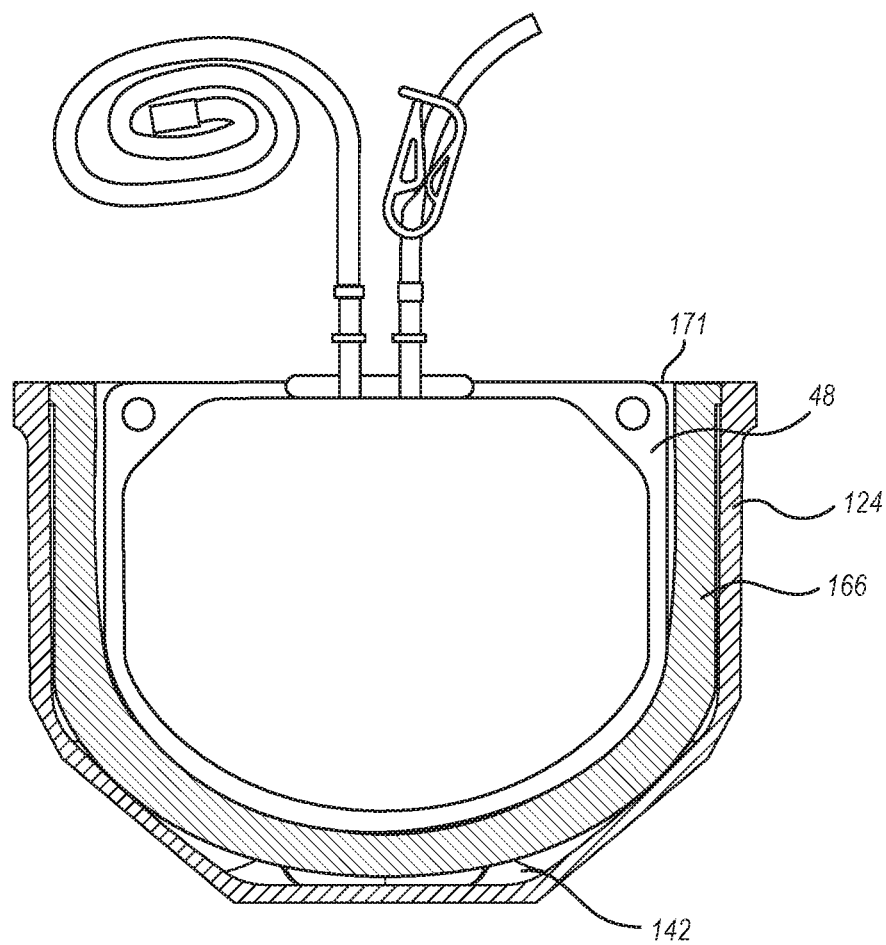
FIG. 18 is a partial cross sectional side view of the bag assembly inserted within the insert of FIG. 13 and housed within the bucket.

As depicted in FIG. 18, insert 166 is configured to fit in a complementary fashion within cavity 142 of bucket 124 while bag assembly 48 is configured to fit in a complementary fashion within cavity 171 of insert 166. However, because inserts 166 are soft and more resiliently flexible than buckets 124, inserts 166, if properly configured, can help support and reduce stress on bag assemblies 48 during rotation within centrifuge 112.

Because buckets 124 and inserts 166 are removable from rotor body 122 (FIG. 11), in one method of use, bag assembles 48 could be inserted within cavity 142 of buckets 124 or within cavity 171 of inserts 166 prior to being filled with suspension 18. Suspension 18 can then be delivered into bag assemblies 48 while bag assemblies 48 are disposed within buckets 124 or inserts 166. In turn, buckets 124 can then be mounted on rotor body 122 and inserts 166 can be positioned within buckets 124.

Figure 19:
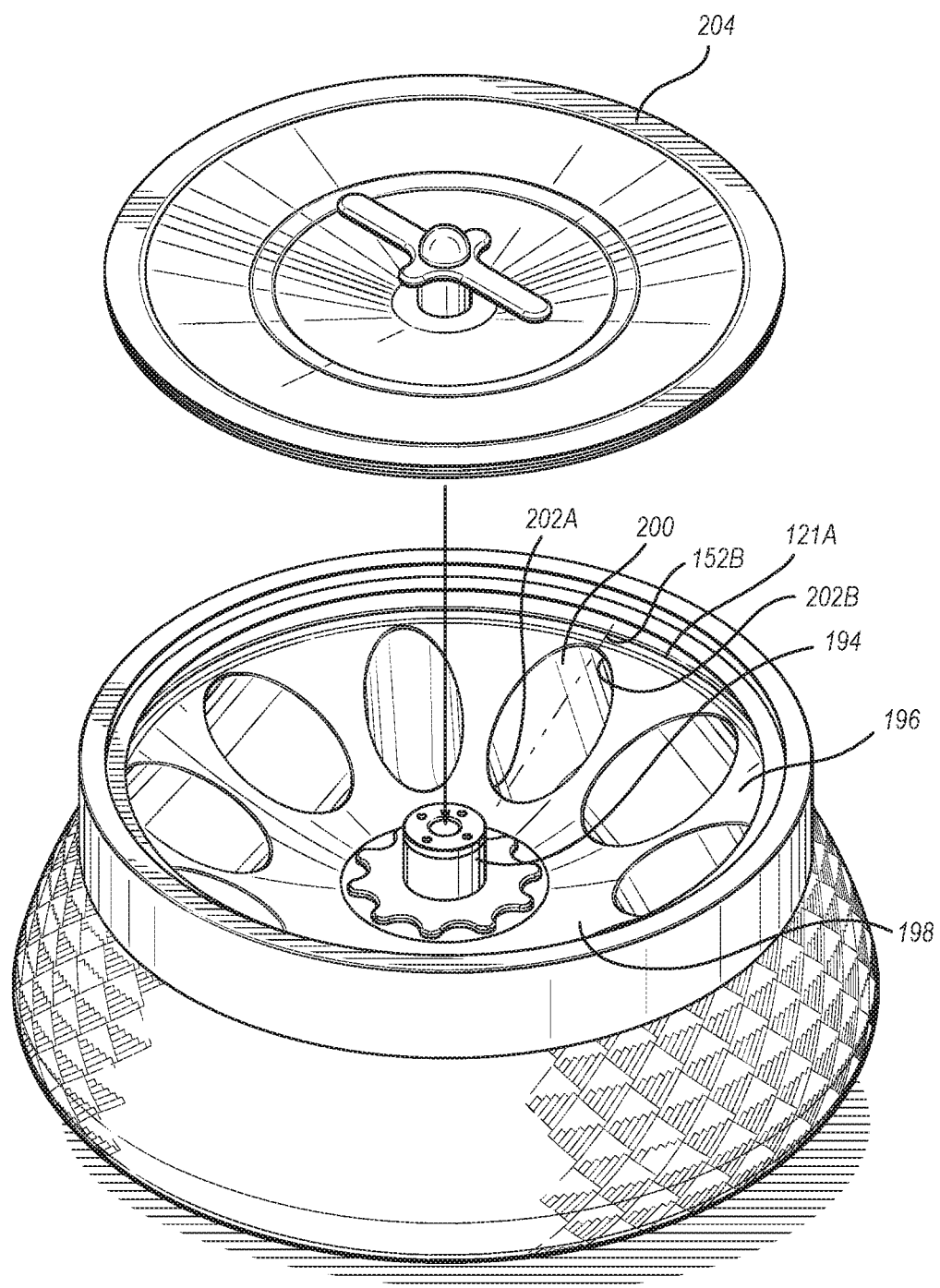
FIG. 19 is a perspective view of an alternative rotor (a fixed angle rotor) for use with the centrifuge in FIG. 9 in which the bag assemblies can be disposed.

In contrast to using swinging-bucket rotor 121, a fixed angle rotor 121A, as depicted in FIG. 19, can also be used. Rotor 121A is likewise configured to be received within cavity 116 of centrifuge 112 (FIG. 9) and has a hub 194. Hub 194 couples with spindle 117 (FIG. 9) for the rotation of rotor 121A. Rotor 121A has a body 196 that encircles and radially outwardly projects from hub 194. Body 196 has a top surface 198 that slopes radially out and upwardly from hub 194. Recessed into body 196 from top surface 198 are a plurality of radially spaced apart cavities 200. Each cavity 200 can have the same configuration and alternatives as cavity 142 of buckets 124 or cavity 171 of insert 166. For example, each cavity 200 is elongated having a longitudinal axis 152B that extends between opposing end walls 202A and 202B and is aligned with hub 194. Cavity 200 has a transverse cross section that is oval or elliptical and that inwardly tapers as it extends from an upper end to an opposing lower end. Each cavity 200 is configured to receive in a complementary fit an individual bag assembly 48 filled with suspension 18 so as to minimize stress on bag assemblies 48 during rotation. Cavities 200 thus achieve the same functions as discussed above with regard to cavities 142 of buckets 124.

However, in contrast to buckets 124 where the orientation of cavities 142 change based on the rotation of rotor body 122, cavities 200 are always disposed at the same orientation during the rotation of rotor 121A. Each cavity 200 can be oriented at various fixed angles relative to the horizontal, with angles of 30° to 60° being common, and angles of 30° to 45° degrees being more common. Other angles can also be used. As a result, the pellet formed by centrifuge 112 is typically formed off-center from the floor of bag assembly 48. If desired, a lid 204 can be coupled with hub 194 and used to cover cavities 200, and thus the bag assemblies 48 therein, during rotation of rotor 121A.

Figure 20:
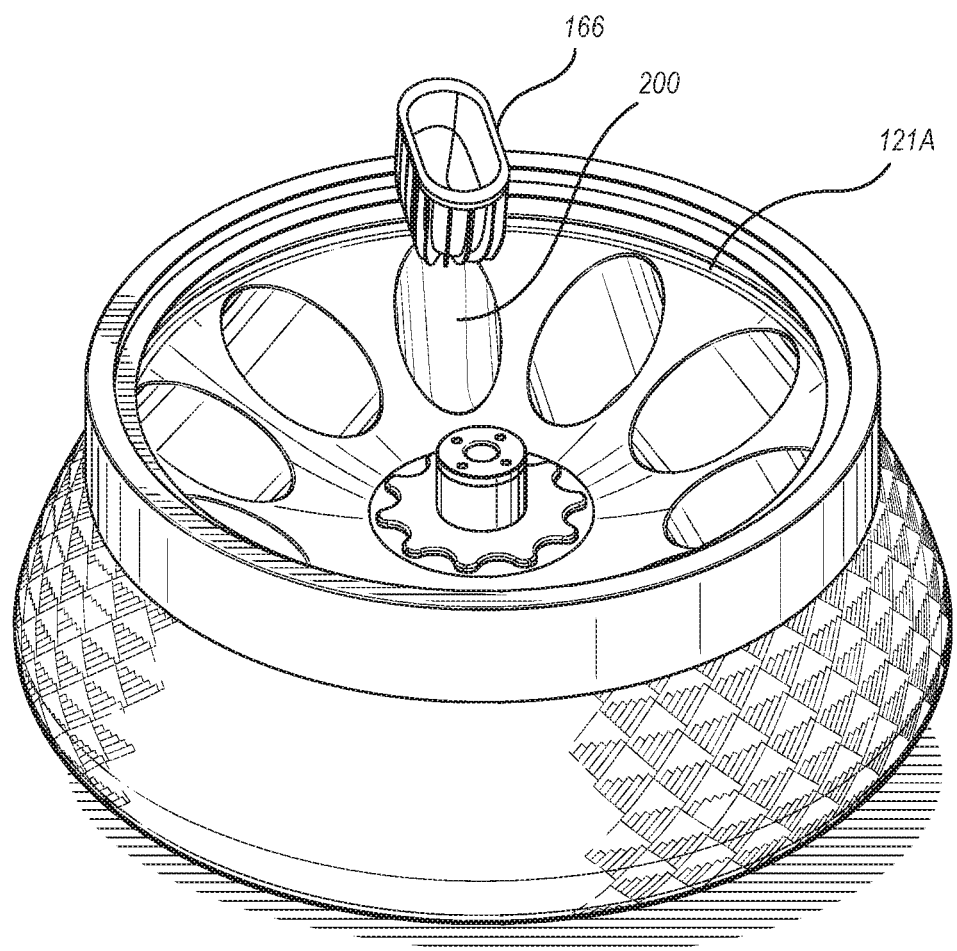
FIG. 20 is a perspective view of the rotor shown in FIG. 19 used with the insert shown in FIG. 16.

Turning to FIG. 20, inserts 166 can also be received within cavities 200 of rotor 121A to compensate for changes in size or shapes of bag assemblies 48 and/or to minimize stress on and movement of bag assemblies 48. In addition, inserts 166 can be configured to fully support bag assemblies 48 during rotation of rotor 121A to help prevent failure or leaking of bag assemblies 48. For example, when bag assemblies 48 are placed within cavities 200 and the centrifuge is activated to rotate rotor 121A, suspension 18 and the surrounding bag assemblies 48 are forced radially outward under the centrifugal force produced by the centrifuge. Because cavities 200 are fixed relative to rotor 121A, in some configurations of rotor 121A, as suspension 18 is forced radially outward, a portion of suspension 18 can flow up and out of cavity 200, thereby forcing a portion of bag assemblies 48 out of cavity 200. This displacement of bag assemblies 48 out of cavities 200 during the rotation of rotor 121A can lead to stretching and distortion of bag assemblies 48 which can result in failure or leaking of bag assemblies 48. To prevent this displacement of bag assemblies 48, rotor 121A and/or cavities 200 can be configured to fully support bag assemblies 48 during rotation. For example, cavities 200 can be formed deeper and/or cavities 200 can be orientated more horizontal, i.e., the opening of each cavity being angled more toward the center of rotor 121A.

In other embodiments, inserts 166 can be used that when nested within cavities 200 project upward a distance out of cavities 200, thereby providing more surface area for fully supporting bag assemblies 48 during rotation of rotor 121A. One example of such inserts is insert 166B, discussed below with regard to FIGS. 35-37. Insert 166B can project annularly out of cavity 200 or can be configured so that only the end disposed toward the outer perimeter of rotor 121A projects upward out of cavities 200 to provide the needed support for bag assemblies 48 during rotation. In still other embodiments, cavities 200 and/or inserts 166/166B can be provided with a removable cap for fully retaining and supporting bag assemblies 48 within cavities 200 and or inserts 166/166B during rotation of rotor 121A.

Figure 21:
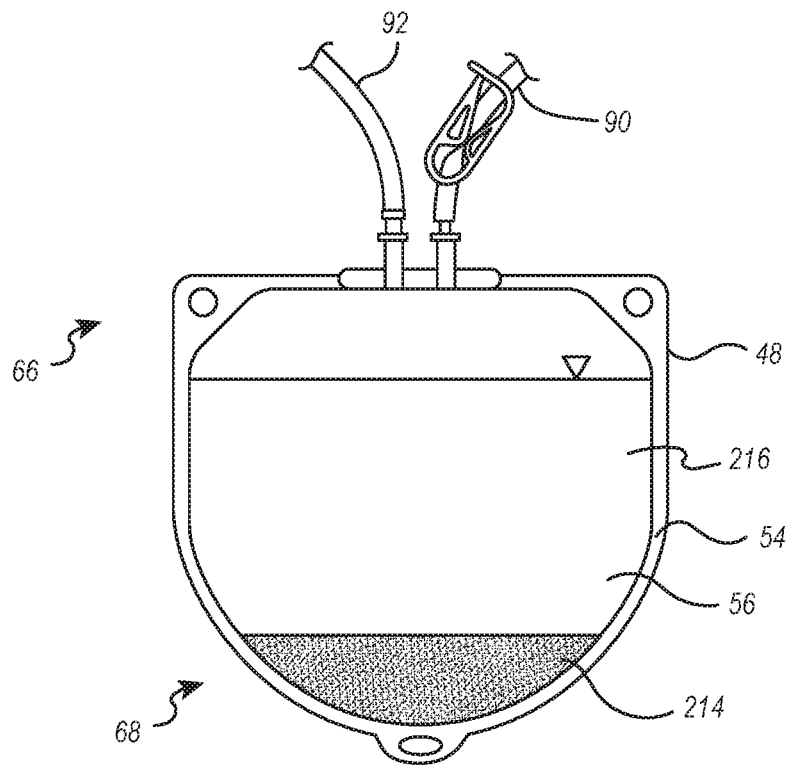
FIG. 21 is an elevated front view of the bag assembly shown in FIG. 15 after being removed from the centrifuge.

Turning to FIG. 21, as bag assemblies 48 are rotated within centrifuge 112 (FIG. 9), the centrifugal force caused by spinning of the rotor causes at least a portion of the solids within suspension 18, e.g., the cells, microorganisms, and/or other solids, to sediment out of the solution and collect within bottom end 68 of bag assembly 48 to form a pellet 214. The remaining fluid collects as a supernatant 216 above pellet 214 and can include some solids. Pellet 214 has a density that is greater than the density of supernatant 216. Pellet 214 can also have a viscosity that is greater than the viscosity of supernatant 216. For example, the density and viscosity of pellet 214 can be at least 2, 5, 7, 10, 15, 30 or 50 times that of supernatant 216. In one application, pellet 214 can comprise a paste or a slurry while supernatant 216 typically comprises a free flowing liquid, like water.

As discussed above, there are benefits to having the bag assembly and rotor configured so that pellets 214 form and consolidate at one location at (or near) bottom end 68 of bag assemblies 48. Some cells, microorganisms, and/or other solids of suspension 18 are found to make a generally firm and compact pellet 214 that is not easily disturbed and resuspended into supernatant 216. In contrast, however, other cells such as mammalian cells, like Chinese hamster ovary (CHO) cells, can form a slurry or very loose pellet 214 and thus are easily resuspended into supernatant 216. The time and speed at which bag assemblies 48 containing suspension 18 are rotated by centrifuge 112 is dependent in part on the composition and volume of suspension 18. However, bag assemblies 48 are typically spun at a rate between 300 rpm and 5,000 rpm with between 2,000 rpm and 5,000 rpm being more common. The time of rotation is typically between 5 minutes and 90 minutes with between 5 minutes and 30 minutes being more common. Other rates and times can also be used.

It is noted that because buckets 124 of swinging-bucket rotor 121 (FIG. 11) freely swing outward by 90° during rotation, the centrifugal force causes pellet 214 to be directed to floor 147 of cavity 142 (FIG. 13). In contrast, because cavities 200 of fixed angle rotor 121A (FIG. 19) are maintained at a fixed angle during rotation, the centrifugal force causes pellet 214 to be directed toward the sidewall of cavity 200. As a result, swinging-bucket rotor 121 can be more efficient than fixed angle rotor 121A in collecting and consolidating pellet 214 centrally on bottom end 68 of bag assembly 48.

Figure 22:
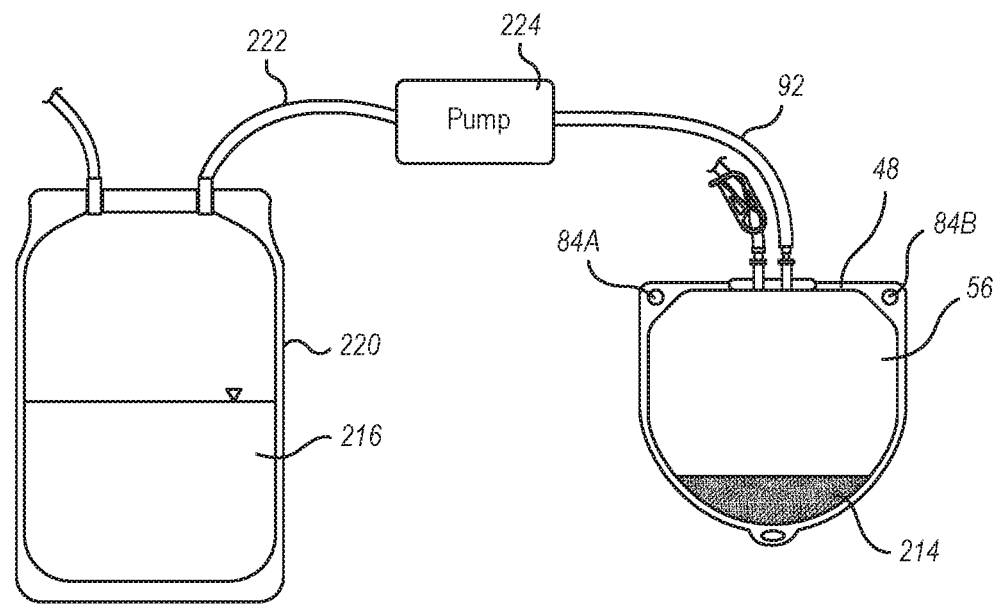
FIG. 22 is an elevated front view of the bag assembly shown in FIG. 21 fluid coupled with a container in which the supernatant is being pumped.

Once suspension 18 within bag assemblies 48 is separated into pellets 214 and supernatant 216, the next step is to remove supernatant 216 from bag assemblies 48. Where pellet 214 is firm and not easily resuspended, as discussed above, this step can be accomplished by fluid coupling outlet line 92 to a container 220 as depicted in FIG. 22. For example, where fitting 94 (FIG. 8) is a cap, outlet line 92 can be cut, such as in a laminar flow hood, and then fluid coupled with container 220 using a sterile connection. In one method, outlet line 92 can be welded to an inlet line 222 extending from container 220 or can be directly coupled to container 220. Alternatively, where fitting 94 (FIG. 8) is an aseptic connector, fitting 94 can simply be coupled to a corresponding aseptic connector on inlet line 222 of container 220 to form a sterile fluid coupling. A pump 224, such as a peristaltic pump, can then be engaged with the coupled fluid lines and used to pump supernatant 216 out of bag assembly 48 into container 220. During the coupling of outlet line 92 and/or the pumping of supernatant 216, each bag assembly 48 can be retained in bucket 124 and/or insert 166 although bucket 124 can be removed from rotor body 122. Alternatively, each bag assembly 48 can be removed from bucket 124, insert 166, or other rotor and suspended on a rack, such as by using openings 84, or supported by a separate container or support structure. In any event, however, bag assembly 48 is typically retained in a generally upright orientation, i.e., ports 58A and 58B facing upward or ports 58A1 and 58A2 facing outward, during removal of supernatant 216 to avoid disrupting pellet 214.

Figure 23:
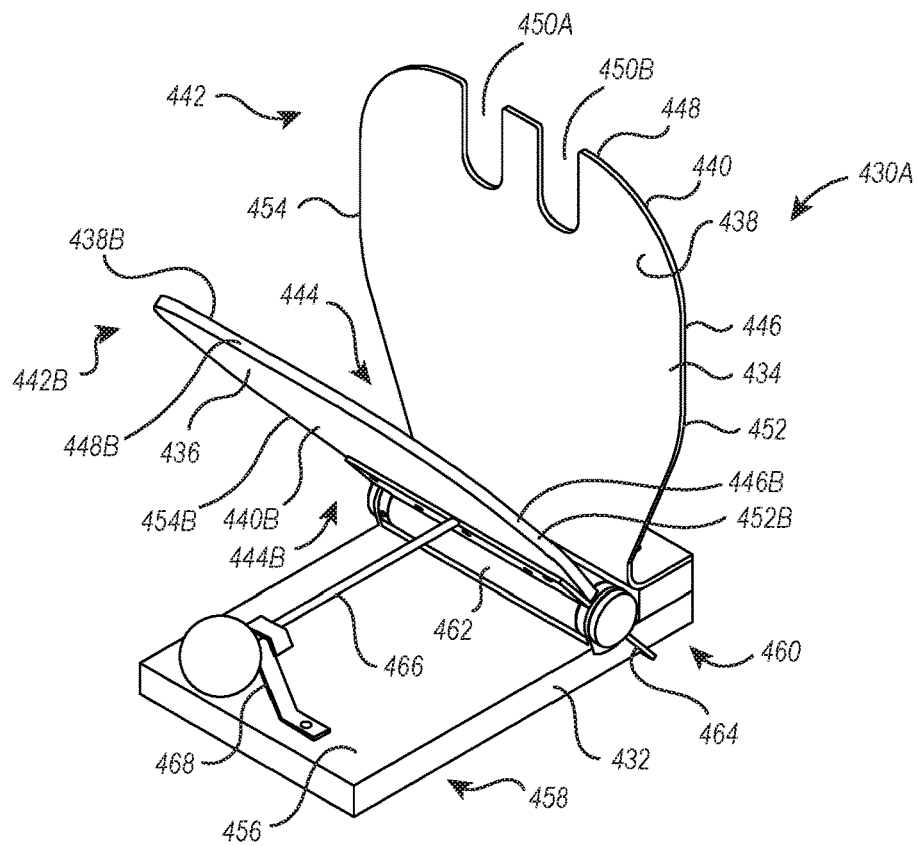
FIG. 23 is a front perspective view of an expressor in a retracted position.

As an alternative to using pump 224, an expressor can be used to drive supernatant 216 from bag assemblies 48 into container 220. As used in the specification and appended claims, the term "expressor" is broadly intended to comprise any type of device that can mechanically compress bag assemblies 48 for driving supernatant 216 therefrom. For example, depicted in FIG. 23 is one embodiment of an expressor 430A incorporate features of the present disclosure. In general, expressor 430A comprises a base 432 having a first platen 434 coupled thereto. A second platen 436 is coupled to base 432 so that second platen 436 can selectively move toward and away from first platen 434. In the depicted embodiment, base 432 has a top surface 456 extending between a first end 458 and an opposing second end 460. First platen 434 is depicted as comprising a plate having an inside face 438 and an opposing outside face 440 that both extend between an upper end 442 and an opposing lower end 444. First platen 434 has a perimeter edge 446 having a tapered configuration similar to the tapered configuration of bag assemblies 48. More specifically, perimeter edge 446 has an upper edge portion 448 having two spaced apart notches 450A and 450B centrally recessed thereon. Perimeter edge 446 also includes opposing side edge portions 452 and 454 that inwardly taper at lower end 444 relative to upper end 442.

First platen 434 is secured to base 432 at or toward second end 460. In one embodiment, first platen 434 is secured so that when base 432 and/or top surface 456 thereof are horizontally disposed, inside face 438 is vertically disposed, i.e., is orthogonal to base 432 and/or top surface 456. In other embodiments, first platen 434 can be angled so that an angle is formed between top surface 456 of base 432 and inside face 438 of first platen 434 that is at least or less than 110°, 120°, 130°, 140°, 150° or 160° or is in a range between any two of the foregoing angles.

Second platen 436 has substantially the same configuration as first platen 434. As such, like elements between platens 436 and 434 are identified by like reference characters except that the reference characters for second platen 436 include the suffix "B." For example, second platen 436 comprises a plate having an inside face 438B and an opposing outside face 440B that both extend between an upper end 442B and an opposing lower end 444B. Second platen 436 has a perimeter edge 446B having a tapered configuration similar to the tapered configuration of bag assemblies 48. More specifically, perimeter edge 446B has an upper edge portion 448B and two opposing side edge portions 452B and 454B. Side edge portions 452B and 454B inwardly taper at lower end 444B relative to upper end 442B. Second platen 436 distinguishes from first platen 434 in that second platen 436 does not include notches 450A and 450B. To enable visual inspection of bag assemblies 48 during operation of expressor 430, as discussed below, second platen 436 is commonly formed from a transparent polymer such as acrylic. Although first platen 434 could also be made from a transparent polymer, it is less useful. As such, first platen 434 is commonly made from an opaque material, such as an opaque plastic, or a metal.

Figure 26:
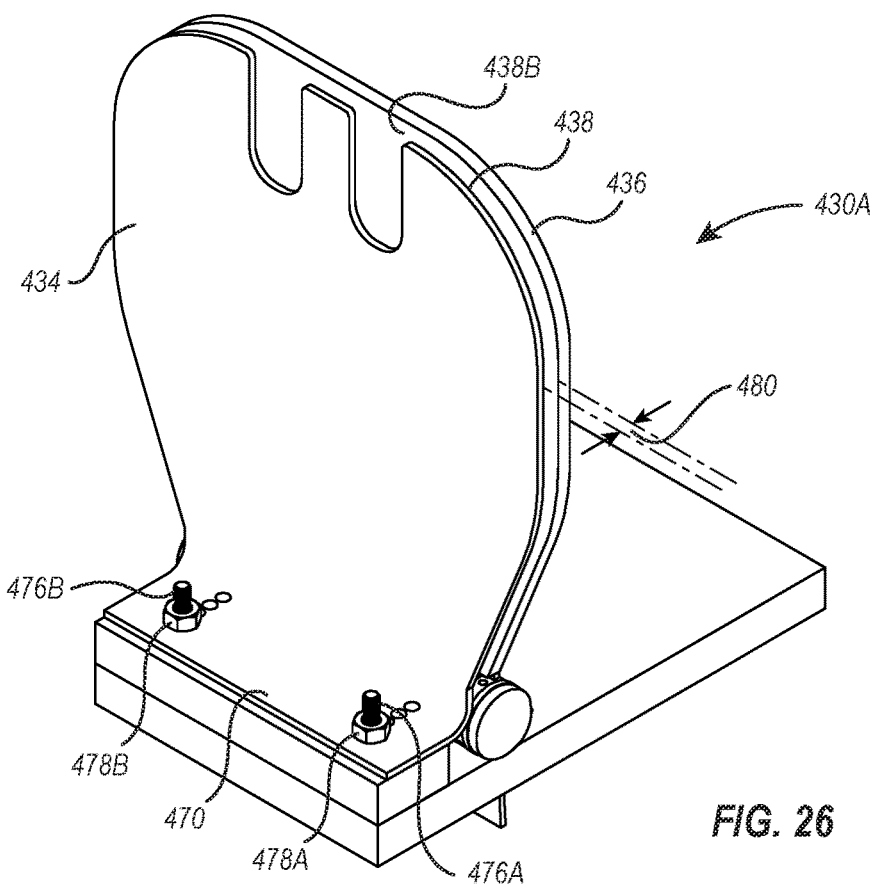
FIG. 26 is a rear perspective view of the expressor shown in FIG. 23 in a collapsed position.

Second platen 436 is movably mounted to base 432 so that second platen 436 can selectively move toward and away from first platen 434. More specifically, second platen 436 is movable between a retracted position, as shown in FIG. 23, where second platen 436 is moved away from first platen 434, and a collapsed position, as shown in FIG. 26, where second platen 436 is moved toward first platen 434. Returning to FIG. 23, a hinge 462 is mounted on base 432, such as by being secured to top surface 456. Lower end 444B of second platen 436 is secured to hinge 462 so that second platen 436 can hingedly pivot between the retracted position and the collapsed position.

In one embodiment of the present disclosure, means is provided for mechanically moving the second platen 436 from the retracted position to the collapsed position. By way of example, a spring 464 is coupled with hinge 462 so as to resiliently urge or bias second platen 436 toward the collapsed position, i.e., toward first platen 434. In alternative embodiments, the means can comprise other convention drive mechanism such as a pneumatic or hydraulic piston, a gear assembly or linkage driven by a motor, or other spring or elastic band configurations. For example, one or more elastic bands could extend between platens 434 and 436 to resiliently urge second platen 436 toward the collapsed position.

An elongated handle 466 projects from outside face 440B of second platen 436 at lower end 444B. A catch 468 is disposed on base 432 at or toward first end 458. Handle 466 is used to manually pivot second platen 436 to the retracted position. Catch 468 can then engage handle 466 to hold second platen 436 in the retracted position. When handle 466 is released from catch 468, second platen 436 resiliently rebounds under the force of spring 464 toward the collapsed position.

Figure 24:
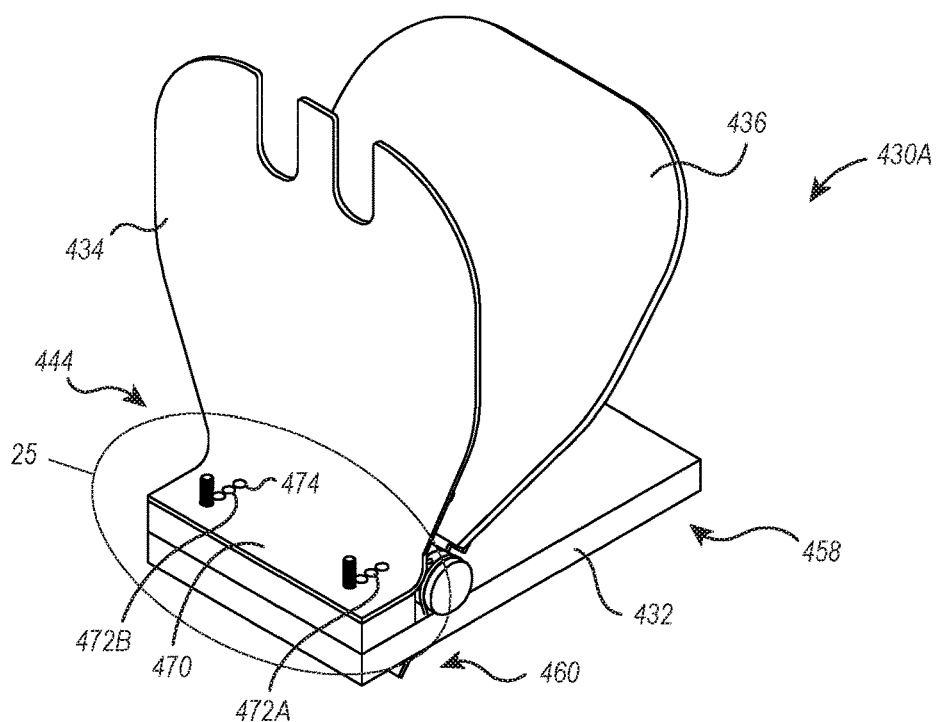
FIG. 24 is a rear perspective view of the expressor shown in FIG. 23.

In one embodiment, first platen 434 can be permanently secured to or integrally formed with base 432. However, in the present embodiment, first platen 434 is adjustably mounted to base 432 so that a gap spacing formed between first platen 434 and second platen 436 can be adjusted. For example, as shown in FIG. 24, a foot 470 outwardly projects from first platen 434 at lower end 444 so as to extend away from second platen 436. In one embodiment, foot 470 can extend orthogonal to first platen 434. Extending through foot 470 are two spaced rows 472A and 472B of a plurality of holes 474. Rows 472A and 472B are in parallel alignment and extend orthogonal to first platen 434. As better shown in FIG. 25, each row 472A and 472B is shown as comprising aligned holes 474A, 474B, 474C and 474D. Other numbers of holes 474, such as at least 2, 3, 4, or 5, can also be used. In the depicted embodiment, each hole 474 is round. However, other configurations can also be used.

Figure 25:
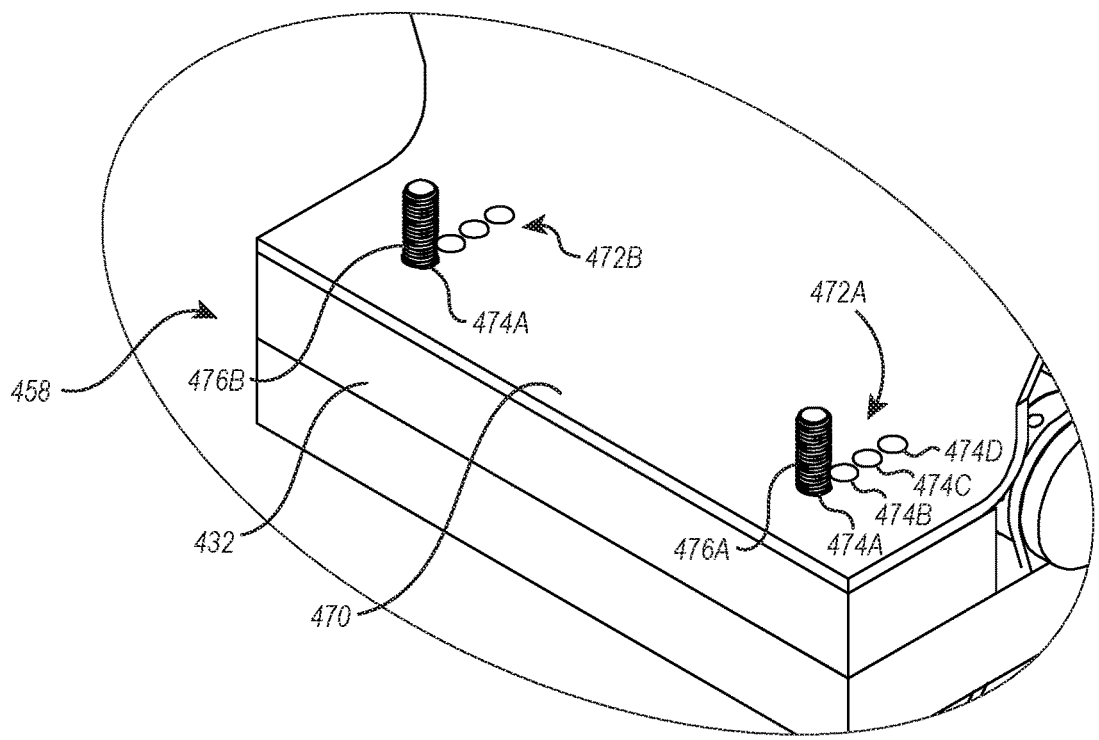
FIG. 25 is an enlarged view of the section 25 identified in FIG. 24.

Upwardly projecting from base 432 at second end 458 are a pair of spaced apart mounting shafts 476A and 476B that are threaded. Mounting shafts 476 are configured to pass through holes 474. For example, as depicted in FIG. 25, mounting shafts 476A and 476B are received within holes 474A of rows 472A and 472B, respectively. In turn, nuts 478A and 478B, as shown in FIG. 26, can be threaded onto mounting shafts 476A and 476B, respectively, so as to bias against foot 470, thereby securely fixing first platen 434 to base 432. With first platen 434 so positioned and second platen 436 moved to the collapsed position, as shown in FIG.

Figure 27:
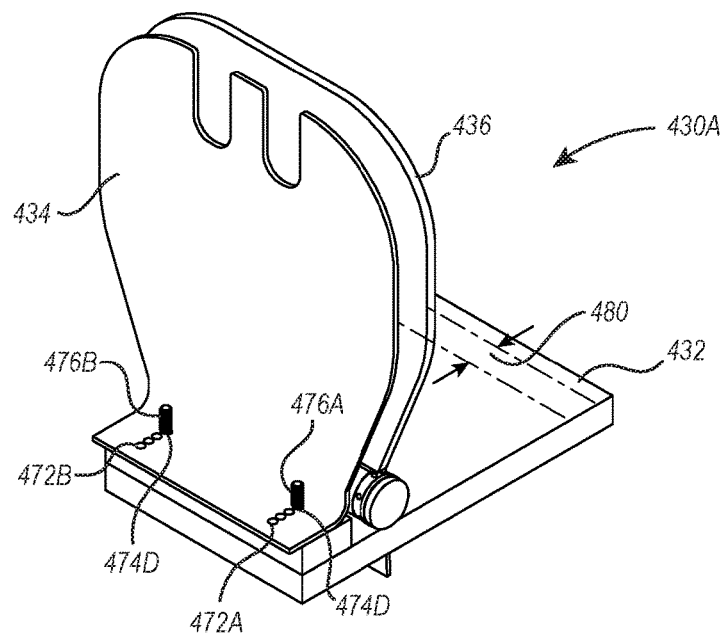
FIG. 27 a rear perspective view of the expressor shown in FIG. 26 with the second platen thereof moved to a second position.

26, a gap spacing 480 is formed between first platen 434 and second platen 436. More specifically, gap spacing 480 is formed between inside face 438 of first platen 434 and inside face 438B of second platen 436. With second platen 436 in the collapsed position, as shown in FIG. 26, inside faces 438 and 438B of platens 434 and 436 are typically disposed in parallel alignment.

Where it is desired to increase the width of gap spacing 480, nuts 478 can be removed and first platen 434 raised vertically off of mounting shafts 476. First platen 434 can then be repositioned so that mounting shafts 476 are positioned within one of the other holes 474B-474D of foot 470 that are closer to first platen 434. For example, as shown in FIG. 27, mounting shafts 476 are now placed within holes 474D of rows 472A and 472B. Nuts 478 (FIG. 26) can again be threaded onto mounting shafts 476 so as to bias against foot 470 and thereby securely fix first platen 434 to base 432. In this second position of first platen 434, gap spacing 480 is now larger than when first platen 434 was in the first position shown in FIG. 26. Accordingly, by selectively moving mounting shafts 476 to different holes 474, the width of gap spacing 480 can be selectively adjusted and set to a desired value. In one embodiment, expressor 430A can be configured so that gap spacing 480 can be selectively adjusted by an amount of at least 0.5 cm, 1 cm, 2 cm, 3 cm or 4 cm or in a range between any two of the foregoing values. Furthermore, gap spacing 480 is typically at least 0.5 cm, 1 cm, 2 cm, 3 cm or 4 cm or is a range between any two of the foregoing values. The benefit of being able to adjust and/or set the width of gap spacing 480 will be discussed below in greater detail.

The use of mounting shafts 476 and holes 474 is one example of means for selectively adjusting the width of gap spacing 480 between platens 434 and 436. However, it is appreciated that a variety of other mechanism can likewise be used to selectively adjust the width of gap spacing 480 between platens 434 and 436. By way of example and not by limitation, separate holes 474 of each row 472 could be replaced with elongated channels through which mounting shafts 476 can slide. Separate holes 474 of each row 472 could also be moved together and interconnected to form elongated slots having discrete locations where mounting shafts 476 can pass. In other embodiments, mounting shafts 476 can be removed from base 432. Bolts, screws or other fasteners could be passed down through select holes 474 or channels formed on foot 470 and secured into base 432 for adjusting gap spacing 480. In yet other embodiments, mounting shafts 476 and holes 474 can be replaced with one or more clamps, latches, catches, or other types of releasable fasteners for adjusting gap spacing 480.

Figure 28:
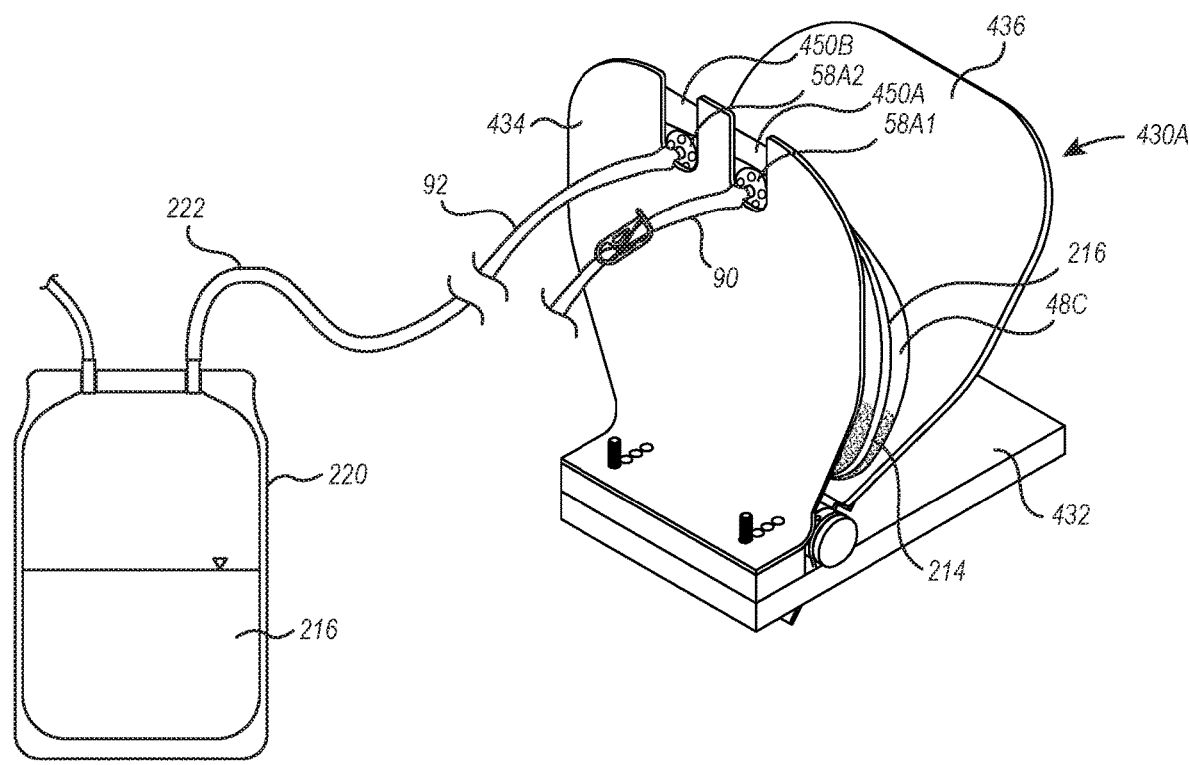
FIG. 28 is a perspective view of the expressor shown in FIG. 24 compressing the bag assembly shown in FIG. 6 that is coupled to a container.

As an alternative to using pump 224 (FIG. 22), expressor 430A can be used to drive supernatant 216 from bag assemblies 48 into container 220. For example, as depicted in FIG. 28, once suspension 18 within bag assemblies 48 is separated into pellets 214 and supernatant 216, outlet line 92 of bag assemblies 48 is fluid coupled to inlet line 222 of container 220 or can be directly coupled to container 220 using any conventional method, such as those previously discussed. Either prior to or after fluid coupling bag assembly 48 to container 220, bag assembly 48 is removed from bucket 124 and, where applicable, insert 166 can also be removed. With second platen 434 in the retracted position, bag assembly 48 is then positioned between first platen 434 and second platen 436. Although any of the bag assemblies 48 disclosed or envisioned herein can be used with expressor 430A, bag assembly 48C is shown in FIG. 28. In this assembly, ports 58A1 and 58B1 can be aligned with notches 450A and 450B so that inlet line 90 or outlet line 92 pass therethrough, respectively. Notches 450 function in part to prevent damage to port 58 and kinking of lines 90 and 92 during operation of expressor 430A.

Once bag assembly 48 is properly positioned on expressor 430A and fluid coupled with container 220, second platen 436 can be moved toward first platen 434 so that bag assembly 48 is compressed between platens 434 and 436, thereby driving/forcing the supernatant 216 to flow out of bag assembly 48, through outlet line 92 and into container 220. More specifically, once bag assembly 48 is properly positioned on expressor 430A and fluid coupled with container 220, handle 466 (FIG. 23) can be released from catch 468 which enables second platen 436 to move toward the collapsed position, i.e., toward the first platen 434, under the force of spring 464 by pivoting about hinge 462. The compressing of bag assembly 48 between platens 434 and 436 under the force of spring 464 drives/forces the supernatant 216 to flow out of bag assembly 48, through outlet line 92 and into container 220.

In one method of use, the width of gap spacing 480 (FIG. 27) is selectively adjusted prior to use so that as second platen 436 moves to the final collapsed position, pellet 214 is pancaked so as to spread out within bag assembly 48 by being compressed between platens 434 and 436 (FIG. 28). The pancaking and spreading pellet 214 further drives supernatant 216 out of bag assembly 48 and into container 220. However, gap spacing 480 is typically set so that no portion of pellet 214 flows out of bag assembly 48 and into container 220. That is, gap spacing 480 is set so that when second platen 436 reaches its collapsed position so that second platen 436 is no longer advancing toward first platen 434, the pancaked pellet 214 fills bag assembly 48 up toward port 50B1 but does not reach port 50B1. As such, pellet 214 cannot flow into outlet line 92. Rather, pancaked pellet 214 only extends up to a level below ports 58 so that some supernatant 216 remains within bag assembly 48 and occupies the volume between the top of pancaked pellet 214 and ports 58. Typically, gap spacing 480 is sized to that between 25 ml and 150 ml and more commonly between 50 ml and 100 ml of supernatant 216 remains within bag assembly 48 when second platen 436 has reached its final collapsed position.

The amount of pellet 214 within a bag assembly 48 can vary dependent upon a number of different factors, including the volume percentage of cells in suspension 18 withdrawn from the bioreactor and fed into bag assembly 48. As such, the ability to selectively adjust gap spacing 480 dependent upon the quantity of pellet 214 within a bag assembly 48 has the benefit of enabling expressor 430A to freely and independently operate to transfer supernatant 216 to container 220 with decreased risk of any of pellet 214 flowing into container 220. Thus, one of benefit of using expressor 430A is that less monitoring is required during removal of supernatant 216.

As discussed below in more detail, where it is desired to collect and further process and use supernatant 216, it is desirable to prevent any of pellet 214 from flowing into container 220, as discussed above. However, where supernatant 216 is not being used but rather pellet 214 is being collected for further use, it is less critical whether a portion of pellet 214 flow into container 220. For example, it may be desirable to set gap spacing 480 so that a small portion of pellet 214 flow into container 220, thereby helping to ensure that a maximum quantity of supernatant has been removed from bag assembly 48.

Figure 29:
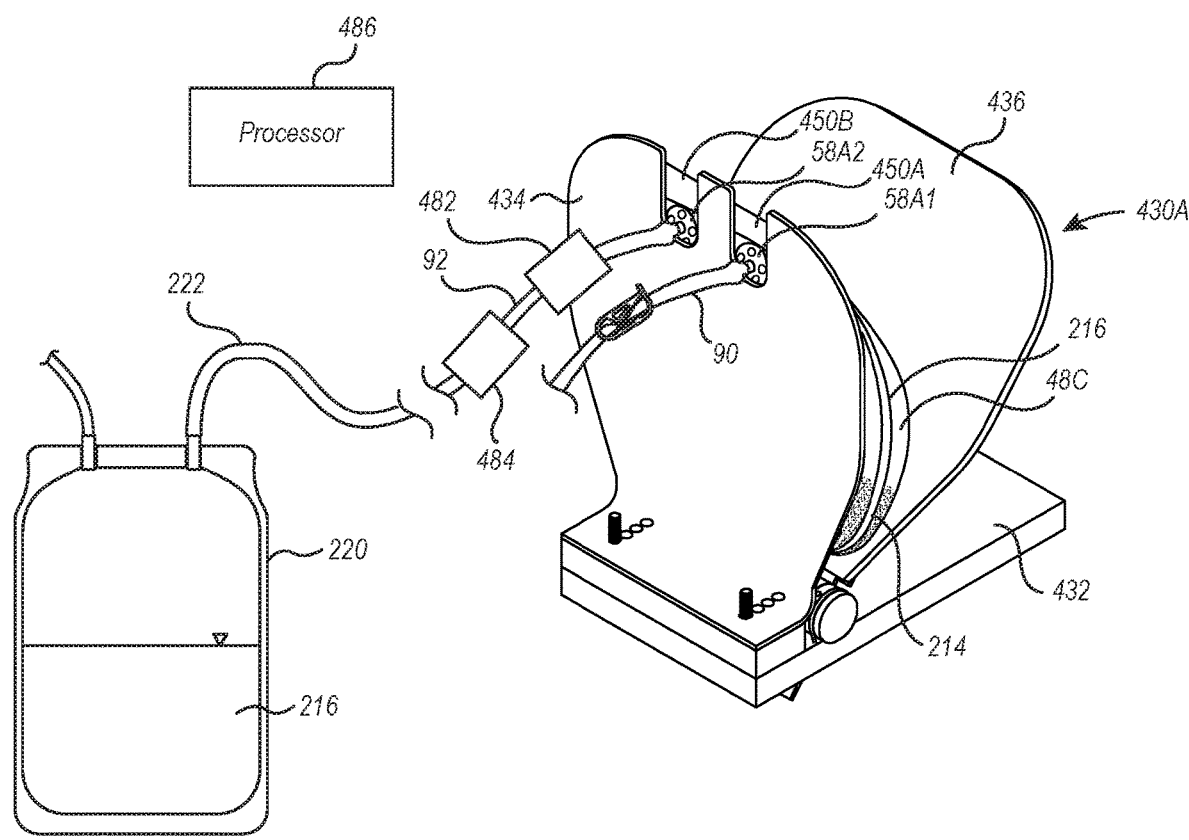
FIG. 29 is a perspective view of the assembly shown in FIG. 28 being used with an optical sensor, an electronic pinch clamp and a processor.

Independent of or in combination with adjusting gap spacing 480 to prevent the unwanted removal of pellet 214 from bag assembly 48, other mechanisms can also be used to prevent the flow of pellet 214 into container 220. For example, as depicted in FIG. 29, outlet line 92 can have an optical sensor 482 overlaying outlet line 92 and an electric pinch clamp 484 overlying outlet line 92 down stream of optical sensor 482. Optical sensor 482 and pinch clamp 484 can be electronically controlled by a processor 486. During operation, while expressor 430A is driving supernatant 216 from bag assembly 48 to container 220, optical sensor 482 in combination with processor 486 monitors the clarity or density of the fluid flowing through outlet line 92.

If processor 486 detects that the fluid flowing through outlet line 92 is starting to become less clear, i.e., more opaque, or has an increase in density, both of which can be signs that a portion of pellet 214 is starting to flow through outlet line 92, processor 486 operates pinch clamp 484 to close outlet line 92, thereby preventing any of pellet 214 from flowing into container 220. Where second platen 436 is begin moved by a motor, as opposed to a resilient spring, processor 486 could also function to simply turn off the motor based on signals from optical sensor 482, thereby again helping to ensure that no portion of pellet 214 reaches container 220. It is further appreciated that processor 486, optical sensor 482 and pinch clamp 484 can be used with the pump assembly discussed above with regard to FIG. 22. That is, based on signals from optical sensor 482 overlying outlet line 92, processor 486 can be used to turn off pump 224 and/or close outlet line 92 using pinch clamp 484 to prevent the flow of pellet into container 220.

Where pellet 214 is fragile, further precautionary steps can be taken to prevent disturbing and resuspending portions of pellet 214 as supernatant 216 is removed. For example, as shown in FIG. 22, outlet line 92 of bag assembly 48 is again coupled with container 220 through a sterile connection. As previously discussed with regard to FIG. 22, this can be through a direct coupling with container 220 or through inlet line 222 coupled with container 220. This coupling is typically accomplished while bag assembly 48 remains disposed within bucket 124 and/or insert 166. Alternatively, either before or after fluid coupling bag assembly 48 with container 220, bag assembly 48 can be removed from bucket 124, insert 166 or other centrifuge rotor. Again, however, bag assembly 48 is typically secured in an upright position such as by being hung on a rack or supported on a stand or within a container.

Figure 30:
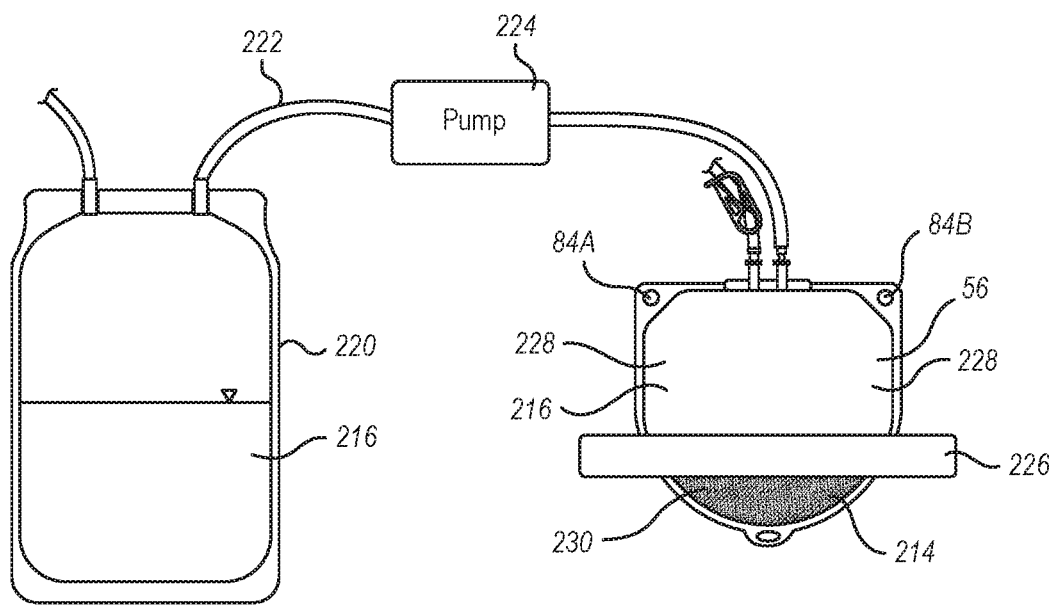
FIG. 30 is an elevated front view of the bag assembly shown in FIG. 21 having a clamp mounted thereon and being coupled with a container in which the supernatant is being pumped.

Once bag assembly 48 is fluid coupled within container 220, a portion of supernatant 216 is then dispensed out of bag assembly 48 and into container 220. As previously discussed, this can be accomplished by either using pump 224, as shown in FIG. 22, or by using expressor 430, as shown in FIG. 28. With the portion of supernatant 216 removed, a clamp 226 is then clamped over bag assembly 48 directly above pellet 214 as depicted in FIG. 30. If not previously done, attachment of clamp 226 requires that bag assembly 48 be removed from bucket 124, insert 166, or any other structure that would obstruct the attachment of clamp 226. However, clamp 226 can be attached while bag assembly 48 is suspended.

Clamp 226 functions to divide compartment 56 into an upper compartment 228 that houses supernatant 216 and a lower compartment 230 that houses pellet 214. Again, pellet 214 has a higher density than supernatant 216 and can have a higher viscosity. That is, clamp 226 is applied so that upper compartment holds a first component and lower compartment holds a second component where the second component has a higher density and/or viscosity than the first component. It is appreciated that a small amount of supernatant 216 may be permitted to be retained within lower compartment 230 to minimize disruption of pellet 214 as clamp 226 is attached. Clamp 226 functions to seal upper compartment 228 from lower compartment 230 so that no portion of pellet 214 can pass into upper compartment 228. Accordingly, once clamp 226 has been applied, bag assembly 48 can be handled without fear of disrupting pellet 214 or resuspending pellet 214 into supernatant 216.

The above discusses removing a portion of supernatant 216 from bag assembly 48 prior to the attachment of clamp 226. This is because bag assembly 48 is typically sufficiently full that clamp 226 cannot be attached to divide compartment 56 into upper compartment 228 and lower compartment 230 until a portion of supernatant 216 has first been removed. Accordingly, the amount of supernatant 216 that needs to first be removed before clamp 226 is attached is the amount necessary to enable the attachment of clamp 226. Alternatively, in situations where bag assembly 48 is not full and clamp 226 can be attached without first removing any supernatant 216, the initial step of first removing the portion of supernatant 216 before attaching clamp 226 can be eliminated.

Figure 31:
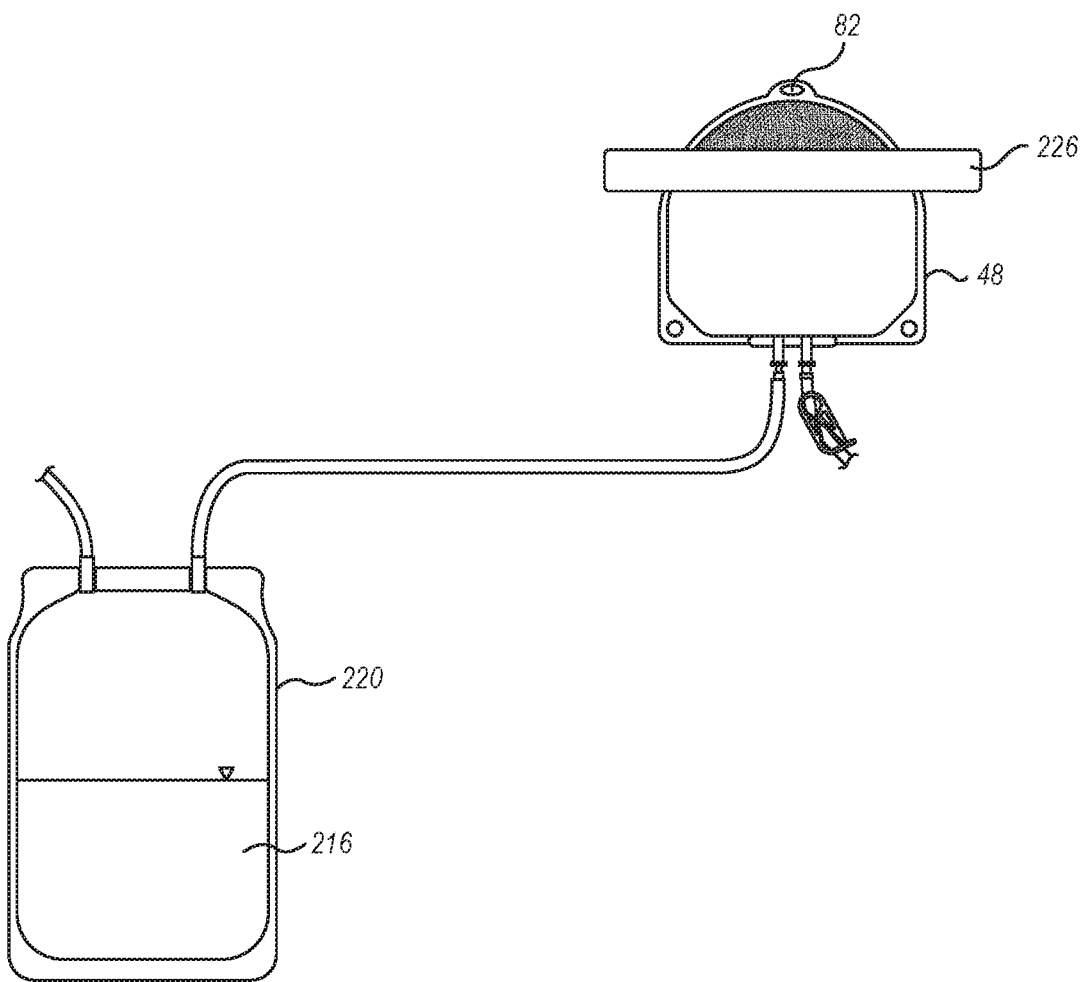
FIG. 31 is an elevated front view of the bag assembly shown in FIG. 30 where the supernatant is being drained into a separate container.

Once clamp 226 is attached, bag assembly 48 can continue to be maintained as previously supported or can then be secured to a rack, support container, stand, or the like or can simply be laid flat on a table or other support structure. Pump 224 can then be used for pumping the remainder of supernatant 216 from upper compartment 228 into container 220. Alternatively, to avoid using pump 224, bag assembly 48 can be inverted at an elevation above container 220, as depicted in FIG. 31, so that the supernatant 216 can freely drain into container 220. In yet another alternative, as discussed below, an alternative expressor could also be used to dispense supernatant 216 from upper compartment 228.

The above method discusses using clamp 226 to seal upper compartment 228 from lower compartment 230 so as to isolate supernatant 216 from pellet 214. In alternative embodiments, however, other methods can be used to form and seal upper compartment 228 from lower compartment 230. For example, bag assembly 48 could be temporarily pinched closed along the same line that clamp 226 is attached. This can be accomplished by pressing together structural members on opposing sides of bag assembly 48 along the clamp line so as to seal upper compartment 228 from lower compartment 230. In another alternative, bag assembly 48 could be permanently welded closed along the clamp line so to seal upper compartment 228 from lower compartment 230. Again, once upper compartment 228 is isolated from lower compartment 230, supernatant 216 can be dispensed into container 220 without risk of resuspending pellet 214 into supernatant 216.

Figure 32:
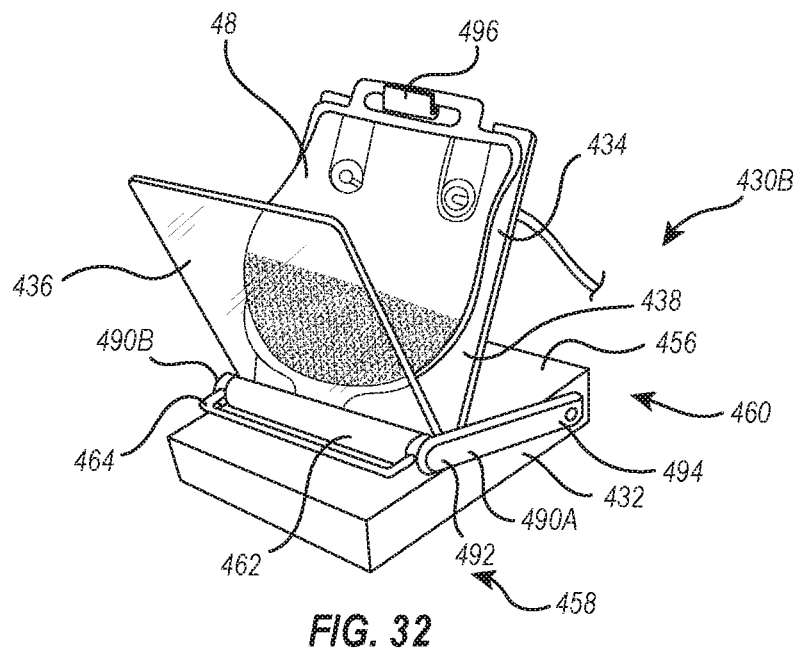
FIG. 32 is a front perspective view of an alternative embodiment of an expressor supporting the bag assembly of FIG. 6.
Figure 33:
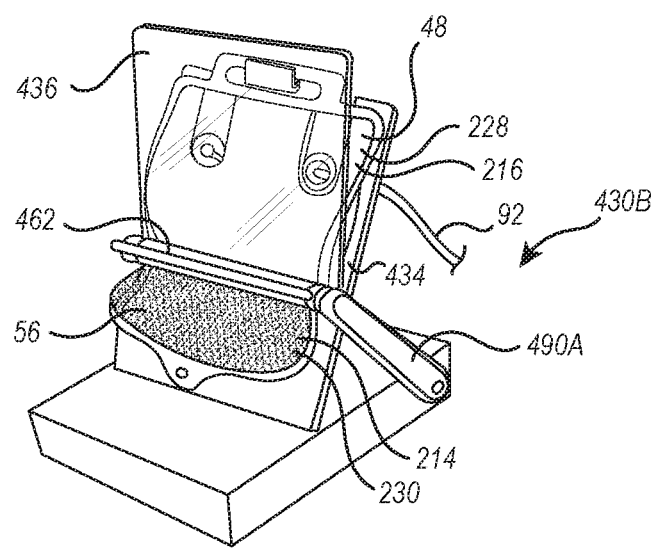
FIG. 33 is a front perspective view of the expressor of FIG. 32 compressing the bag assembly.

Depicted in FIGS. 32 and 33 is an embodiment of an expressor 430B, which, unlike the expressor 430A described above, functions to seal upper compartment 228 from lower compartment 230 prior to removal of supernatant 216. Except as noted below, expressors 430A and 430B operate in substantially the same way and like elements between expressors 430A and 430B are identified by like reference characters. Expressor 430B includes base 432 having top surface 456. Upstanding from base 432 is first platen 434. Although first platen 434 could extend orthogonal to base 432, in this embodiment first platen 434 is sloped to form an outside angle between first platen 434 and top surface 456 of base 432 that is greater than 90°. Expressor 430B also includes second platen 436 having a lower end coupled to hinge 462. Spring 464 is coupled to hinge 462 and is used to urge rotation of second platen 436 from the retracted position to the collapsed position. However, in contrast to expressor 430A where hinge 462 is directly secured to base 432, expressor 430B includes a pair of elongated arms 490A and 490B each having a first end 492 and an opposing second end 494. Second ends 494 of arms 490 are rotatably mounted on opposing sides of base 432 at or toward second end 460 of base 432. Hinge 462 extends between first ends 492 of arms 490 so that second platen 436 hingedly rotates relative to arms 490.

During operation, bag assembly 48 is supported against inside face 438 of first platen 434 by being suspended from a hanger 496 extending from first platen 434. Next, arms 490 are rotated upward, as shown in FIG. 33, so that hinge 462 compresses bag assembly 48 against first platen 434 directly above pellet 214, thereby divide compartment 56 into upper compartment 228 that houses supernatant 216 and a lower compartment 230 that houses pellet 214. Arms 490 are locked in place so as to secure the seal between compartment 228 and compartment 230. Second platen 436 is then permitted to freely rotate under the force of spring 464 so as to compress the portion of bag assembly 48 bounding compartment 228, thereby driving supernatant 216 out of compartment 228 through outlet line 92, and into container 220 (FIG. 30).

Expressor 430B thus limits the risk of any portion of pellet 214 flowing into container 220 because pellet 214 is sealed off from supernatant 216. Furthermore, because expressor 430B incorporates a clamping feature, expressor 430B avoids the required use of separate clamp 226. Here it is noted that expressor 430B can also be used to replace pump 224 in the method discussed above with regard to FIG. 30. That is, bag assembly 48 with clamp 226 mounted thereon (FIG. 30) can be suspended on first platen 434 using hanger 496 (FIG. 32). Arms 490 can then be rotated upward so that hinge 462 extends across bag assembly 48 just above clamp 226. Second platen 436 can then be moved to the collapsed position that compresses upper compartment 228 and drives supernatant 216 into container 220. Other methods that seal upper compartment 228 from lower compartment 230 can also be used.

In any of the above approaches, it is appreciated that two or more all of the bag assemblies 48 can be consecutively fluid coupled to the same container 220 so that supernatant 216 is pooled in container 220. Alternatively, each bag assembly 48 can be fluid coupled to a separate container 220. Also, in any of the above approaches, once supernatant 216 has been removed from bag assembly 48, a portion of outlet line 92 or inlet line 222 can be welded closed and then cut through the weld so as to separate bag assembly 48 from container 220. Supernatant 216 and pellet 214 can now be separately transported and/or used as desired. In downstream applications, supernatant 216 can be filtered and then one or more components isolated for subsequent use. In other applications, supernatant 216 may have no value and is simply discarded.

Isolated pellets 214 typically have two uses. First, the cells can by lysed and components from the lysate isolated for analysis or for use in producing a product such as a vaccine. Second, the cells can be maintained in a viable state and subsequently used as an inoculum for producing further biological suspensions. Pellets 214 can be either used for their intended application shortly following harvesting or they can be frozen and stored for their intended use in the future. In other applications, pellets 214 may have no value and can simply be discarded.

Figure 34:
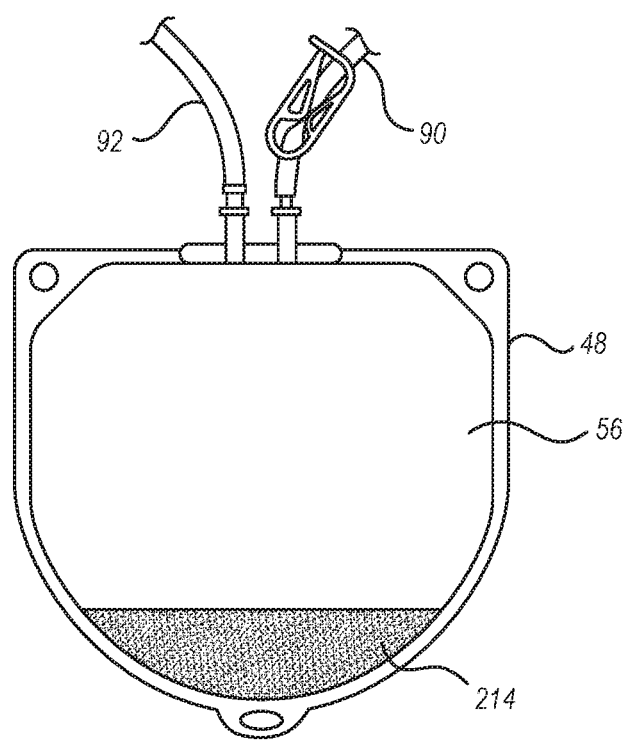
FIG. 34 is an elevated front view of the bag assembly shown in FIG. 30 after the supernatant and clamp have been removed.

Accordingly, with regard to pellet 214, which is now isolated and sealed within compartment 56 of bag assembly 48, as depicted in FIG. 34, clamp 226 or other sealing mechanisms, if used, can now be removed if so desired. Bag assembly 48 which houses pellet 214 therein, but is substantially free of air and other components, can be placed in a freezer for freezing pellet 214 for future use. For example, where the cells are intended to be lysed in the future and viability of the cells is not important, bag assemblies 48 housing pellets 214 can simply be placed in a freezer without further processing. Commonly, bag assembly 48 would be held in a freezer at a temperature of −80° C. or lower.

Alternatively, were the cells may be used as an inoculum in the future, pellets 214 need to be frozen in a manner that will best maintain viability of the cells. This is typically accomplished by delivering a freezing medium into bag assembly 48, such as through a sterile fluid coupling with inlet line 90 or outlet line 92. Pellet 214 and the freezing medium are then mixed together to form a secondary suspension. Bag assemblies 48 containing the secondary suspension can then be placed in a freezer as discussed above for subsequent use.

The freezing medium is commonly known in the art and prevents the growth of ice crystals within the cells that will cause rupturing of the cell walls. A typical freezing medium will comprise glycerin, glycerol, or ethylene glycol mixed with a growth medium. One of the unique benefits of using bag assemblies 48 is that it is easy to resuspend pellet 214. That is, once the freezing medium is added into bag assemblies 48, a user can manually manipulate pellets 214 through the flexibles walls of bag assemblies 48 to efficiently break up pellets 214 and resuspend the cells in the freezing medium, thereby forming the secondary suspension. Other manual or mechanical manipulation of bag assemblies 48, such as folding or shaking, can also be used to form the secondary suspension.

As an alternative to freezing or following freezing, pellets 214 can be removed from bag assemblies 48 for subsequent use. For example, if a pellet 214 has not previously been resuspended in a freezing medium as discussed above, either inlet line 90 or outlet line 92 of the bag assembly 48 can be fluid coupled with a fluid source using a sterile fluid connection. The fluid source is used for delivering a fluid, such as a growth medium, buffer and/or salt solution of similar osmotic pressure to the interior surface of the cells, or other liquid that will not damage the cells, into compartment 56. The fluid and pellet 214 are mixed together, such as by manually manipulating bag assembly 48 and pellet 214 therein, as discussed above, to form a secondary suspension. The secondary suspension can then be pumped, pressed, or drained out of bag assembly 48 through either line 90 or 92 for use or delivery into another container. Any of the methods and apparatus previously described herein can be used for the pumping, pressing or draining of the secondary suspension out of bag assembly 48. Secondary suspension can be used as an inoculum to produce a biological suspension by being delivered into a growth medium located within a reactor, such as reactor 10, or within a smaller container that is functioning as a reactor.

Alternatively, the cells of the secondary suspension can be lysed, either within bag assembly 48 or in a container to which the secondary suspension has been transferred. One or more components of the lysed cells can then be isolated for analysis or use in a product. For example, once secondary suspension has been formed within bag assembly 48 and the cells lysed therein, the bag assembly can again be processed through a centrifuge, using any of the processes described herein, so as to obtain a secondary supernatant and a secondary pellet. The secondary supernatant can then be separated off into another container, using any of the processes described herein, for analysis or use. As an alternative to resuspending pellet 214 within bag assembly 48, bag assembly 48 can simply be cut open and pellet 214 manually removed from compartment 56.

As discussed above, inserts 166 (FIG. 16) can be used with both swinging-bucket rotor 121 (FIG. 11) and fixed angle rotor 121A (FIG. 20) and can be sized to optimize the complementary fit with bag assemblies 48 and/or to minimize stress on and movement of bag assemblies 48. However, inserts 166 also make it easier to load and unload bag assemblies from rotors 121 and 121A. That is, either before or after filling bag assemblies 48 with suspension 18, bag assemblies 48 can be easily properly fitted within cavity 171 of inserts 166. In part, this is because inserts 166 (FIG. 11) are lightweight, easily manipulated, and flexible. Once bag assemblies 48 are fitted within inserts 166, it is then easy to fit the contoured inserts 166 within the cavities of rotors 121 and 121A (FIGS. 16 and 20). That is, it can be easier to first insert bag assemblies 48 into inserts 166 and then place inserts 166 within rotors 121 and 121A than to directly place bag assemblies 48 into rotors 121 and 121A. Following rotation of bag assemblies 48 by centrifuge 112, inserts 166 make it easy to remove bag assemblies 48 from rotors 121 and 121A with minimal disruption to bag assemblies 48 and provide support for bag assemblies 48 outside of rotors 121 and 121A. As such, inserts 166 enable easy movement and placement of bag assemblies 48 with minimal risk of disturbing pellets 214. Furthermore, the use of inserts 166 can decrease production time. For example, where a large number of bag assemblies 48 need to be processed through a centrifuge, a second group of bag assemblies 48 can be placed within inserts 166 while a first group of bag assemblies 48 are being spun in the centrifuge. When the first group of bag assemblies 48 are finished spinning, the use of inserts 166 makes it quick and easy to both remove the first group of bag assemblies 48 from the centrifuge and to insert the second group of bag assemblies in the centrifuge, thereby shortening production time.

Figure 35:
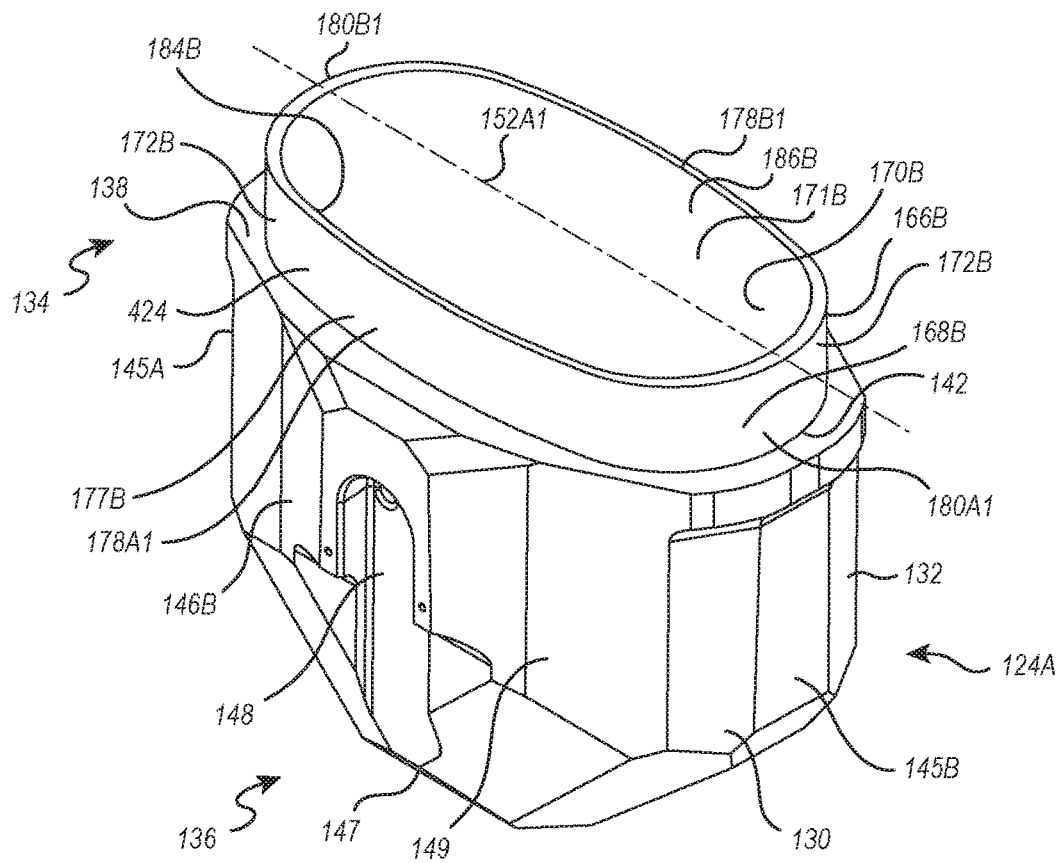
FIG. 35 is a front perspective view of the bucket shown in FIG. 12 having an alternative embodiment of an insert disposed therein.
Figure 36:
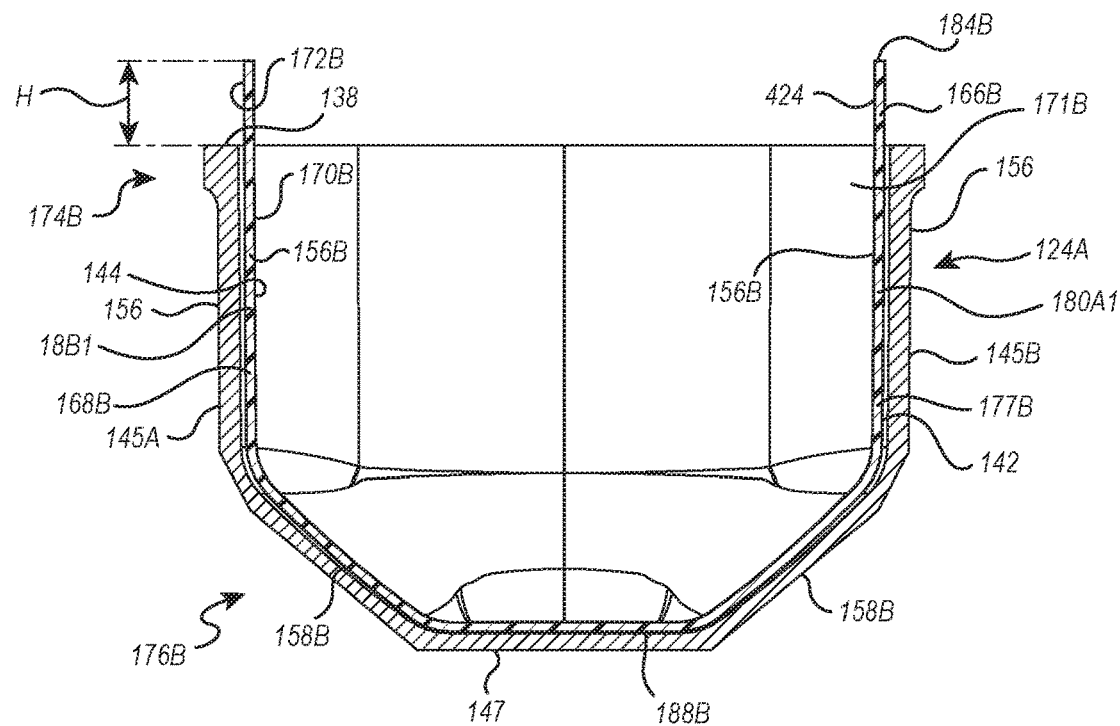
FIG. 36 is a cross sectional side view of the assembly shown in FIG. 35.

In view of the benefits of inserts 166, it is also appreciated that in other applications, inserts 166 need not be thick to provide cushioning properties but can comprise thin liners that simply function to enable easy insertion and removal of bag assemblies 48 into and out of rotors 121 and 121A. In this context, inserts 166 need not be flexible but can be rigid or semi-rigid. For example, depicted in FIGS. 35 and 36 is an insert 166B received within cavity 142 of bucket 124A. Bucket 124A was previously discussed with regard to FIGS. 12-14. Insert 166B has a cupped shaped body 168B having an interior surface 170B and an opposing exterior surface 172B that extend between an upper end 174B and opposing lower end 176B. Body 168B has a floor 188B an encircling perimeter wall 177B upstanding therefrom. Encircling perimeter wall 177B includes opposing side walls 178A1 and 178B1 that extend between opposing end walls 180A1 and 180B1. However, in contrast to having ribs on exterior surface 172B, exterior surface 172B is smooth having a configuration complementary to interior surface 144 of bucket 124A.

Upper end 174B of perimeter wall 177B terminates at an upper end face 184B that encircles an opening 186B to cavity 171B. In this embodiment, interior surface 170B of insert 166B is depicted having the same configuration as interior surface 144 of bucket 124A. As such, cavity 171B has the same configuration as cavity 142 of buckets 124A. Specifically, cavity 171B of insert 166B is elongated having a longitudinal axis 152A1 that extends between opposing end walls 180A1 and 180B1. Cavity 171B has a transverse cross section that is oval or elliptical and that inwardly tapers as it extends from upper end 174B to lower end 176B.

The prior discussion of interior surface 144 of bucket 124A and the alternatives thereto is also applicable to and is incorporated herein as a description of interior surface 170B of insert 166B. For example, end walls 180A1 and 180B1 inwardly taper as they extend from upper end 174B to lower end 176B. More specifically, end walls 180A1 and 180B1 each include an upper section 156B at upper end 174B and a lower section 158B at lower end 176B. In the depicted embodiment, upper section 156B of opposing ends walls 180A1 and 180B1, particularly interior surfaces 170B thereof, are disposed in parallel alignment. Expressed in other terms, interior surfaces 170B of upper sections 156B can be perpendicular to interior surface 170B of floor 188B. In contrast, lower sections 158B of end walls 180A1 and 180B1, and particularly interior surfaces 170B thereof, can inwardly taper from corresponding upper sections 156B to floor 188B.

In one embodiment, interior surface 170B of floor 188B can intersect with interior surface 170B of lower sections 158B to form an inside angle between 110° and 170° with between 130° and 150° being more common. Other angles can also be used. In alternatives to the above, interior surface 170B of lower sections 158B could outwardly curve between floor 188B and upper sections 156B. Furthermore, upper sections 156B need not be parallel but could outwardly flare at an angle less than what lower sections 158B extend. In still other embodiments, interior surface 170B of upper sections 156B can extend in a curve and both upper sections 156B and lower sections 158B can extend in a curve. Other configurations can also be used that result in cavity 171B having an inward taper as cavity 171B extends from upper end 174B to lower end 176B.

Figure 37:
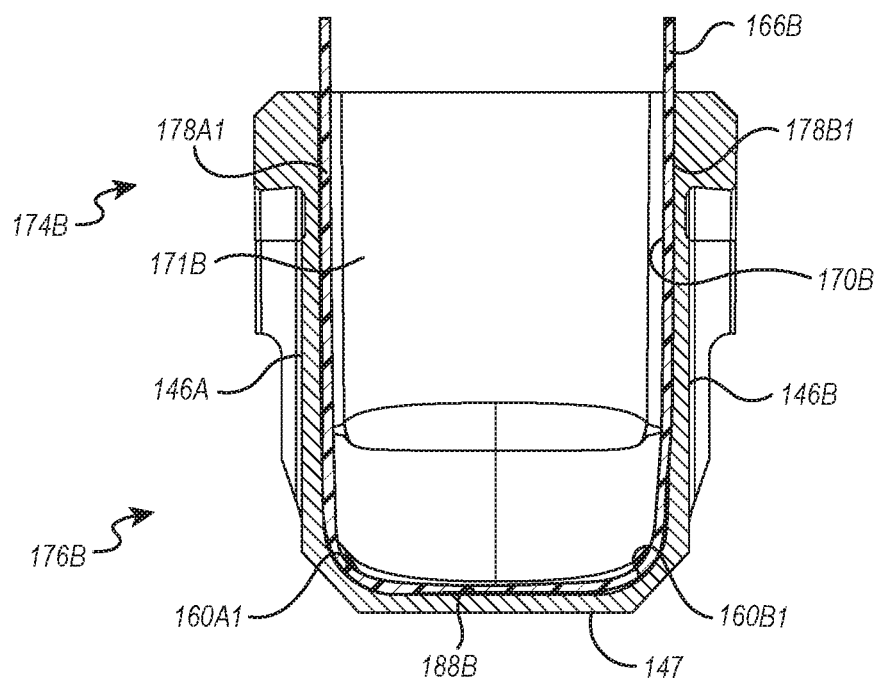
FIG. 37 is a cross sectional front view of the assembly shown in FIG. 35.

Turning to FIG. 37, interior surfaces 170B of opposing side walls 178A1 and 178B1 are disposed parallel to each other and perpendicular to interior surface 170B of floor 188B. However, inwardly curved corners 160A1 and 160B1 are formed at the intersection between floor 188B and side walls 178A1 and 178B1, respectively. Corners 160A1 and 160B1 give an inward tapering to cavity 171B at lower end 176B. In alternative embodiments, interior surfaces 170B of opposing side walls 178A1 and 178B1 could also flare outward away from floor 188B either linearly or in a curve. Again, such a configuration results in cavity 171B having an inward taper as it extends from upper end 174B to lower end 176B.

Interior surface 170B of insert 166B is contoured so that cavity 171B has a configuration that is generally complementary to bag assemblies 48 when bag assemblies 48 are filled with suspension. As previously discussed with buckets 124A, this contouring has a number of benefits that are also applicable to insert 166B. In addition, with reference to FIG. 35, insert 166B is configured so that when fully nested within cavity 142 of bucket 124A, insert 166B has an annular lip portion 424 that projects out of cavity 142 above upper end face 138 of bucket 124A. Annular lip portion 424 is in the form of an annular sleeve. Annular lip portion 424 has a height H (FIG. 36) extending from upper end face 138 of bucket 124A to upper end face 184B of insert 166B that is typically at least 0.5 cm, 1 cm, 2 cm, 3 cm, 4 cm or 5 cm or is in a range between any two of the foregoing values.

The formation of annular lip portion 424 achieves a number of benefits. For example, annular lip portion 424 makes it easy for an operator to manually grasp insert 166B, either with or without bag assembly 48 disposed within cavity 171B thereof, for both inserting insert 166B into cavity 142 of bucket 124A, such as prior to centrifugation, and removing insert 166B from cavity 142 of bucket 124A, such as after centrifugation. That is, because annular lip portion 424 always freely projects out of cavity 142 of bucket 124A, an operator can easily grasp lip portion 424 for select insertion of insert 166B into or removal of insert 166B out of cavity 142 of bucket 124A. The same is true for the insertion and removal of insert 166B from cavities 200 of fixed angle rotor 121A (FIG. 20).

Furthermore, the upwardly extending annular lip portion 424 helps to retain bag assemblies 48 and suspension 18 therein within cavity 142 of bucket 124A. More specifically, if a portion of bag assembly 48 and suspension 18 housed therein moves out of cavity 142 of bucket 124A during centrifugation, forces applied to the bag assembly can result in failure of bag assembly 48 and loss of suspension 18 therein. Annular lip portion 424 helps to retain bag assemblies 48 and suspension 18 housed therein within cavity 142 of bucket 124A to prevent such failure and loss.

Figure 38:
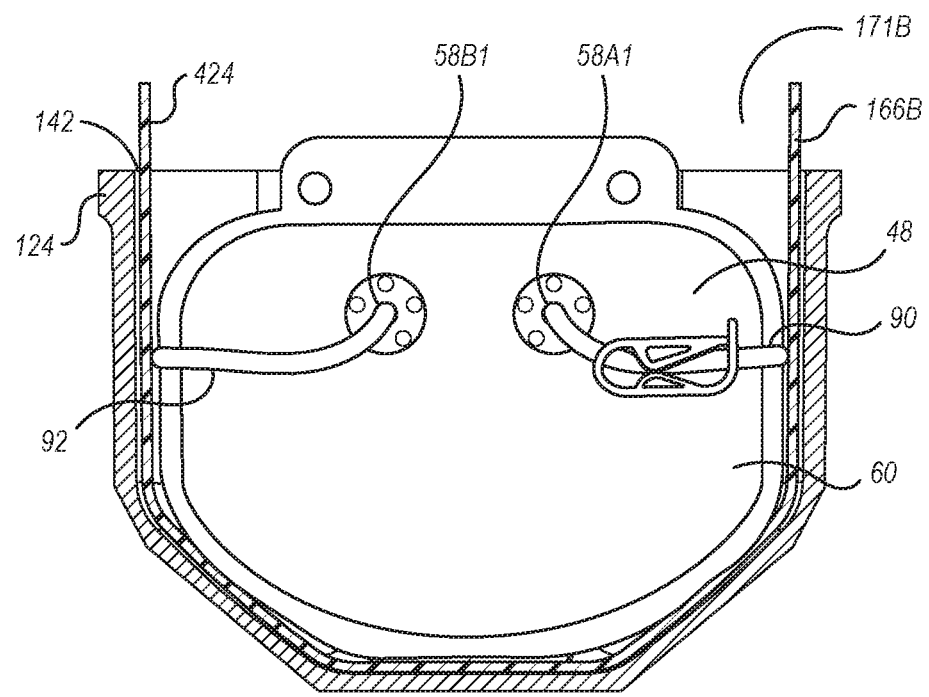
FIG. 38 is the cross sectional side view of the assembly shown in FIG. 36 having the bag assembly shown in FIG. 6 disposed therein.

Furthermore, the added space provided by annular lip portion 424 enables inlet line 90, outlet line 92, and clamp 55 to be easily and securely stored within cavity 171B of insert 166B during centrifugation, such as shown in FIG. 38. Again, should lines 90 or 92 move out of cavity 142 of bucket 124A during centrifugation, applied force could result in leakage or failure of bag assemblies 48. The above benefits also apply to using insert 166B in cavities 200 of fixed angle rotor 121A (FIG. 20).

Here it is also noted that securing ports 58A1 and 58B1 on the face of first sheet 60 of bag assembly 48, as opposed to welding ports 58A and 58B between first sheet 60 and second sheet 62 (FIG. 3), makes it easier to store bag assembly 48 and lines 90 and 92 within an insert, bucket, or rotor with decreased risk of lines 90 or 92 coming out of the insert, bucket, or rotor during centrifugation. That is, because lines 90 and 92 project horizontally off of ports 58A1 and 58B1 into the insert, bucket or rotor, as opposed to projecting vertically, lines 90 and 92 are more easily placed and retained within the insert, bucket or rotor. Finally, the use of annular lip portions 424 can enable the processing of a larger volume of suspension 18 within each bucket or rotor, thereby decreasing production time.

Larger heights H of lip portion 424 improve the ability to achieve the above benefits. However, if lip portion 424 gets too large, it can interfere with operation of the centrifuge. Thus, the height H is in part dependent on the centrifuge being used.

As previously mentioned, insert 166B (shown in FIGS. 35-38) is distinguished from insert 166 (shown in FIG. 16) in that insert 166B is not configured to function as a cushion for bag assemblies 48 but rather primarily functions for easy handling and safe processing of bag assemblies 48. To that end, insert 166B could be made of the same polymeric material as bucket 124. Often, however, inserts 166B are made of a polymeric material such as polypropylene, polyallomer, or polycarbonate. Other materials can also be used. The material and thickness thereof is typically selected so that there is either no compression of the thickness or no significant compression of the thickness, e.g., less than 5% and more commonly less than 2% or 1%. The maximum thickness of insert 166B, i.e., the distance between interior surface 170B and 172B, is typically less than 1 cm and more commonly less than 0.5 cm, 0.25 cm or 0.1 cm. In one embodiment, insert 166 has a thickness extending between the interior surface and exterior surface thereof, insert 166 being sufficiently flexible that the thickness can be manually compressed between the fingers of an operator. In contrast, insert 166B has a thickness extending between the interior surface and the exterior surface thereof, insert 166B being sufficiently rigid that the thickness cannot be manually compressed between the fingers of an operator. By decreasing the thickness of insert 166B, a larger volume of suspension 18 can be processed within each bucket 124A, thereby decreasing production time. It is also appreciated that inserts 166B can have some flexibility. For example, in some embodiments, opposing side walls 178A1 and 178B1 can be manually pressed together to be touching at upper end 174B without plastic deformation of insert 166B.

Here it is noted that all discussions herein with regard to placing a bag assembly and/or insert within the cavity of a bucket of a rotor of a centrifuge should also be construed as and provide support for, including support for claim language, of the broader concept of placing the bag assembly within the cavity of the rotor of the centrifuge.

Figure 39:
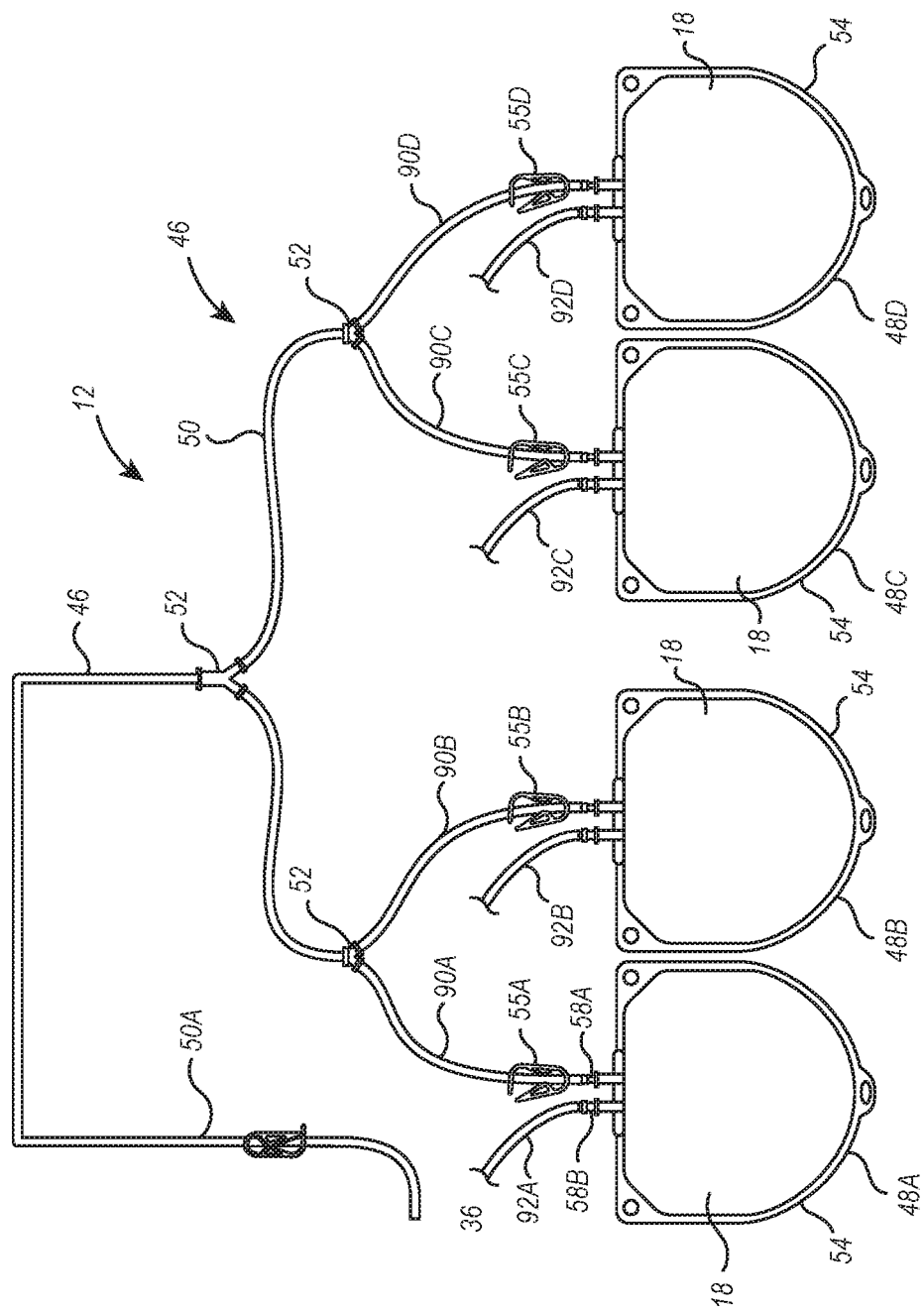
FIG. 39 is an elevated front view of the manifold system shown in FIG. 1 separated from the reactor for positioning within a centrifuge.

It is appreciated that the above described methods of separating and harvesting the components of suspension 18 can also be done in a variety of other method steps. For example, in contrast to separating bag assemblies 48 from manifold 46 (FIG. 1) prior to centrifugation of bag assemblies 48, manifold 46 can remain fluid coupled with bag assemblies 48 during centrifugation. That is, after bag assembles 48 are filled with suspension 18, as previously discussed, the entire manifold system 12, i.e., the combination of manifold 46 and bag assemblies 48, (FIG. 1) can be separated from container 14 such as by welding and cutting the fluid line 50A coupled within container 14 of reactor 10. One embodiment of the separated manifold system 12 is depicted in FIG. 39. It is appreciated that bag assemblies 48 of manifold system 12 can be of any of the configurations disclosed herein and can include any number of bag assemblies 48, including at least 2, 4, 6, 8, or 10 bag assemblies. In addition, manifold 46 can be configured to fluid couple together bag assemblies 48 in any desired configuration including in series, in parallel, or in combinations thereof. Clamps 55 can be used to selectively control flow of fluid into and out of each bag assembly 48 through fluid line 50A.

Figure 40:
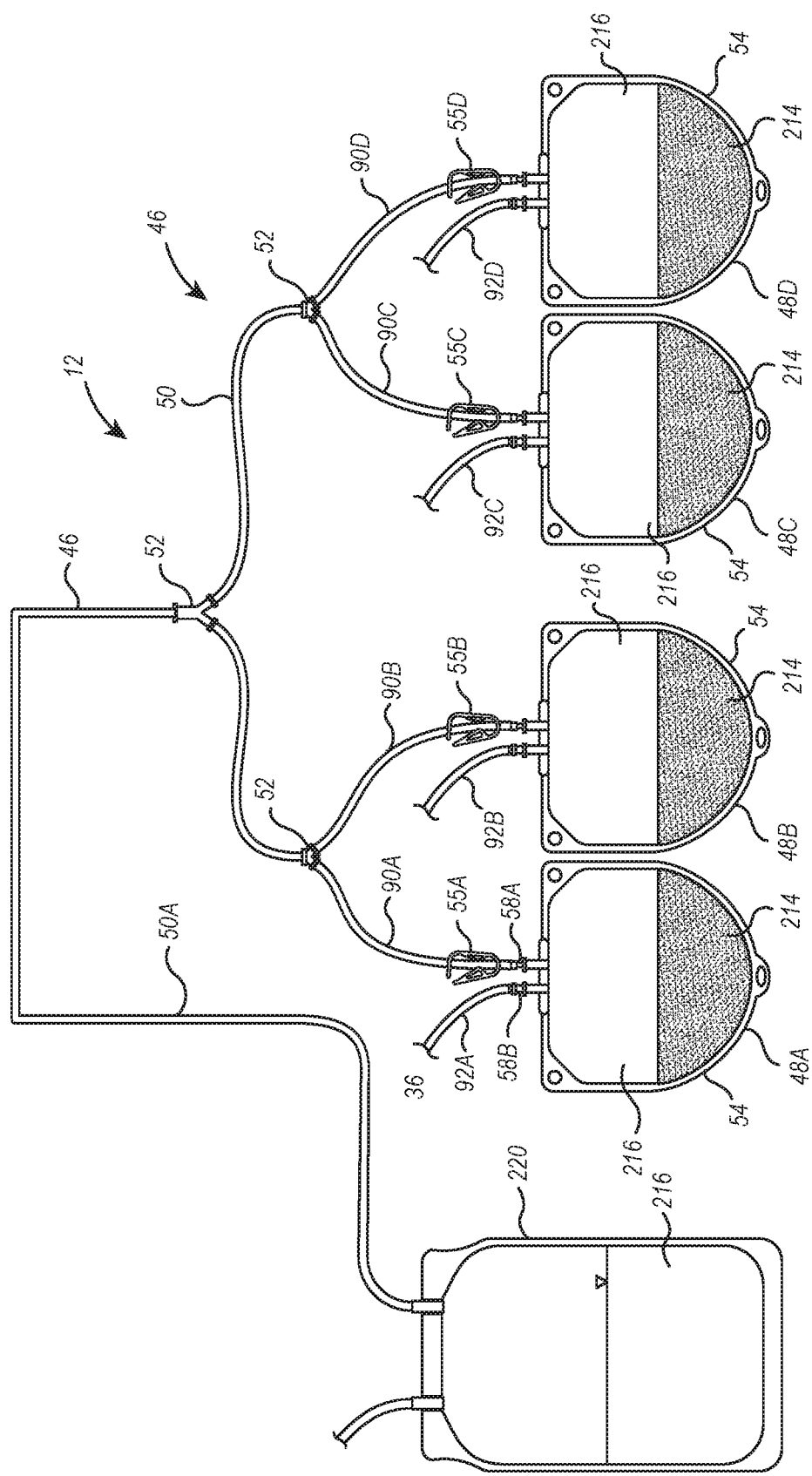
FIG. 40 is an elevated front view of the manifold system shown in FIG. 39 coupled to a container after removal from a centrifuge.

Next, manifold system 12 is spun by a centrifuge to separate suspension 18 in each of bag assemblies 48 into a pellet and supernatant. Specifically, bag assemblies 48, while fluid coupled with manifold 46, are received within cavities 142 of swinging-bucket rotor 121 (FIG. 11) or cavities 200 of fixed angle rotor 121A (FIG. 19), either directly or in conjunction with inserts 166 (FIGS. 16, 20, and 38). As previously discussed, bag assemblies 48 can be received within cavities 142 or 200 either prior to or after filling bag assemblies 48 with suspension 18. However, in this embodiment, manifold 46 remains coupled with bag assemblies 48 as rotors 121 or 121A are received within cavity 116 of centrifuge 112 (FIG. 9) and rotated. In this method, manifold 46 can be removably secured, such as by clamps, ties, fasteners or the like, to rotor body 122 (FIG. 11) of swinging bucket rotor 121 or body 196 (FIG. 19) of fixed angle rotor 121A prior to rotation. As depicted in FIG. 40, after rotation by centrifuge 112 so that suspension 18 is separated into pellets 214 and supernatant 216, fluid line 50A can be fluid coupled to container 220, such as by tube welding or any of the other techniques disclosed herein.

The same processes discussed herein, i.e., with or without applying clamp 226 (FIG. 30), can then be used to transfer supernatant 216 from each bag assembly 48, through manifold 46 and into container 220. For example, supernatant 216 can be transferred to container 220 by draining under gravity (such as in FIG. 31), applying pump 224 to fluid line 50A (such as in FIGS. 22 and 30) and/or by applying an expressor 430 to each bag assembly 48 (such as in FIGS. 28, 29, and 33). If desired, clamps 55 can be selectively opened or closed to isolate bag assemblies 48 as supernatant 216 is consecutively transferred from each bag assembly 48 to container 220.

Once supernatant 216 is removed from each bag assembly 48, pellets 214 can, if desired, also be removed using the same methods discussed herein. For example, fluid line 50A could be cut from container 220 and then fluid coupled with a fluid source for delivering fluid back into each bag assembly 48 for resuspending pellets 214. In turn, fluid line 50A can then be coupled with a new container to which the resuspended pellet 214 is transferred. Alternatively, the cells of the resuspended pellets 214 can be lysed within bag assemblies 48. The process can then be repeated of spinning manifold system 12 containing the lysed resuspension to form a new pellet and supernatant. The new pellet and supernatant can then be processed as discussed above. In another alternative, each bag assembly 48 can be cut open and pellet 214 removed. In yet another method, the bag assemblies 48 (housing pellets 214) still fluid coupled with manifold 46 can be stored in a freezer, either with or without a freezing medium being dispensed into each bag assembly 48 through manifold 46.

One of the benefits of retaining manifold 46 fluid coupled with bag assemblies 48 is that significantly fewer fluid couplings and fluid decouplings are required. For example, in contrast to separating each bag assembly 48 from manifold 46 prior to centrifugation, only a single decoupling of fluid line 50A from container 14 (FIG. 1) is required. Likewise, in contrast to fluid coupling each bag assembly 48 to container 220 after centrifugation, only a single fluid coupling between fluid line 50A and container 220 is required (FIG. 40). Similarly, only a single fluid coupling is required for resuspending pellets 214 within each bag assembly 48 and dispensing the resuspended pellets 214 from each bag assembly 48. As such, by retaining manifold 46 fluid coupled with each bag assembly 48, processing is significantly faster and there is less risk of contamination.

In another alternative method, bag assemblies 48 can be separated from manifold 46 prior to centrifugation, as discussed above. However, after centrifugation, each bag assembly 48 can be fluid coupled back to the same manifold 46 or a new manifold 46. The supernatant 216 and/or pellet 214 can then be removed and/or frozen using manifold 46 in the same methods as discussed above.

In another alternative, it is appreciated that outlet lines 92 (FIG. 1) can be eliminated from all of the bag assemblies 48 disclosed herein. In this alternative, inlet line 90 can be sequentially fluid coupled, such as by tube welding, to all of the needed containers and fluid sources, as discussed above with regard to outlet line 92, for removal of supernatant 216 and/or pellet 214 and for the resuspension of pellet 214.

In still another alternative, one or more spacer pads can be inserted into cavity 171 of inserts 166 or the cavity of rotors 121 and 121A on one or both opposing sides of each bag assembly 48. That is, depending on the size of bag assemblies 48 relative to the size of the cavities, the spacer pads can be used to fill extra space within the cavities so that bag assemblies 48 are more snugly fit within and better contoured to the cavities. The spacer pads thus help to prevent movement of bag assemblies 48 during centrifugation and help prevent the formation of creases and folds on bag assemblies during centrifugation. The spacer pads can be comprised of a resiliently flexible material such as foam, rubber, or synthetic rubber. However, other materials can also be used.

The inventive systems disclosed herein have a number unique advantages over the prior art. For example, the inventive bag assemblies with corresponding manifolds are cheap and inexpensive to produce relative to conventional bottles and flasks. Accordingly, once the suspension is separated and the supernatant and/or pellet are harvested, the bag assembly and manifold can simply be discarded, thereby avoiding the need for any cleaning or sterilization. That is, manifold system 12, manifold 46, and bag assembles 48 are designed as and can be used as single-use items that are discarded after a single use. Furthermore, the bag assemblies and manifold are easily collapsed and folded so that they are easy to transport and store with minimal space.

In addition, manifold 46, bag assemblies 48, container 220 and any other containers that may be fluid coupled with bag assemblies 48 can all be sterilized prior to use and all fluid couplings formed therewith or therebetween can be sterile connections. The transfer of suspension 18 from reactor 10 into bag assemblies 48 and the transfer of the supernatant 216 and pellet 214 out of bag assemblies 48 can thus be accomplished without exposing suspension 18 or its components to the open environment or other sources of contaminants. Thus, there is no risk, or at least minimal risk, of suspension 18 or its components being contaminated as they are processed, as set forth above. As a result, there is usually no need for post purification processing of the suspension components (other than, for example, filtering a small amount of residual cells from supernatant 216). The transfer of suspension 18 and separated components through closed lines also reduces the risk that product can be spilled. As such, there is lower risk of losing product by spilling. Delays and efforts in cleaning spilled product is also avoided. This closed processing in a sterile environment is in stark contrast to the prior art where both the original suspension and the formed supernatant are openly exposed to the environment as they are transferred into and out of the bottles or flasks that are used during centrifugation.

Furthermore, the use of clamp 226 or the other sealing mechanisms discussed herein provides an easy mechanism for isolating the supernatant from the pellet so that the pellet does not resuspend into the supernatant as the supernatant is removed from the bag assembly. Accordingly, use of clamp 226 or the other sealing mechanisms both increases the quality of the supernatant that can be removed and shortens production time. This is because the bag assemblies can be more easily handled and the supernatant can be more rapidly removed.

Finally, once the supernatant is removed, the bag assemblies provide an easily, efficient, and compact way to store and freeze the pellets without having to transfer to another container. The flexible bag assemblies also provide an easy and efficient way to resuspend the pellet within the bag assemblies for freezing or for subsequent use. Other advantages also exist.

Figure 41:
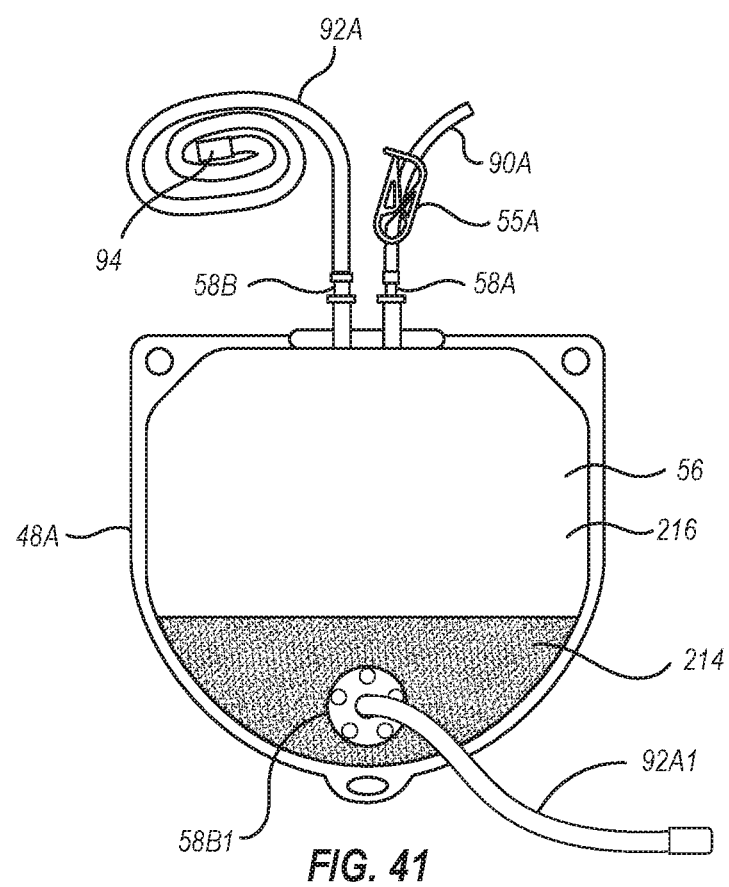
FIG. 41 is an elevated front view of the bag assembly shown in FIG. 2 having a second outlet coupled at a lower end thereof.

It is appreciated that the various components of the inventive system disclosed herein can have other configurations. For example, bag assembly 48 is shown in FIG. 21 as having inlet line 90 and outlet line 92 at top end 66. In an alternative embodiment, as shown in FIG. 41, bag assembly 48 can comprise a second outlet line 92A1 coupled with bag 54 through a port 58B1 at bottom end 68 and communicating with compartment 56. This second outlet line 92A1 could be used for the removal of pellet 214 when pellet 214 is in the form of a slurry. For example, either after removal of supernatant 216 or prior to the removal of supernatant 216, the second outlet 92A1 could be coupled to a new container 220 (FIG. 22) using a sterile connection. Pump 224 or expressor 430 could then be used to move pellet 214 to container 220. Where pellet 214 is moved to container 220, supernatant could be retained within bag assembly 48.

With reference to FIG. 1, manifold 46 is depicted and discussed as being comprised of fluid lines 50 and fittings 52 that are coupled together into the desired configuration and then separately fluid coupled with bag assemblies 48. However, in another alternative embodiment the manifold and bag assemblies can be integrally formed from the same overlapping sheets of film that are seamed together. This system avoids or minimizes the need for fluid coupling parts together which is both time consuming and increases the number of locations where contaminates could potentially enter.

Figure 42:
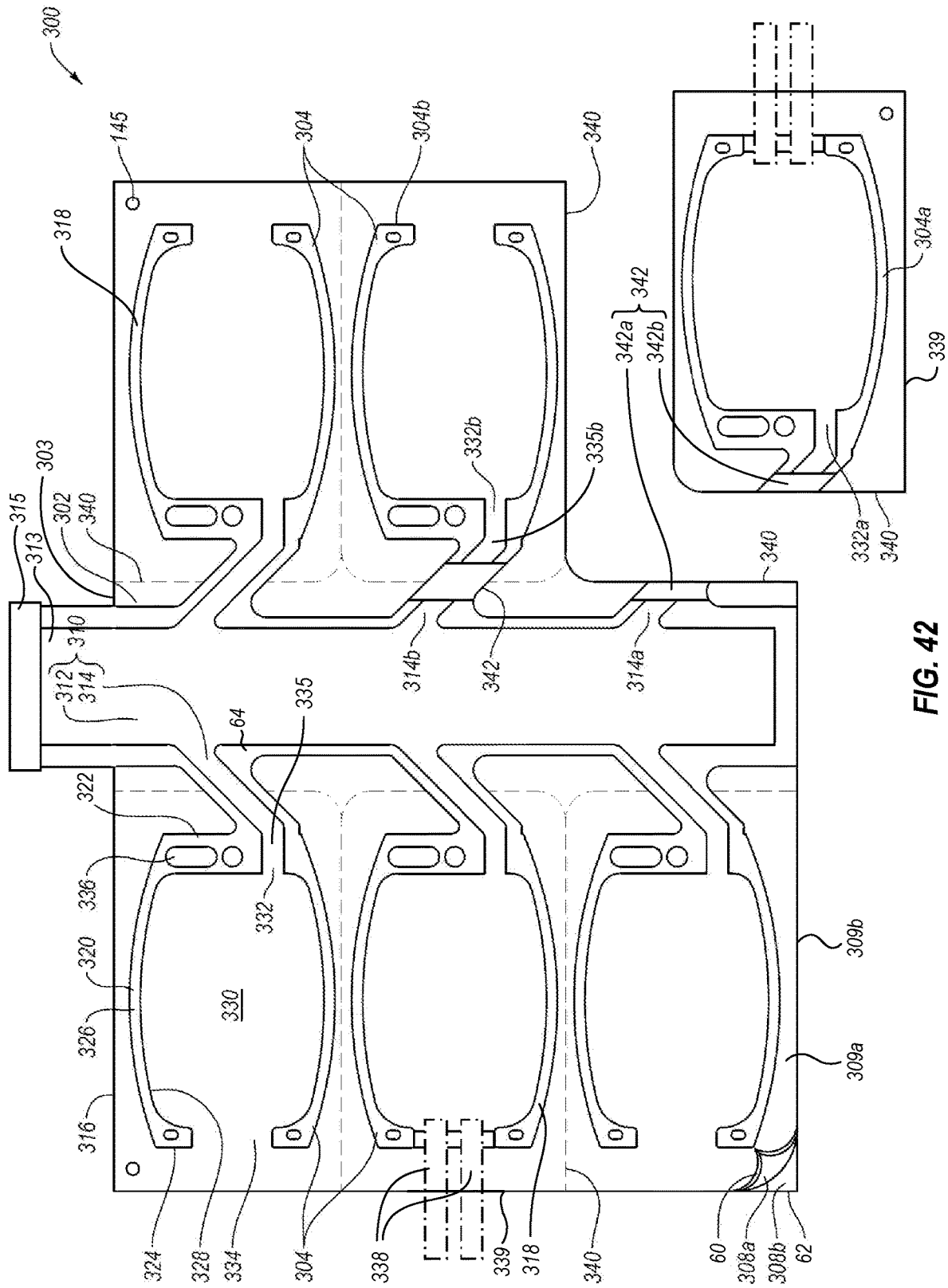
FIG. 42 is a top plan view of an alternative embodiment of a manifold system that can be coupled with the reactor in FIG. 1.

For example, FIG. 42 depicts a fluid manifold system 300 comprising a manifold 302 and a plurality of bags 304 that are integrally formed from the same overlapping sheets of film by selectively seaming together the overlapping sheets. More specifically, manifold 302 has a flexible body 303 comprised of flexible sheets 60 and 62, as previously discussed, with inside surfaces 308a and 308b facing each other and opposing outside surfaces 309a and 309b. A fluid flow path 310 is formed within manifold 302 by forming seam lines 64, as discussed above, that seal together sheets 60 and 62. Fluid flow path 310 comprises a main flow path 312 extending from a fluid inlet 313 and a plurality of secondary flow paths 314 extending therefrom. Body 303 can have a fitting 315 secured at fluid inlet 313 for fluid coupling with reactor 10 or a fluid line extending from reactor 10. Fitting 315 can comprise an aseptic connector. Alternatively, fitting 315 can be eliminated and fluid inlet 313 can otherwise be coupled to reactor 10 or a fluid line extending from reactor 10. Secondary flow paths 314 extend to bags 304 that are formed from the same sheets 60 and 62.

By being formed from the same sheets as manifold 302, bags 304 are flexible and collapsible like bags 54. Each bag 304 can be formed in the same way that manifold 302 is formed. That is, each bag 304 is formed by selectively seam sealing sheets 60 and 62 together to form seam lines 318 that outline the perimeter of bags 304.

Each bag 304 comprises a main body 320 extending from a lower end 322 to a spaced apart upper end 324 and having an outer wall 326 with an inner surface 328 bounding a compartment 330. A fluid inlet 332 and a fluid outlet 334 respectively extend through the lower and upper ends 322 and 324 of outer wall 326 to fluidly communicate with compartment 330. A fluid pathway 335 is also formed that communicates with compartment 330 and extends toward manifold 302 from fluid inlet 332. Similar to bags 54 one or more hanger holes 336 can also extend through main body 320.

Because bags 304 are formed from the same sheets 60 and 62 as manifold 302, each secondary flow path 314 can be formed so as to seamlessly flow into fluid pathway 335 without the use of a fitting or coupler. That is, each secondary flow path 314 can be integrally formed with fluid pathway 335 and its corresponding fluid inlet 332. Thus, the flexible body 303 of manifold 302 can be formed from a first portion of sheets 60 and 62 while bags 304 can be formed from a continuous second portion of sheets 60 and 62.

One or more connectors can be welded or otherwise fluidly connected to fluid outlet 334 of bag 304. Each connector can comprise a port, a tube, or the like. For example, in the depicted embodiment, the connectors comprise a pair of tubes 338 secured within fluid outlet 334 of bag 304. Tubes 338 can be welded, glued, fastened, or otherwise secured to bags 304 at fluid outlet 334. Tubes 338 can be used like lines 90 and 92 on bag assemblies 48 for removing supernatant 216 and pellet 214 from compartment 330. The combination of each bag 304 and corresponding tubes 338 is referred to herein as a bag assembly 339.

If desired, manifold system 300 can include means for easily detaching bags 304 from manifold 302 after bags 304 have been filled with suspension 18. For example, for each bag 304, a plurality of perforations 340 can extend through both sheets 60 and 62 in a line extending from the perimeter edge 316 of flexible sheets 306, around the corresponding bag 304, and back to perimeter edge 316. The exception is that perforations 340 are not formed across fluid flow path 310. As a result, each bag 304 can be detached from manifold 302 by simply tearing along perforations 340 corresponding to the bag 304, as has been done with bag 304a. As shown in the depicted embodiment, portions of perforations 340 can be shared by more than one bag 304.

Whether using perforations 340 or not, before detaching bag 304 from manifold 302, fluid inlet 332 of bag 304 and secondary flow path 314 of manifold 302 should be isolated and sealed from each other somewhere along fluid pathway 335. If both fluid inlet 332 and secondary flow path 314 are not sealed, fluid may leak out from bag 304 and/or manifold 302 when separated and contaminants may enter therein. In one embodiment, fluid inlet 332 and secondary flow path 314 are sealed by selective welding. This can be accomplished by welding the portions of sheets 306a and 306b corresponding to a location along fluid pathway 335 after passing suspension 18 from reactor 10, through manifold 302 into bags 304. For example, in FIG. 42 fluid pathway 335b corresponding to bag 304b has been welded closed at weld seam 342. As depicted, the welding should be aligned with the perforations 340 corresponding to the bag 304. By so doing, when bag 304 is detached from manifold 302 by tearing along perforations 340, as is the case with bag 304a, a cut can be made across welded seam 342 so that a portion 342A of seam 342 can remain with manifold 302 while a separate portion 342b of seam 342 can go with bag 304. This allows bag 304 and manifold 302 to both be sealed after separation. The cut can be made as part of the welding process or subsequent thereto.

Bag assemblies 339 can be used substantially the same way as bag assemblies 49. That is, after bag assemblies 339 are filled with suspension 18, each bag assembly is removed from manifold 302 and placed within a centrifuge with upper end 324 disposed upward. The centrifuge rotates bag assemblies 339 causing suspension 18 to separate into supernatant 216 and pellet 214. Supernatant 216 is then removed from bag assembly 339 through one of tubes 338 in the same way that supernatant is removed through outlet line 92 of bag assembles 48. Again, as needed, clamp 226 or other sealing mechanisms can be used across bag assemblies 339 to isolate the supernatant 216 from pellet 214. Finally, pellet 214 can be stored within bag assemblies 339 or removed as discussed above with regard to bag assembles 48. Further disclosure with regard to manifold system 300 and other manifold systems that can be used in the present disclosure are disclosed in U.S. Pat. No. 9,073,650, issued Jul. 7, 2015, which is incorporated in its entirety herein by specific reference.

Figure 43:
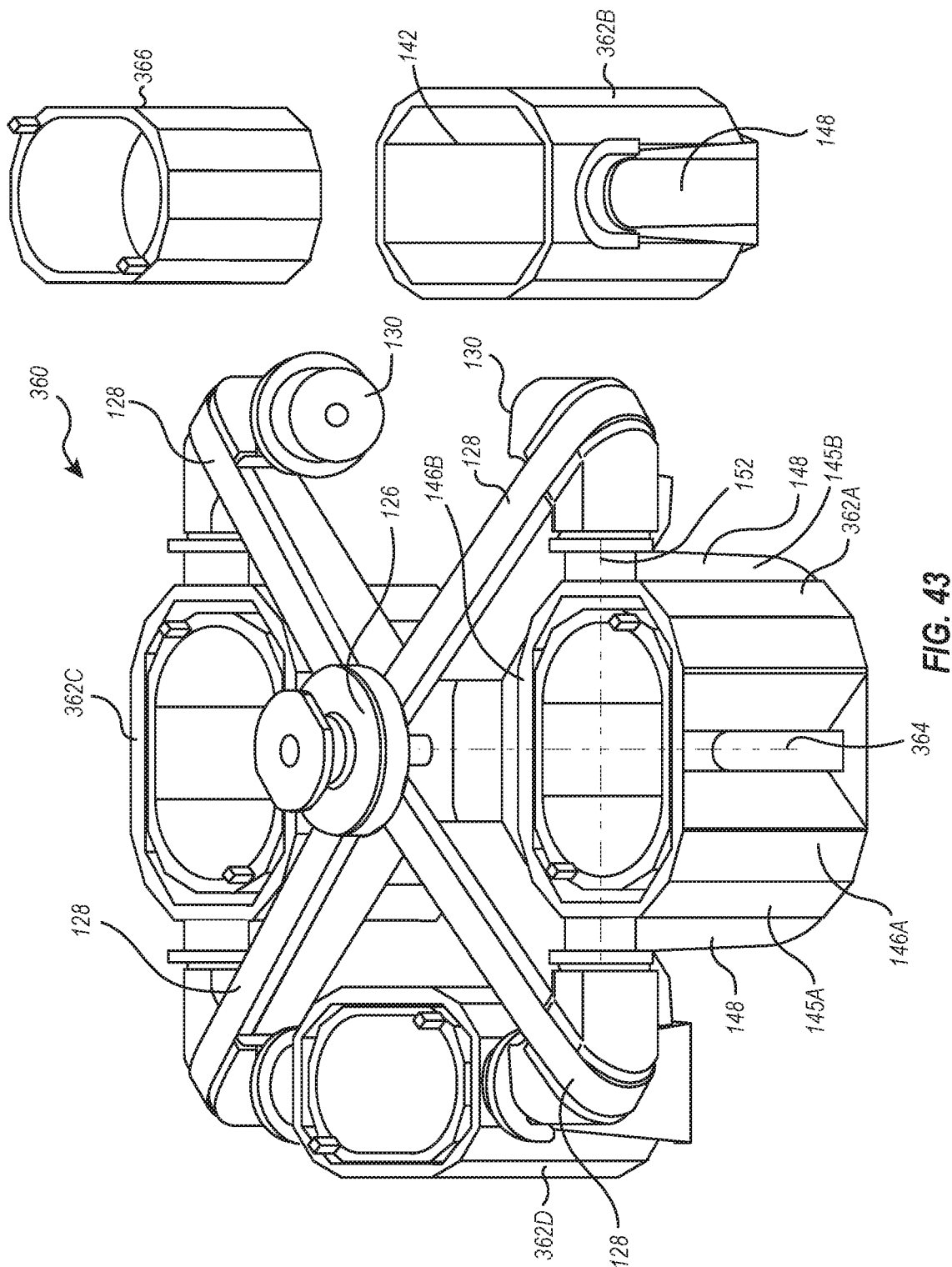
FIG. 43 is a perspective view of an alternative embodiment of the rotor shown in FIG. 11 having alternative buckets mounted thereon.

Depicted in FIG. 43 is another alternative embodiment of a rotor 360 that can be used with centrifuge 212. Rotor 360 is similar to rotor body 122 and like element are identified by like reference characters. Rotor 360 includes central hub 126 having arms 128 outwardly projecting therefrom. Hangers 130 are mounted on the opposing sides of each arm 128. Buckets 362A-D are provided that bound elongated cavities 142 that are each configured to receive a bag assembly. Each bucket 362A-D has receivers 148 disposed thereon for removably mounting to hangers 130 so that buckets 362 can swivel. However, in contrast to buckets 124, buckets 362 have receivers 148 disposed on opposing ends walls 145A and 145B as opposed to on opposing side walls 146A and 146B. As such, longitudinal axis 152 of cavity 142 of buckets 362 is perpendicular to a radial axis 364 that radially extends out of hub 126. As needed cup shaped inserts 366 can be used within buckets 362 to directly support the bag assemblies.

Figure 44:
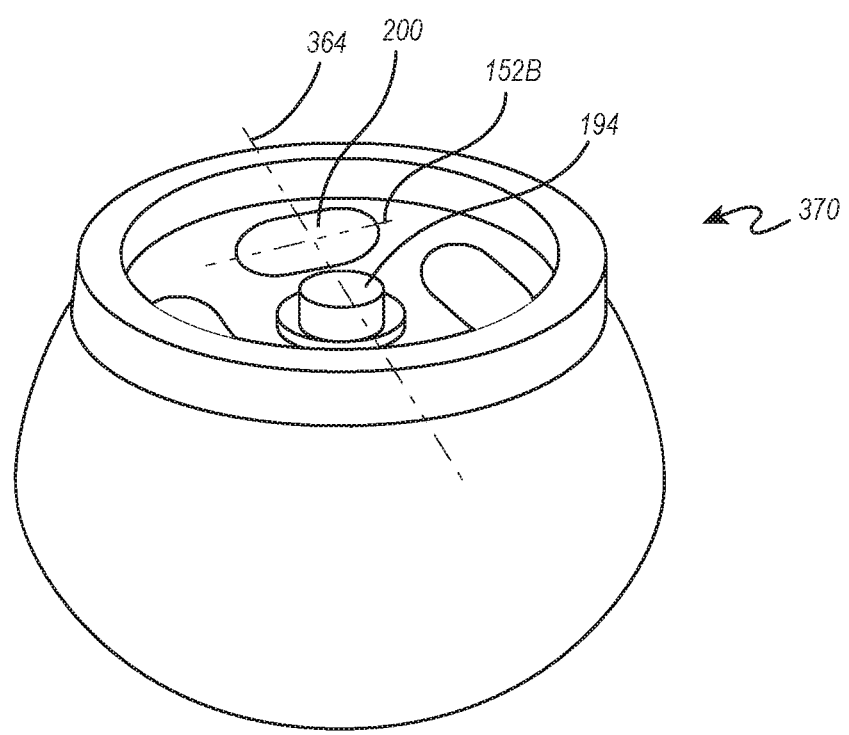
FIG. 44 is a perspective view of an alternative embodiment of the rotor shown in FIG. 19.

Depicted in FIG. 44 is an alternative rotor 370 which is the same as rotor 121A in FIG. 19 except that cavities 200 are again configured so that longitudinal axis 152B extends between opposing end walls and is now perpendicular to radial axis 364 extending from hub 194. As needed, inserts 166 can be positioned within cavities 200 of rotor 370.

Figure 45:
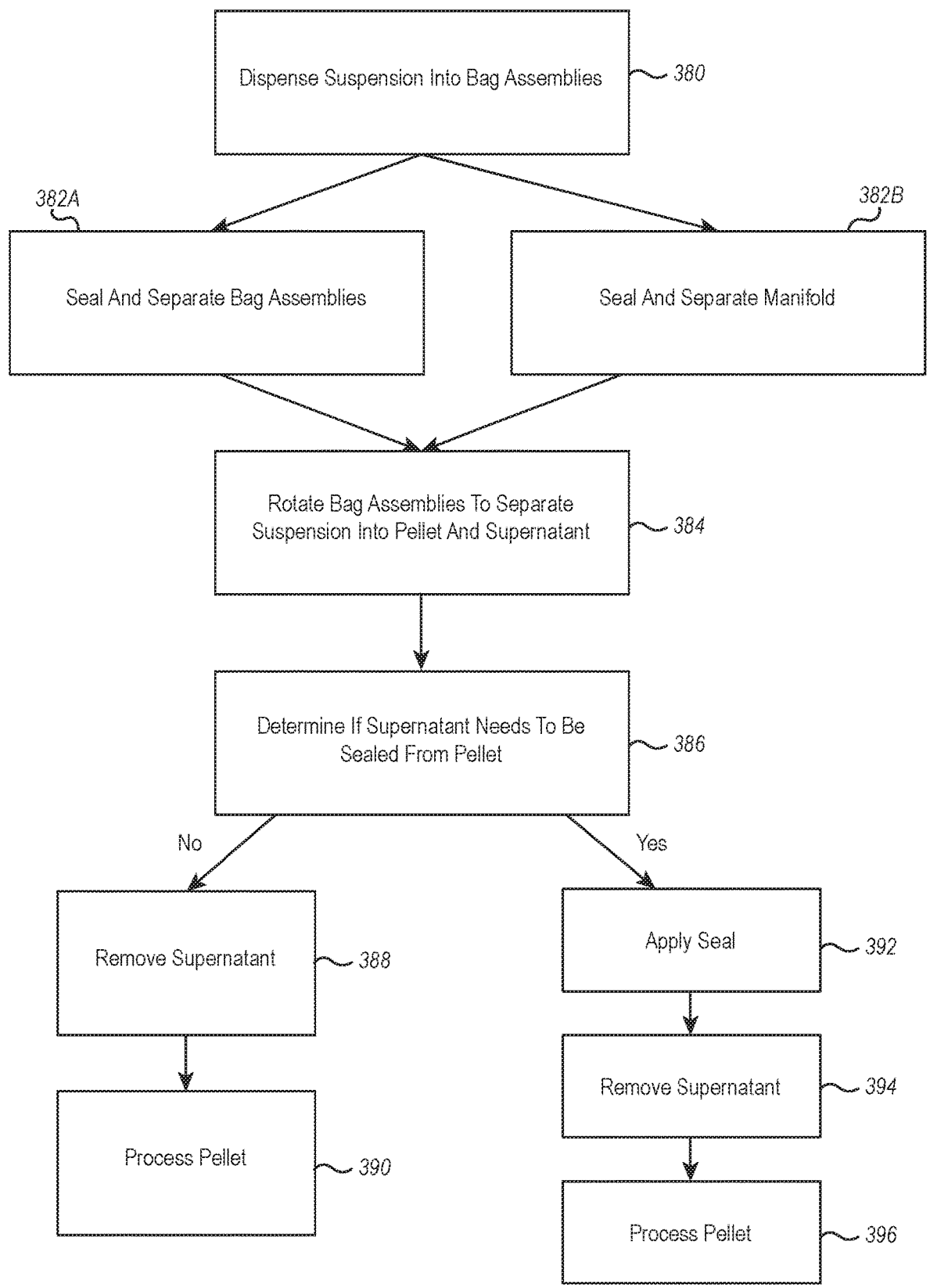
FIG. 45 is a block diagram showing method steps of the present disclosure.

Depicted in FIG. 45 is one example of a block flow diagram outlining methods steps of one embodiment of the present disclosure. In step 380 the suspension is dispensed into bag assemblies of the present disclosure. As discussed herein, the suspension is typically a biological suspension that is grown in a bioreactor or fermenter but other non-biological suspensions can also be processed using features and methods of the present disclosure. Where it is desired to fill multiple bag assemblies, the suspension can be transferred using a manifold. Otherwise, a single fluid line can be used to fill a single bag assembly. The manifolds and bag assemblies are coupled together, sealed and sterilized, such as by irradiation, prior to use. Other sterilizing processes that can be used include autoclaving or exposing the open manifolds and bag assemblies to ozone or other sterilizing contact reagents and then sealing the open manifolds and bag assemblies closed. During use, the manifolds are fluid coupled to the container of the bioreactor or fermenter using a sterile connection. As such, the manifolds form a sterile pathway through which the suspension can pass from the bioreactor or fermenter to the bag assemblies without risk of contamination.

The bag assemblies are filled with suspension by weight, such as by using a scale, or by volume. Clamps or valves can be used to control fluid flow into each bag assembly. In method step 382A, once the bag assemblies are filled, the bag assemblies are sealed closed and separated from the manifold. Sealing the bag assemblies closed is typically accomplished by welding closed a section of the inlet line to the bag assemblies. The inlet line can then be cut through the weld to separate the bag assemblies from the manifold.

The bag assemblies comprise flexible, collapsible bags that bound a chamber in which the suspension is maintained. The bags can comprise two dimension bags which typically comprises two overlaying sheets of flexible film that are seamed together or can comprise three dimensional bags that are typically comprised of three of more sheets of flexible film seamed together. The bag assembles can further comprise one, two, three, or more ports and/or sections of tubing or tubes that couple with the collapsible bags and communicate with the compartment.

As an alternative, in step 382B the bag assemblies are left fluid coupled to the manifold while the inlet fluid line of the manifold is sealed closed and separated from the container of the reactor. In this method, the bag assemblies remain fluid coupled to the manifold throughout most if not all of the processing. Keeping the manifold fluid coupled to the bag assemblies limits the required number of fluid couplings and fluid decouplings.

In step 384, the filled bag assembles, either connected to the manifold or separated from the manifold, are rotated to separate the suspension into a more dense pellet comprised of cells, microorganisms and/or other solids and a less dense supernatant that collects as a liquid above the pellet. The rotation of the bag assemblies is accomplished using a centrifuge. In one embodiment, a lower end of the bag assemblies inwardly tapers so that the pellet can more efficiently collect and consolidate in a confined area during centrifugation. In addition, the centrifuge rotors can be formed with elongated cavities having lower ends that also inwardly taper. The rotor cavities are designed to have a shape that is generally complementary to the shape of the bag assemblies. This enables the rotors to fully support the bag assemblies to prevent unwanted stress during centrifugation, assists in helping to collect and consolidate the pellet in a confined area within the bag assemblies, and helps prevent unwanted creases or folds in the bag assemblies that can disrupt the collection of the pellet.

In one method, bag assemblies are first loaded into inserts and the inserts are then loaded into the centrifuge rotors. The bag assemblies can be loaded into the inserts either before or after being filled with the suspension. In one embodiment, the inserts can be compressible and resiliently flexible, thereby providing cushioning to reduce stress and provide contouring on bag assemblies during centrifugation. Alternatively, inserts can be thin walled structures that are configured to make it easier and quicker to load and unload the bag assemblies on centrifuge rotors.

In step 386 it is determined whether the supernatant needs to be sealed off from the pellet. This determination is typically made based upon the type of cells or microorganisms being processed. Where the pellet is firmly consolidated and not easily disrupted, i.e., not easily resuspended into the supernatant, no sealing is required. In this case, the supernatant is removed from the bag assembles in step 388. This is accomplished by removing the bag assemblies from the centrifuge, with or without the inserts, coupling an outlet line of the bag assemblies to a container using a sterile connection, and then using a peristaltic pump or expressor to dispense the supernatant into the container. If a pump is used, the bag assemblies can be retained within a rotor bucket and/or the insert, or supported on or in a rack, stand, container or other support. Typically, each bag assembly is retained in an upstanding position during the pumping process. Similarly, where the bag assemblies are retained coupled to the manifold, the bag assemblies and manifold are removed from the centrifuge, with or without the inserts, and the manifold is fluid coupled to the container using a sterile connection. A peristaltic pump or expressor is then used to dispense the supernatant from each bag assembly into the container by passing through the manifold.

Once the supernatant has been removed, the remaining pellet is processed in step 390. This can simply entail storing the bag assembly with the pellet in a freezer for subsequent use. Alternatively, a freezing medium can be dispensed into the bag assembly and the pellet resuspended to form a secondary suspension. The bag assembly containing the secondary suspension can then also be stored in a freezer for subsequent use. In yet another alternative, a liquid, such as growth medium, can be dispensed into the bag assembly and the pellet resuspended to form another secondary suspension. The secondary suspension can be moved into a new container or the secondary suspension can by lysed, separated by centrifugation and then further processed to remove the supernatant using the processes described herein. In yet another alternative, the bag assembly can be cut open and the pellet manually removed. The above processes can be separately performed on each individual bag assembly or the processes can be performed through the manifold coupled to the bag assemblies.

If it is determined that the supernatant does need to be sealed from the pellet to prevent resuspension of the pellet into the supernatant, in step 392 the seal is applied. In one embodiment, the seal can comprise a clamp that is removably attached over the bag assembly directly above of the pellet. The clamp divides the compartment into an upper compartment that houses the supernatant and a lower compartment that houses the pellet. The upper compartment is sealed closed from the lower compartment by the clamp. In contrast to using a clamp, the seal can be formed by pinching together two structural members on opposing sides of the bag assembly or by forming a weld across the compartment of the bag. If the bag assembly is too full to initially apply the seal, a portion of the supernatant can first be removed, as discussed above in step 388, until sufficient supernatant is removed so that the seal can be applied.

Once the seal is formed, the supernatant or remaining supernatant is removed from the bag assembly in step 394 using the same method as discussed above with regard to step 388. However, with the seal applied, the supernatant can typically be more rapidly removed and the bag assembly can be placed in other positions because there is no risk of the pellet being disturbed. Finally, in step 396 the pellet can be processed using the same methods as discussed above with step 390. Once the supernatant is removed, the seal can be removed as desired.

The present disclosure may be embodied in other specific forms without departing from its spirit or essential characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

What is claimed is:

1. A method for separating a biological suspension, the method comprising:
   passing a liquid suspension comprised of cells or microorganisms through a manifold and into a sterile compartment of a first bag assembly and a sterile compartment of a second bag assembly, the first bag assembly and the second bag assembly each being separately coupled to the manifold and each comprising a collapsible bag comprised of one or more sheets of flexible film;
   positioning the first bag assembly within a cavity of a first insert;
   placing the first insert within a first cavity of a rotor of a centrifuge either before or after positioning the first bag assembly within the cavity of the first insert, the first insert having an annular lip portion that freely projects out of the cavity of the rotor by a distance of at least 1 cm; and
   rotating the first bag assembly and the second bag assembly using the centrifuge so that the liquid suspension separates within the compartment of the first bag assembly and the second bag assembly into a pellet comprised of the cells or microorganisms and a liquid supernatant.

2. The method as recited in claim 1, wherein the liquid suspension is dispensed into the compartment of the first bag assembly through a sterile pathway.

3. The method as recited in claim 1, further comprising:
   sealing the compartment of the first bag assembly and the second bag assembly closed; and
   placing the sealed second bag assembly within a second cavity of the rotor of the centrifuge.

4. The method as recited in claim 3, wherein the steps of placing comprises:
   positioning the second bag assembly within a cavity of a second insert; and
   placing the second insert within the second cavity of the rotor.

5. The method as recited in claim 1, wherein the cavity of the first insert is elongated.

6. The method as recited in claim 1, wherein the cavity of the first insert has a lower end that inwardly tapers.

7. The method as recited in claim 1, wherein the rotor comprises a swinging-bucket rotor and the first cavity of the rotor is formed on a bucket of the swinging bucket rotor.

8. The method as recited in claim 1, wherein the first cavity of the rotor is elongated and has a lower end that inwardly tapers.

9. The method as recited in claim 1, wherein the first bag assembly has an upper end with one or more tubes or ports coupled thereto and an opposing lower end, the lower end being more inwardly tapered than the upper end.

10. The method as recited in claim 1, further comprising transferring at least a portion of the liquid supernatant from the compartment of the first bag assembly into a separate container through a sterile pathway while the pellet is retained within the compartment of the first bag assembly.

11. The method as recited in claim 10, further comprising:
    dispensing a liquid into the compartment of the first bag assembly after transferring the at least a portion of the liquid supernatant from the compartment; and
    mixing the liquid with the pellet to form a secondary suspension.

12. The method as recited in claim 11, further comprising:
    rotating the first bag assembly containing the secondary suspension using a centrifuge to separate the secondary suspension into a secondary pellet and a secondary supernatant; and
    transferring at least a portion of the secondary supernatant from the compartment of the first bag assembly into a separate container while the secondary pellet is retained within the compartment of the first bag assembly.

13. The method as recited in claim 1, wherein the pellet has a greater density or viscosity than the liquid supernatant.

14. The method as recited in claim 1, further comprising:
    forming a seal across the first bag assembly so as to separate the compartment of the first bag assembly into an upper compartment that houses at least a portion of the supernatant and a lower compartment that houses the pellet, the upper compartment being sealed closed from the lower compartment; and
    transferring at least a portion of the supernatant in the upper compartment into a separate container.

15. The method as recited in claim 14, wherein the step of forming a seal comprises applying a clamp across the first bag assembly.

16. The method as recited in claim 14, further comprising:
    removing the seal from across the first bag assembly;
    delivering a liquid into the compartment of the first bag assembly; and mixing the pellet with the liquid to form a secondary suspension.

17. The method as recited in claim 1, further comprising:
placing the second bag assembly within a second cavity of the rotor of the centrifuge, the manifold being fluid coupled with the first bag assembly and the second bag assembly; and
the step of rotating comprising rotating the first bag assembly, the second bag assembly and the manifold using the centrifuge.

18. The method as recited in claim 1, wherein the step of positioning comprises inserting the first bag assembly within the cavity of the first insert and then placing the first insert within the first cavity of the rotor.

19. The method as recited in claim 17, further comprising:
removing the first bag assembly, the second bag assembly and the manifold from the rotor;
fluid coupling the manifold to a container; and
dispensing at least a portion of the supernatant from the first bag assembly to the container through the manifold while the pellet is retained within the compartment of the first bag assembly.

20. The method as recited in claim 19, further comprising:
decoupling the manifold from the container;
delivering a liquid into the compartment of the first bag assembly through the manifold; and
mixing the pellet with the liquid to form a secondary suspension within the first bag assembly.

21. A method for separating a biological, the method comprising: dispensing a liquid suspension disposed within a fermenter or bioreactor and comprised of cells or microorganisms through a manifold and into a compartment of each of a plurality of bag assemblies that are each fluid coupled with the manifold, each of the plurality of bag assemblies comprising a collapsible bag comprised of one or more sheets of flexible film; separating the manifold from the fermenter or bioreactor; placing each of the plurality of bag assemblies fluid coupled with the manifold into a corresponding separate cavity of a rotor of a centrifuge; and activating the centrifuge so that the liquid suspension within the compartment of each of the plurality of bag assemblies fluid coupled with the manifold separates into a pellet comprised of the cells or microorganisms and a liquid supernatant.

22. The method as recited in claim 21, further comprising:
fluid coupling the manifold to a container; and
dispensing at least a portion of the supernatant from a first bag assembly of the plurality of bag assemblies into the container through the manifold while the pellet of the first bag assembly is retained within the compartment of the first bag assembly.

23. The method as recited in claim 22, further comprising:
decoupling the manifold from the container;
delivering a liquid into the compartment of the first bag assembly through the manifold; and
mixing the pellet within the first bag assembly with the liquid to form a secondary suspension within the first bag assembly.

24. The method as recited in claim 9, wherein the lower end of the first bag assembly is free of any ports or tubes coupled thereto.

25. A method for separating a biological suspension, the method comprising:
dispensing a liquid suspension comprised of cells or microorganisms into a sterile compartment of a first bag assembly, the first bag assembly comprising a collapsible bag comprised of one or more sheets of flexible film;
sealing the compartment of the first bag assembly closed;
positioning the first bag assembly within a cavity of an insert;
placing the insert within a cavity of a rotor of a centrifuge, the insert having an annular lip portion that freely projects out of the cavity of the rotor by a distance of at least 1 cm; and
rotating the first bag assembly using the centrifuge so that the liquid suspension separates within the compartment into a pellet comprised of the cells or microorganisms and a liquid supernatant.

26. The method as recited in claim 25, wherein the cavity of the insert is elongated.

27. The method as recited in claim 25, wherein the cavity of the insert has a lower end that inwardly tapers.

28. The method as recited in claim 25, wherein the rotor comprises a swinging-bucket rotor and the first cavity of the rotor is formed on a bucket of the swinging bucket rotor.

29. A method for separating a biological suspension, the method comprising: dispensing a liquid suspension comprised of cells or microorganisms into a sterile compartment of a first bag assembly, the first bag assembly comprising a collapsible bag comprised of one or more sheets of flexible film; rotating the first bag assembly using a centrifuge so that the liquid suspension separates within the compartment into a pellet comprised of the cells or microorganisms and a liquid supernatant; transferring at least a portion of the liquid supernatant from the compartment of the first bag assembly into a separate container through a pathway while the pellet is retained within the compartment of the first bag assembly; dispensing a liquid into the compartment of the first bag assembly after transferring the at least a portion of the liquid supernatant from the compartment; mixing the liquid with the pellet to form a secondary suspension; rotating the first bag assembly containing the secondary suspension using a centrifuge to separate the secondary suspension into a secondary pellet and a secondary supernatant; and transferring at least a portion of the secondary supernatant from the compartment of the first bag assembly into a further separate container while the secondary pellet is retained within the compartment of the first bag assembly.

30. The method as recited in claim 29, wherein the at least a portion of the liquid supernatant is transferred from the compartment of the first bag assembly into the separate container through a sterile pathway while the pellet is retained within the compartment of the first bag assembly.

31. A method for separating a biological suspension, the method comprising:
dispensing a liquid suspension comprised of cells or microorganisms into a sterile compartment of a first bag assembly, the first bag assembly comprising a collapsible bag comprised of one or more sheets of flexible film;
sealing the compartment of the first bag assembly closed;
positioning the first bag assembly within a cavity of an insert, the insert being disposed within a cavity of a rotor of a centrifuge, the insert having an annular lip portion that freely projects out of the cavity of the rotor by a distance of at least 1 cm; and
rotating the first bag assembly using the centrifuge so that the liquid suspension separates within the compartment into a pellet comprised of the cells or microorganisms and a liquid supernatant.

* * * * *